US011555819B2

(12) United States Patent
Mizoguchi et al.

(10) Patent No.: US 11,555,819 B2
(45) Date of Patent: Jan. 17, 2023

(54) CANCER TEST DEVICE, CANCER TEST METHOD, AND STAINING AGENT FOR USE IN CANCER TEST

(71) Applicant: MIE UNIVERSITY, Tsu (JP)

(72) Inventors: Akira Mizoguchi, Mie (JP); Koji Tanaka, Mie (JP); Naoyuki Katayama, Mie (JP); Tetsuya Nosaka, Mie (JP); Kyosuke Tanaka, Mie (JP); Shujie Wang, Mie (JP); Aika Kaito, Mie (JP); Kousyoku Sai, Mie (JP); Kazushi Kimura, Mie (JP)

(73) Assignee: MIE UNIVERSITY, Mie (JP)

( * ) Notice: Subject to any disclaimer, the term of this patent is extended or adjusted under 35 U.S.C. 154(b) by 879 days.

(21) Appl. No.: 16/301,939

(22) PCT Filed: May 18, 2017

(86) PCT No.: PCT/JP2017/018755
§ 371 (c)(1),
(2) Date: Nov. 15, 2018

(87) PCT Pub. No.: WO2017/200066
PCT Pub. Date: Nov. 23, 2017

(65) Prior Publication Data
US 2019/0285638 A1    Sep. 19, 2019

Related U.S. Application Data

(63) Continuation of application No. PCT/JP2017/006962, filed on Feb. 23, 2017.

(30) Foreign Application Priority Data

May 18, 2016   (JP) ................................. 2016-099997

(51) Int. Cl.
G01N 35/00    (2006.01)
G01N 33/574   (2006.01)
(Continued)

(52) U.S. Cl.
CPC ......... *G01N 33/57496* (2013.01); *A61B 1/00* (2013.01); *G01N 1/30* (2013.01);
(Continued)

(58) Field of Classification Search
None
See application file for complete search history.

(56) References Cited

U.S. PATENT DOCUMENTS 8,977,017 B2 *  3/2015  Otsuka ................. G06T 7/0012
                                                382/128
2003/0170613 A1  9/2003  Straus
(Continued)

FOREIGN PATENT DOCUMENTS

JP    2005-518553    6/2005
JP    2009-545737    12/2009
(Continued)

OTHER PUBLICATIONS

International Search Report dated Aug. 15, 2017 in International Application No. PCT/JP2017/018755.

*Primary Examiner* — Jyoti Nagpaul
(74) *Attorney, Agent, or Firm* — Wenderoth, Lind & Ponack, L.L.P.

(57) ABSTRACT

A cancer test device (1) is provided with: an application unit (40) for applying a staining agent (45), which can selectively stain a product of a cancer-relating gene in a living cell a chromatic color, onto a group of living cells; an imaging unit (10) for imaging the group of living cells having the staining agent (45) applied thereto; and a determination unit (52) for determining the level of malignancy of cancerization of the
(Continued)

group of living cells on the basis of the state of the stained expression pattern of the cancer-relating gene in the group of living cells in an image obtained by the aforementioned imaging.

11 Claims, 32 Drawing Sheets

(51) Int. Cl.
    *G01N 1/30*     (2006.01)
    *G01N 1/31*     (2006.01)
    *G01N 21/78*     (2006.01)
    *G01N 33/48*     (2006.01)
    *G01N 21/64*     (2006.01)
    *A61B 1/00*     (2006.01)
    *G01N 33/483*     (2006.01)
    *C12M 1/00*     (2006.01)
    *G01N 33/50*     (2006.01)

(52) U.S. Cl.
    CPC ............... *G01N 1/31* (2013.01); *G01N 21/64* (2013.01); *G01N 21/78* (2013.01); *G01N 33/48* (2013.01); *C12M 41/06* (2013.01); *G01N 33/4833* (2013.01); *G01N 33/50* (2013.01); *G01N 33/574* (2013.01); *G01N 2001/302* (2013.01)

(56) References Cited

U.S. PATENT DOCUMENTS

| | | | |
|---|---|---|---|
| 2007/0172911 A1* | 7/2007 | Farrell | G01N 1/30 |
| | | | 435/40.5 |
| 2009/0326359 A1 | 12/2009 | Hendriks et al. | |
| 2016/0041100 A1 | 2/2016 | Mizoguchi et al. | |
| 2016/0299170 A1 | 10/2016 | Ito et al. | |

FOREIGN PATENT DOCUMENTS

| | | |
|---|---|---|
| WO | 2014/157645 | 10/2014 |
| WO | 2014/157703 | 10/2014 |
| WO | WO 2014/157703 | * 10/2014 |
| WO | 2015/190225 | 12/2015 |

* cited by examiner

[Figure 1A]
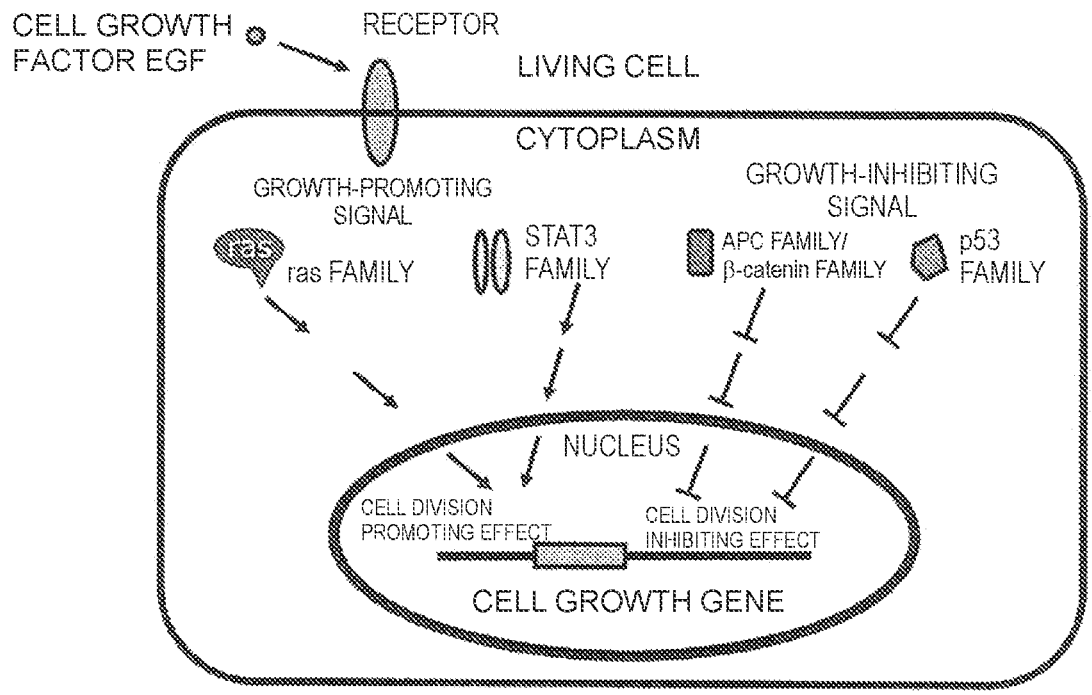
[Figure 1B]
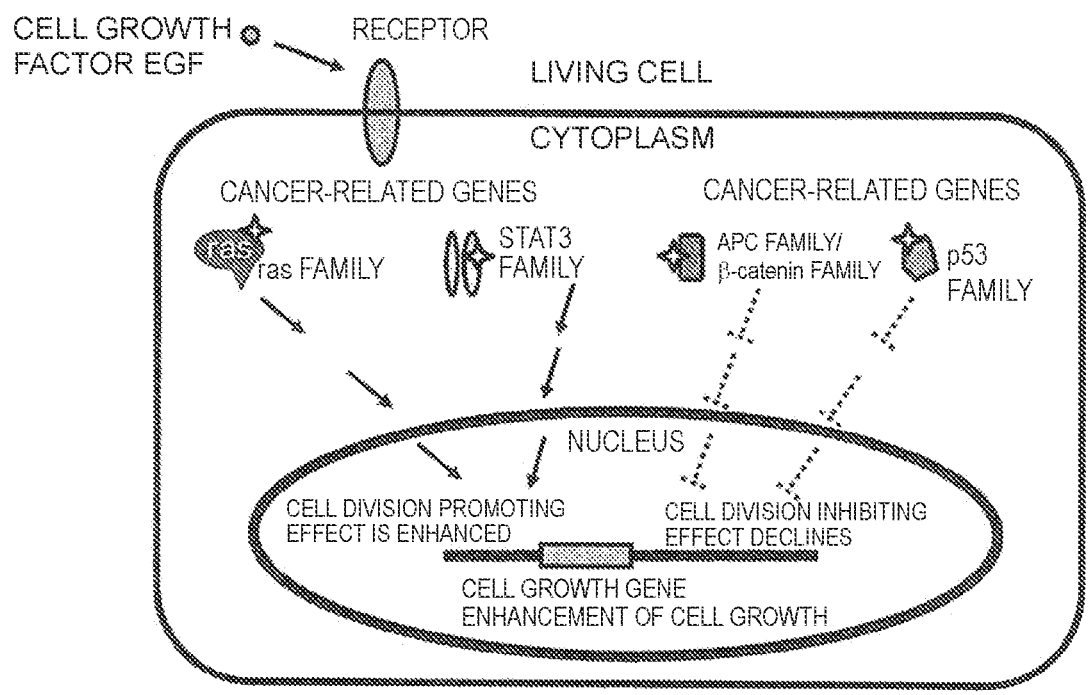
✦ : CROSS STAR MARKS EACH INDICATE CANCEROUS MUTATION
   THAT OCCURS IN CORRESPONDING CANCER-RELATED GENE PRODUCT

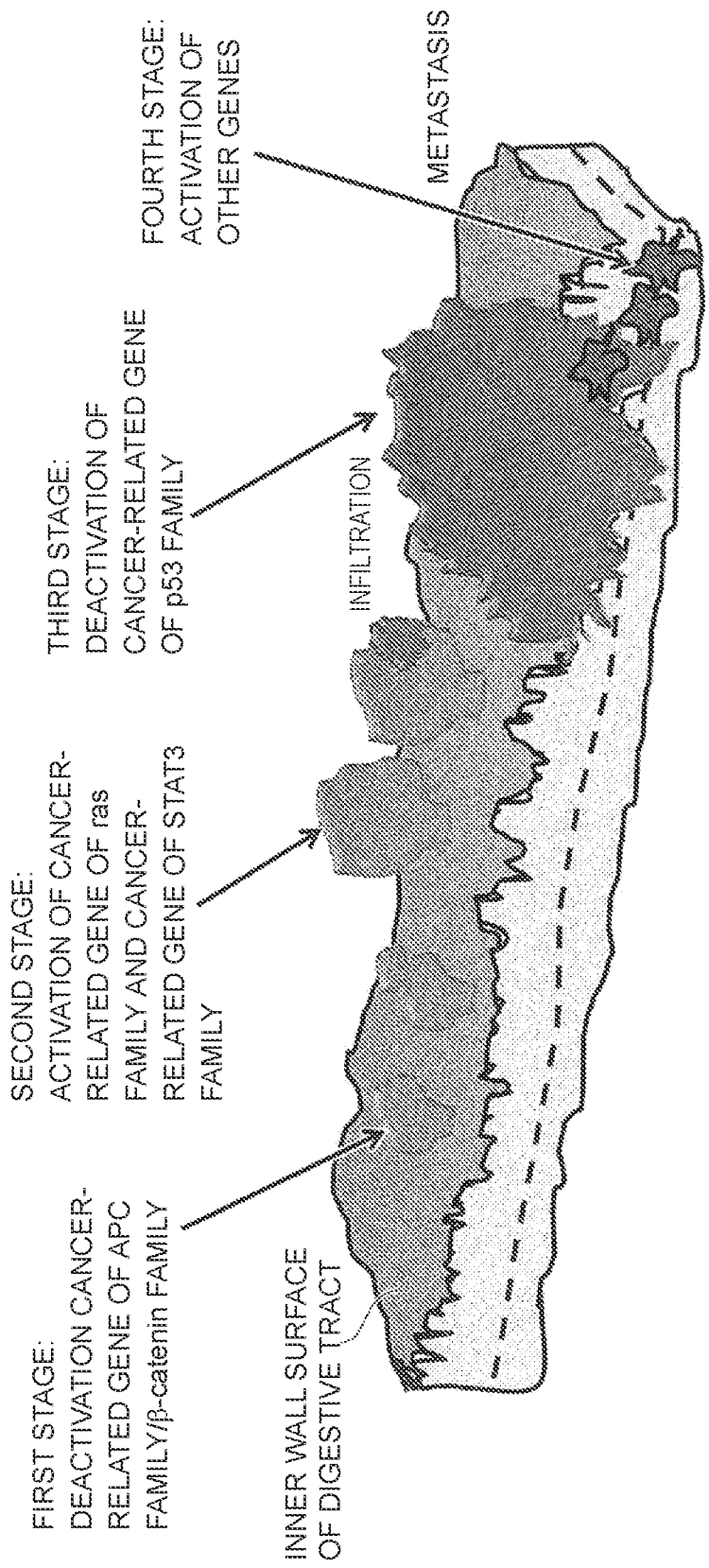
[Figure 1C]

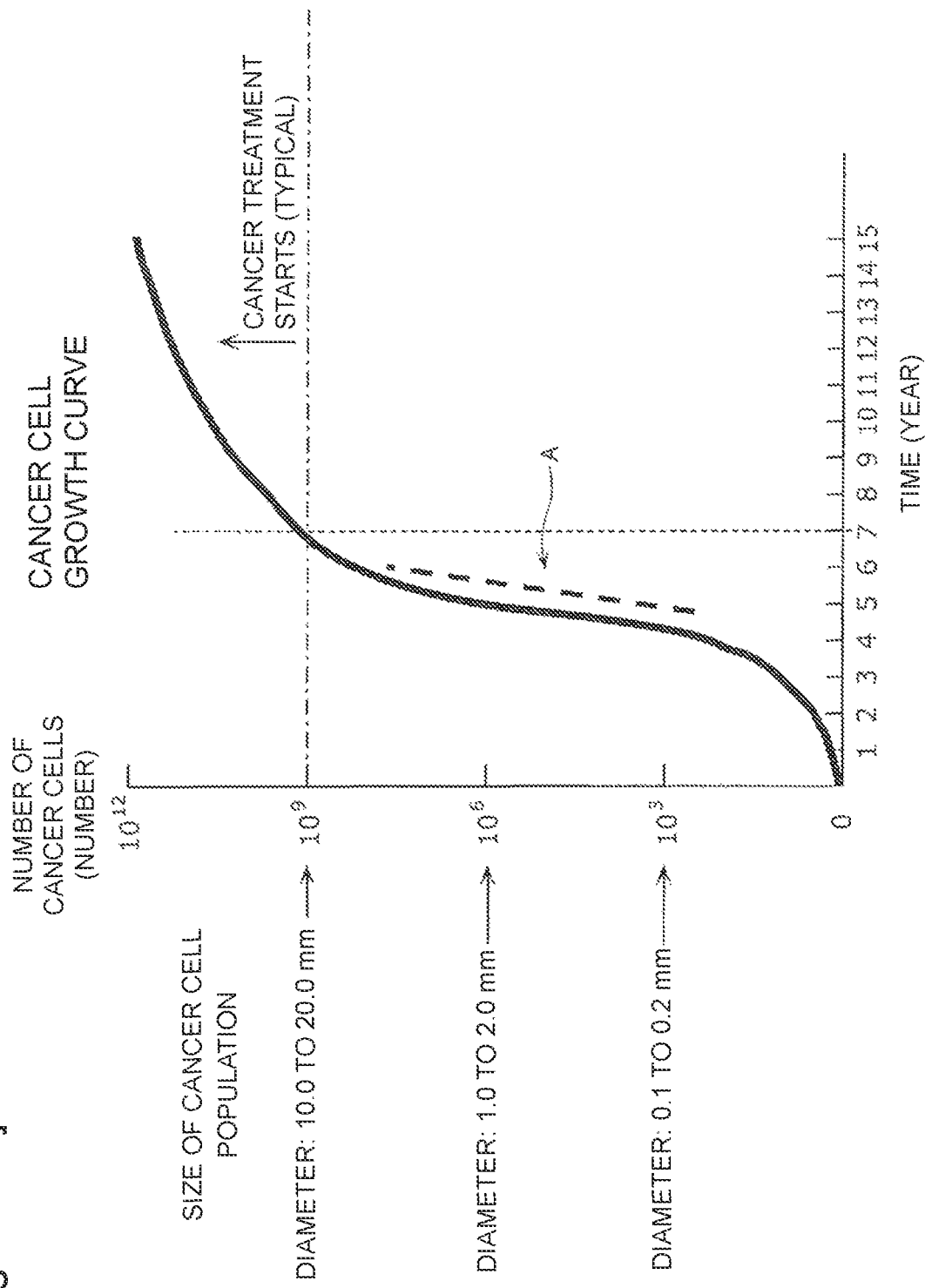
[Figure 1D]

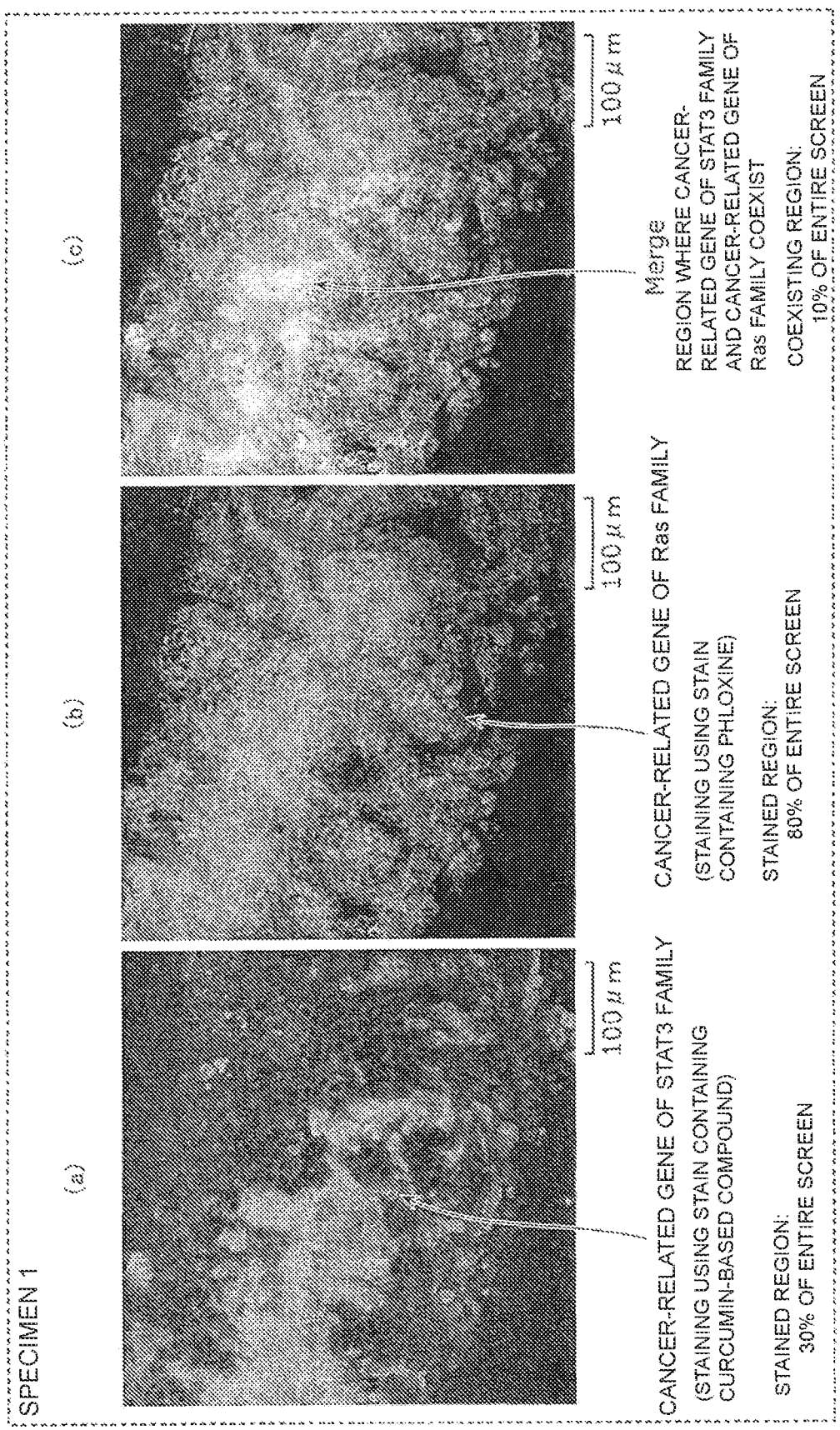

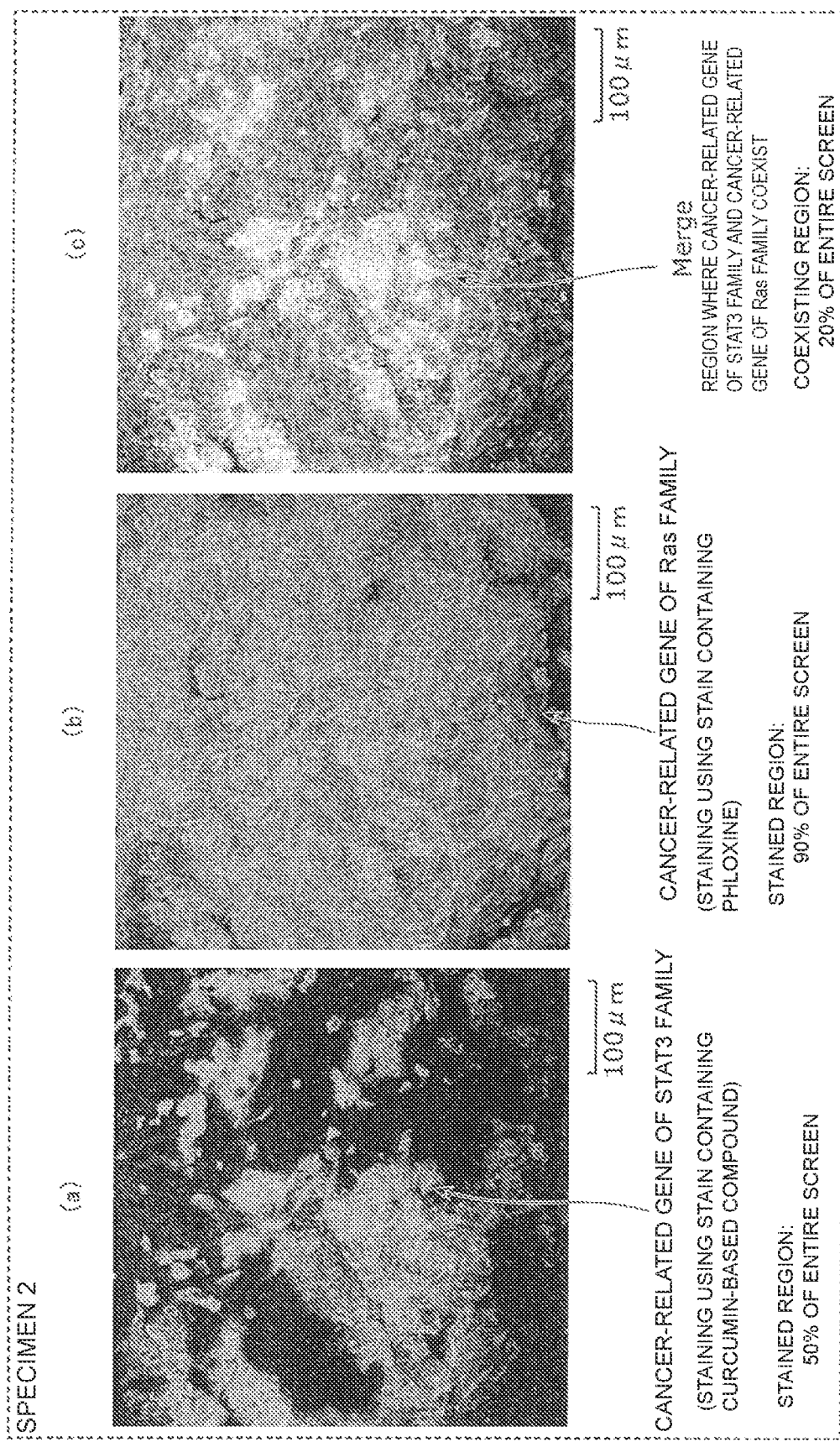
[Figure 2B]

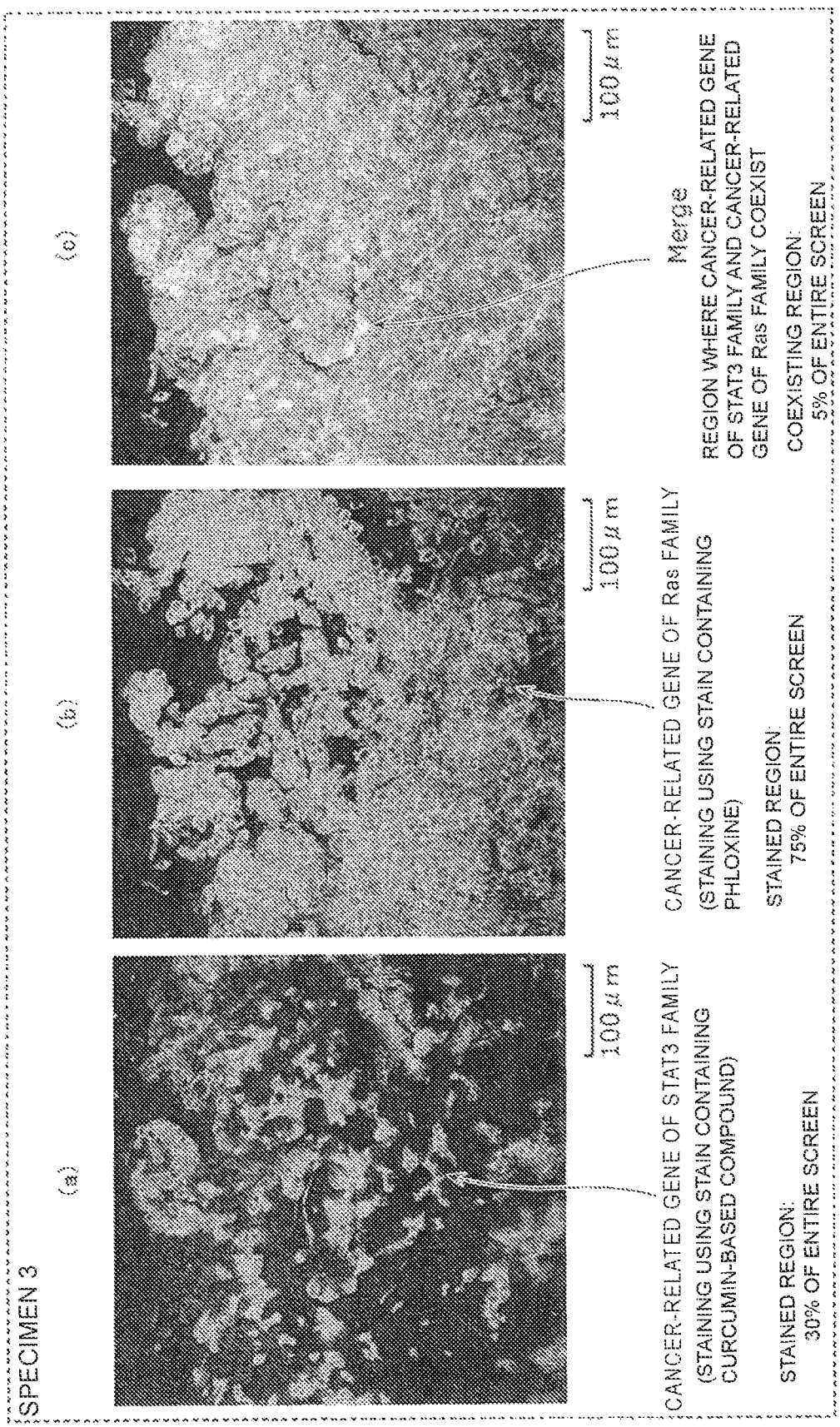

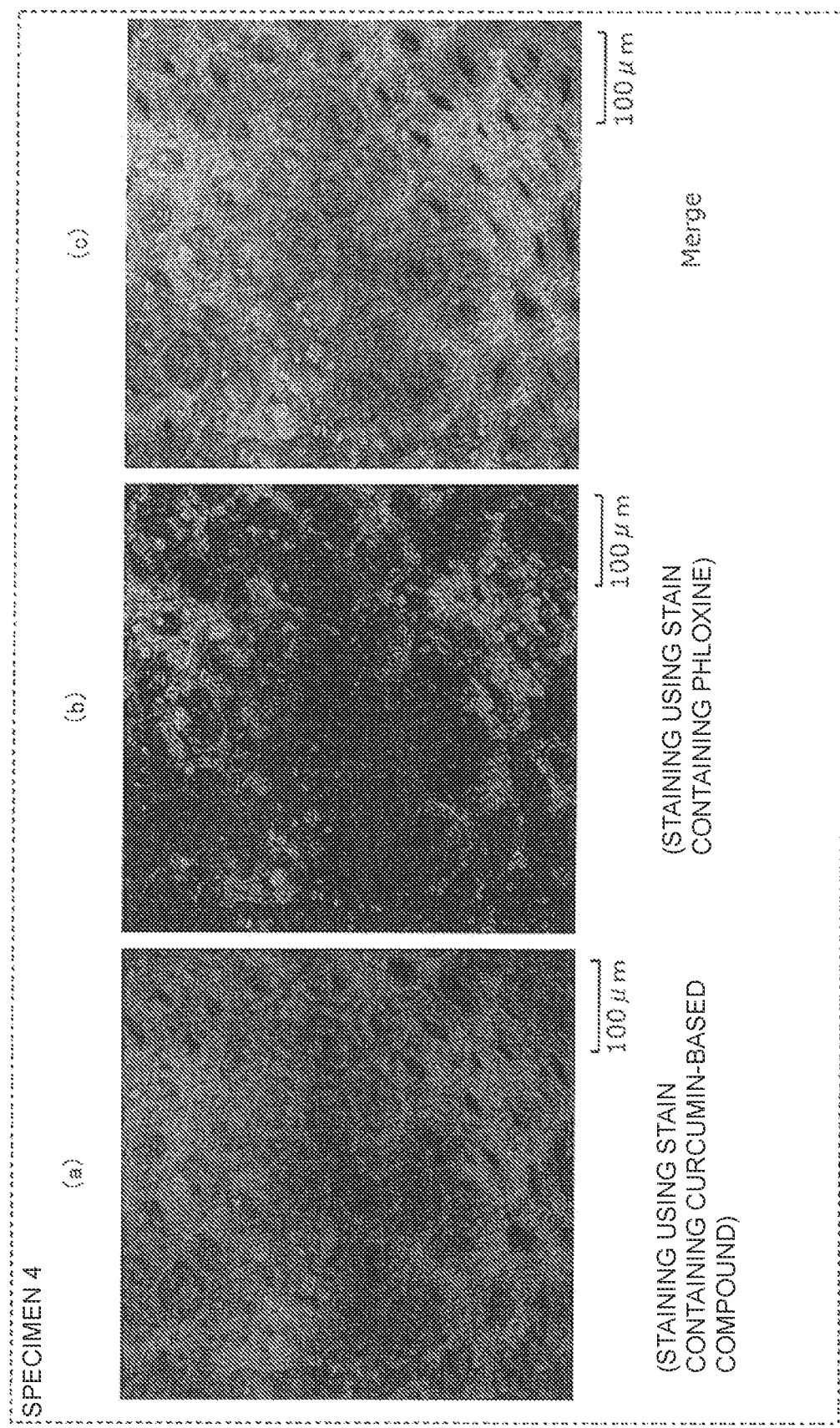

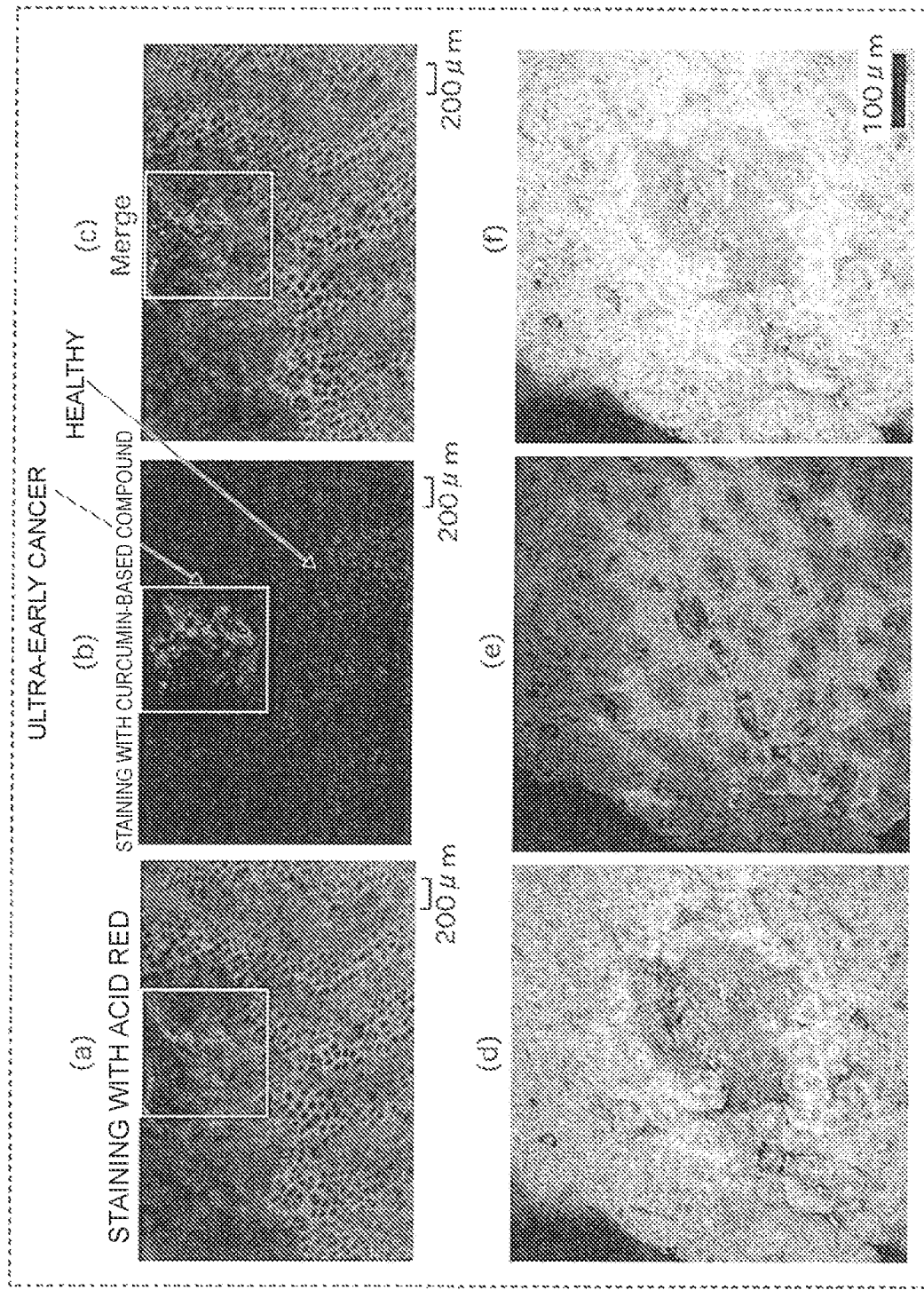
[Figure 4A]

[Figure 4B]
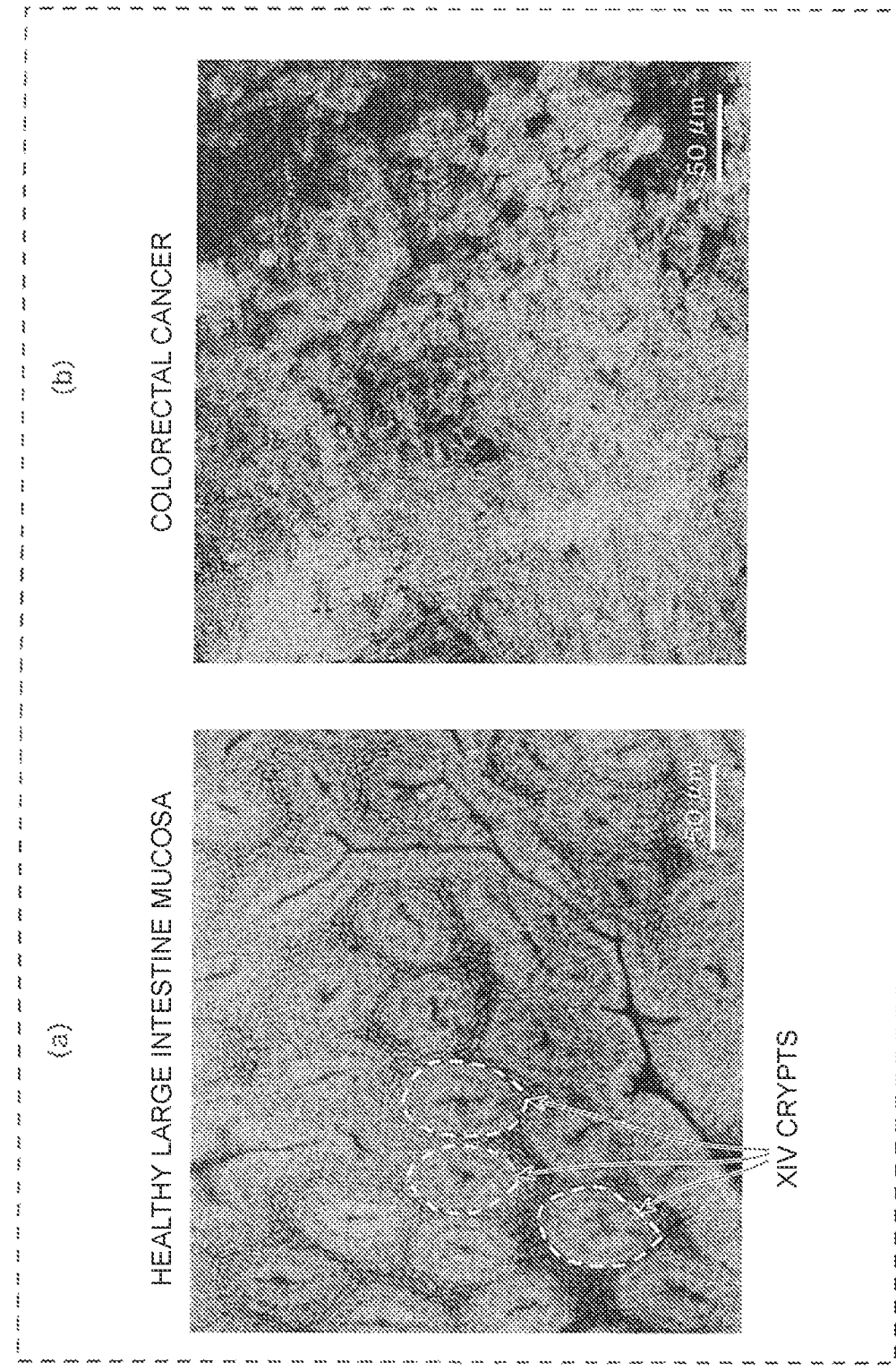

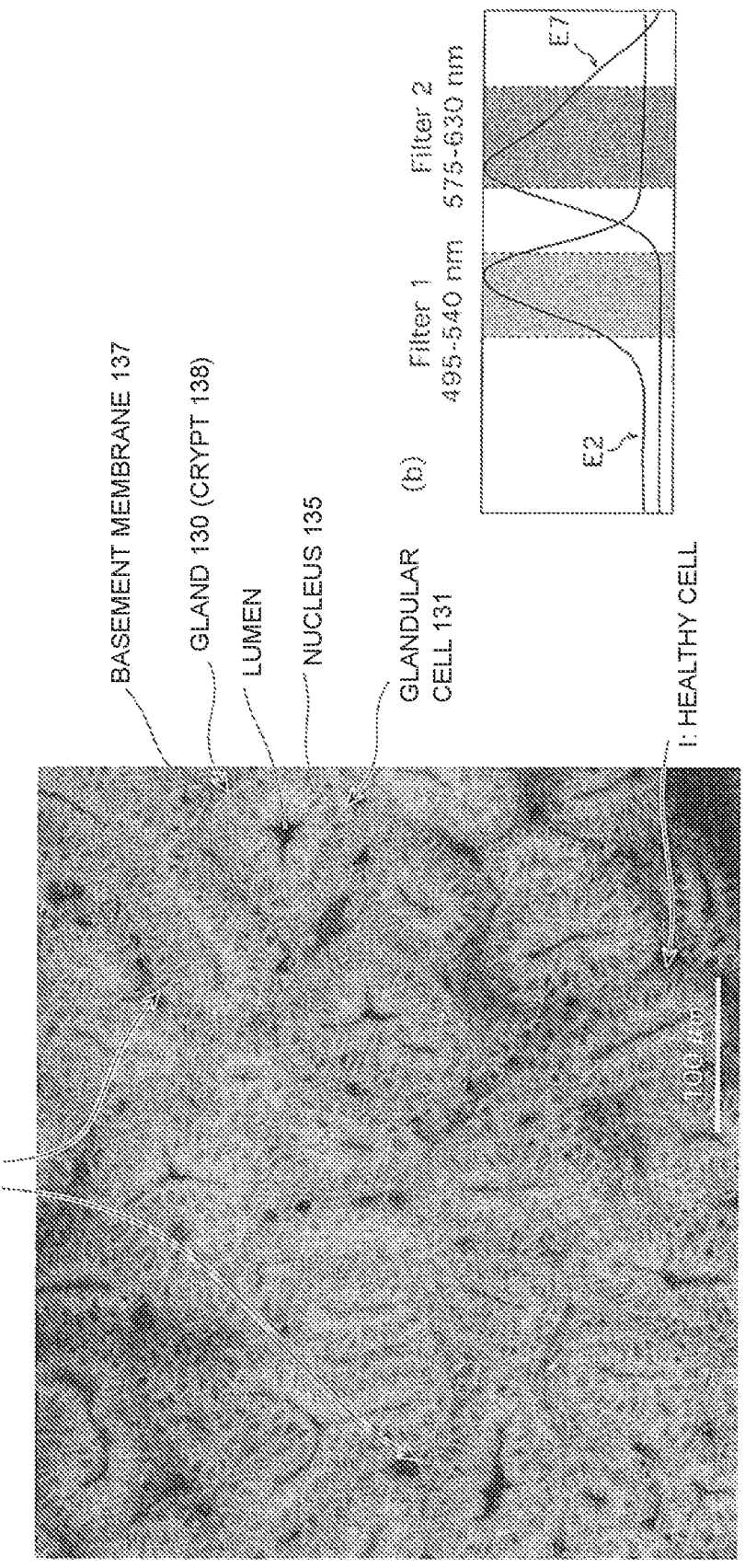
[Figure 4C]
STAINING WITH CURCUMIN DYE

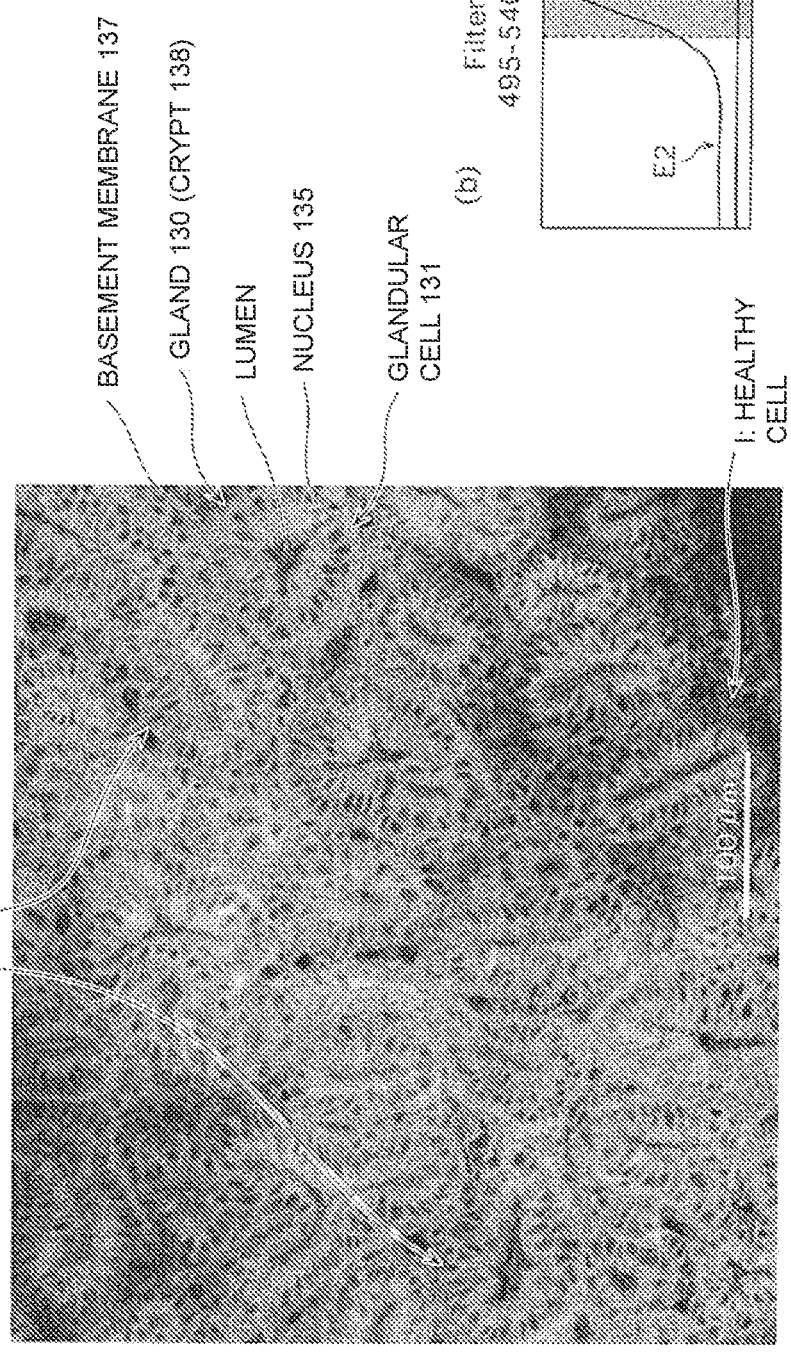
[Figure 4D] STAINING WITH CURCUMIN DYE AND ACID RED DYE

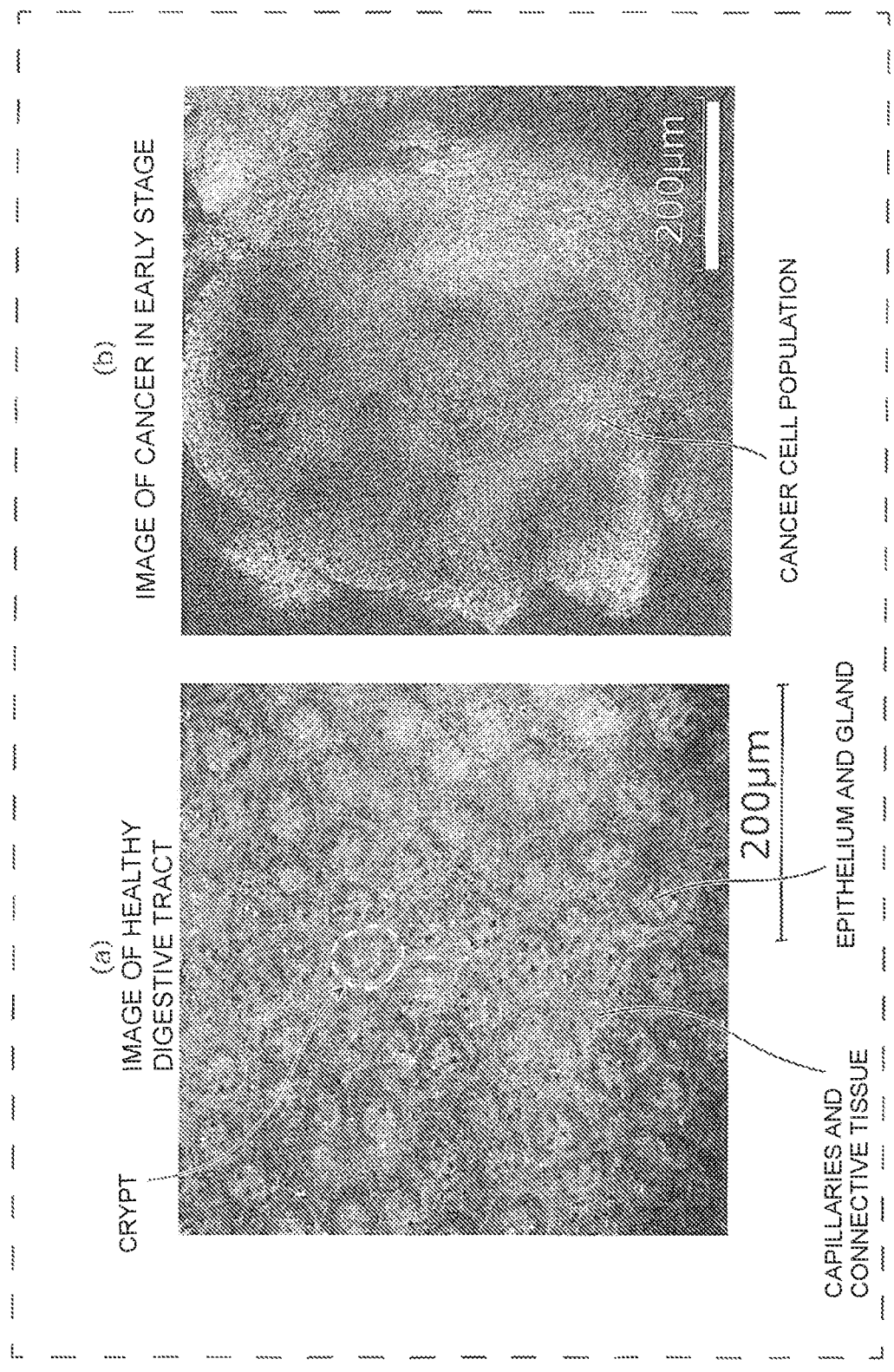
[Figure 4E]

[Figure 5A]
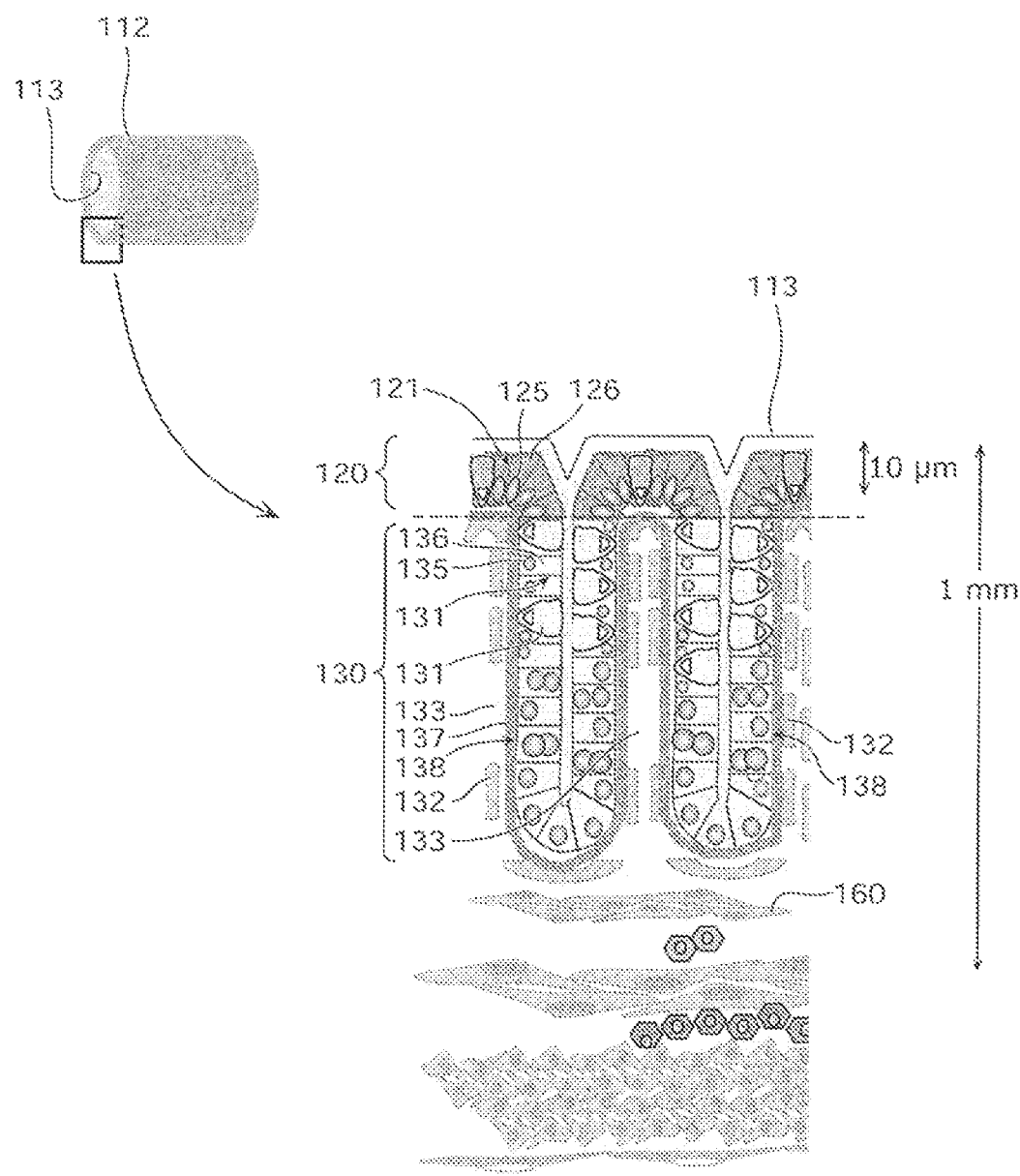

[Figure 5B]
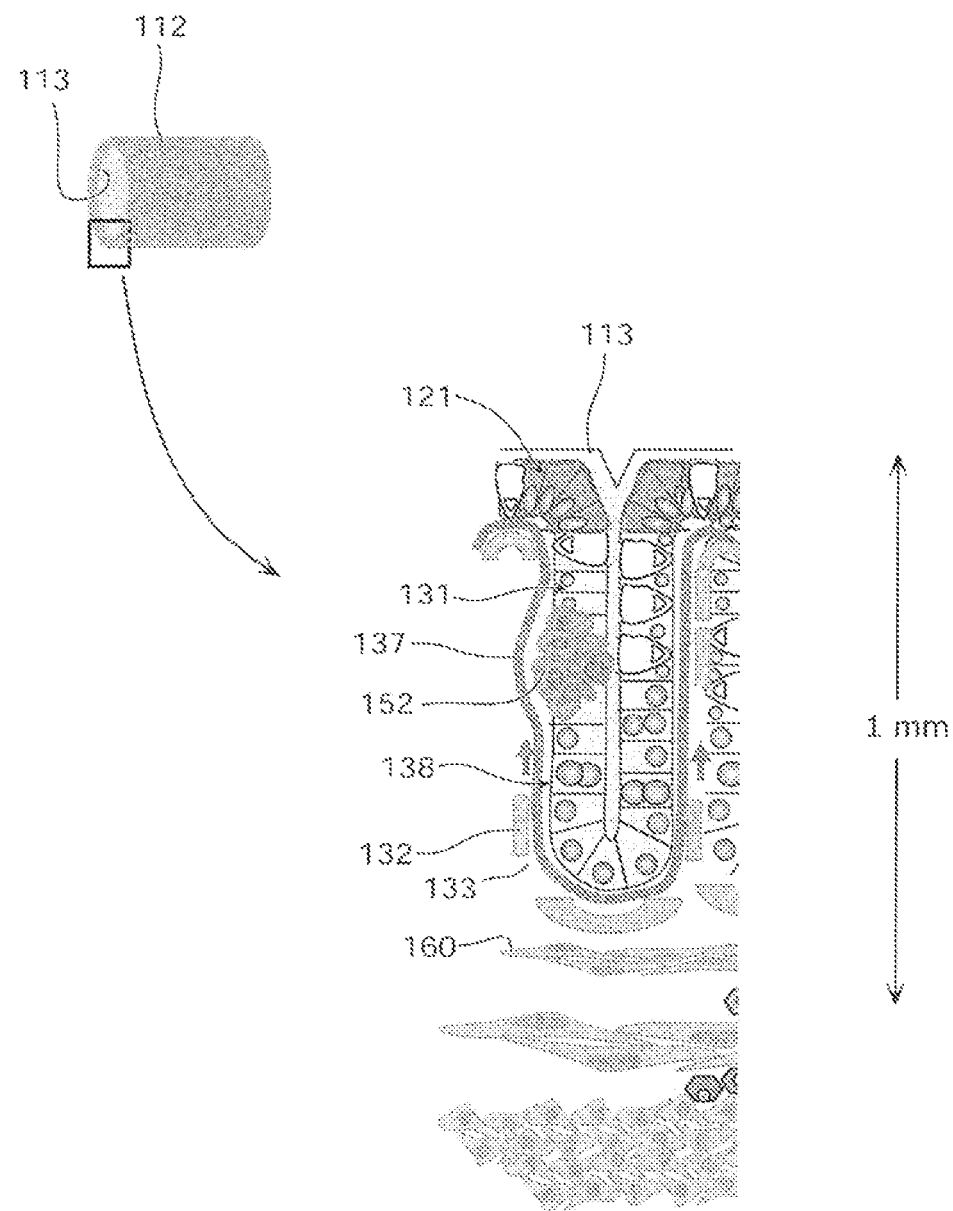

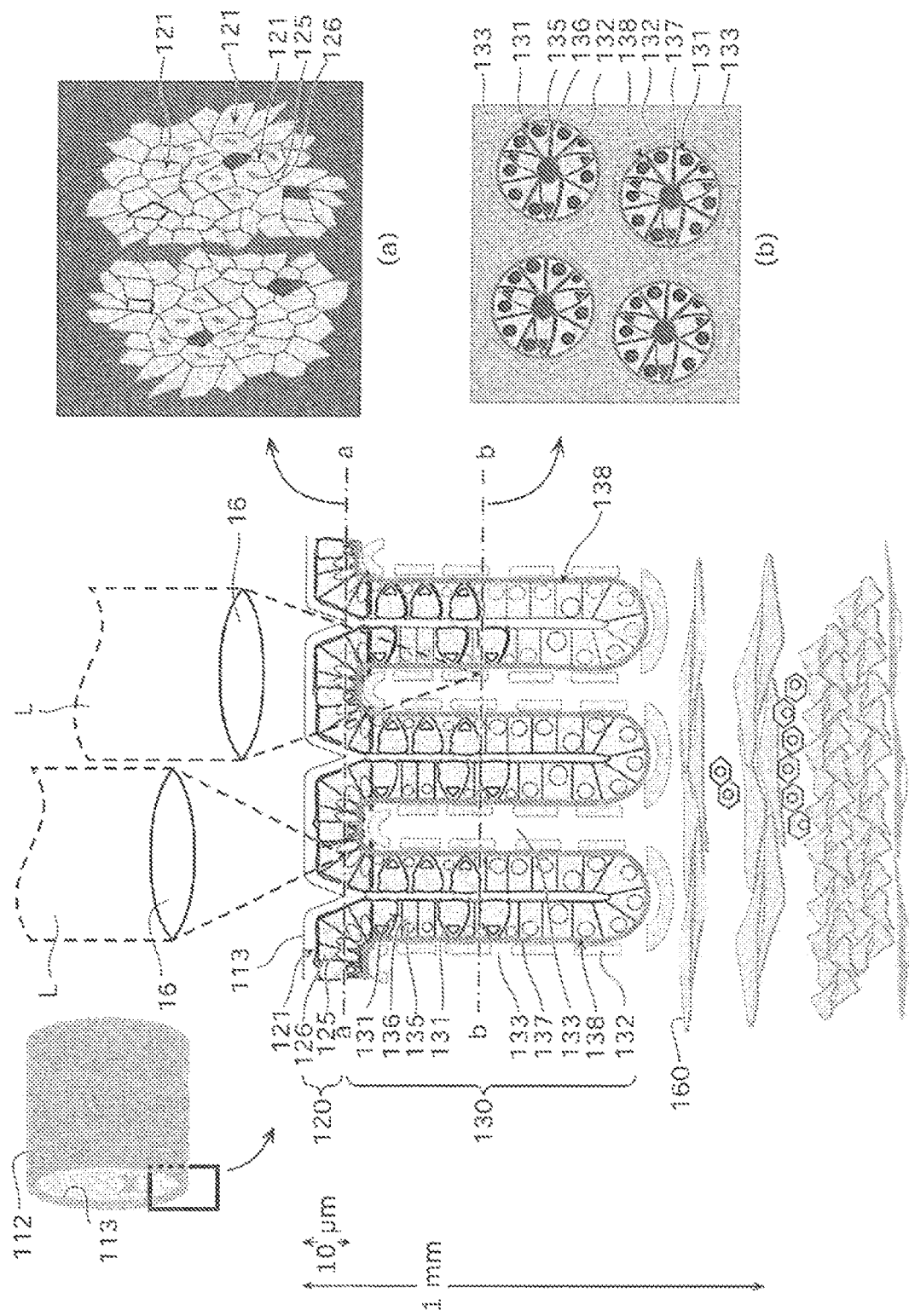

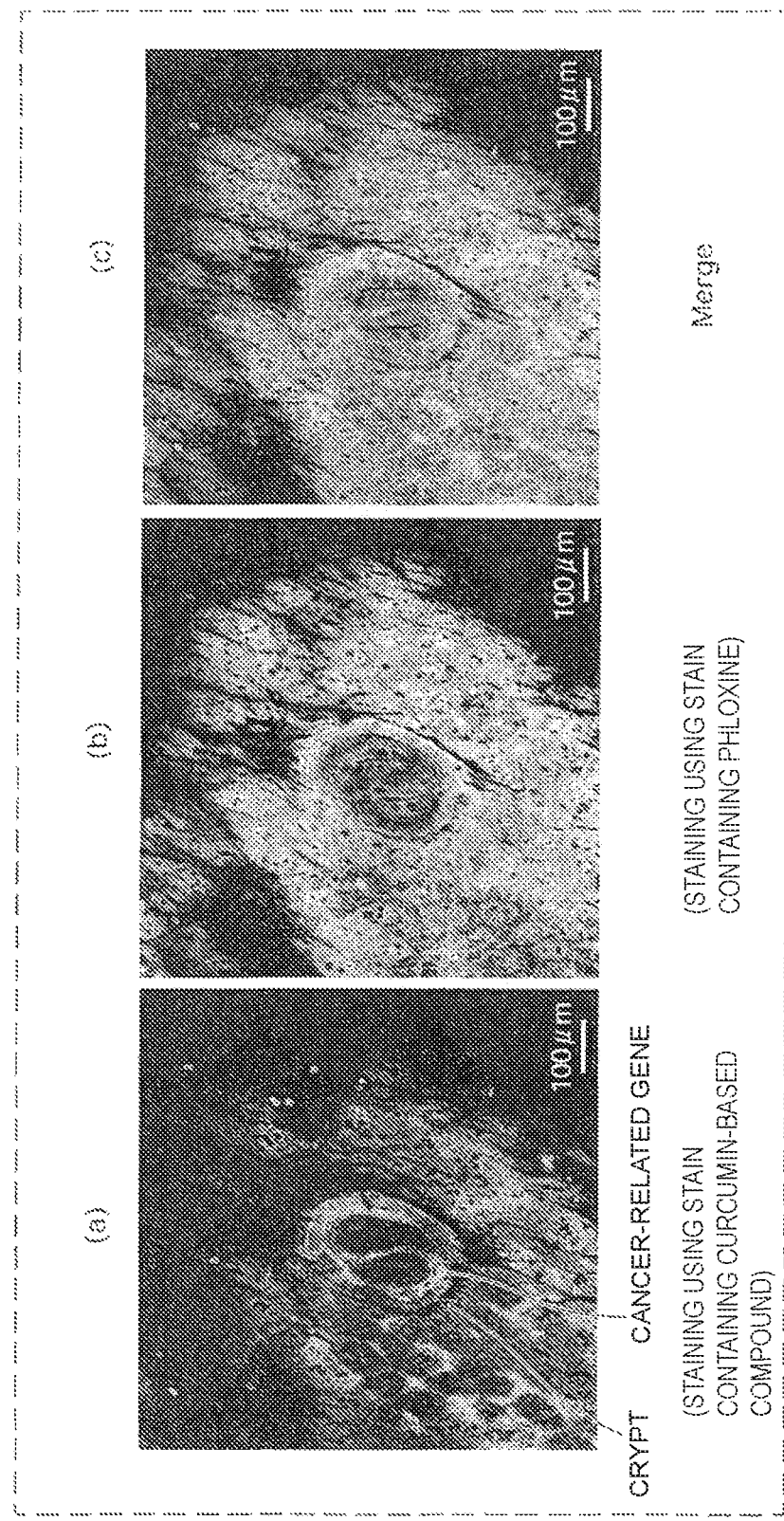
[Figure 6A]

[Figure 6B]
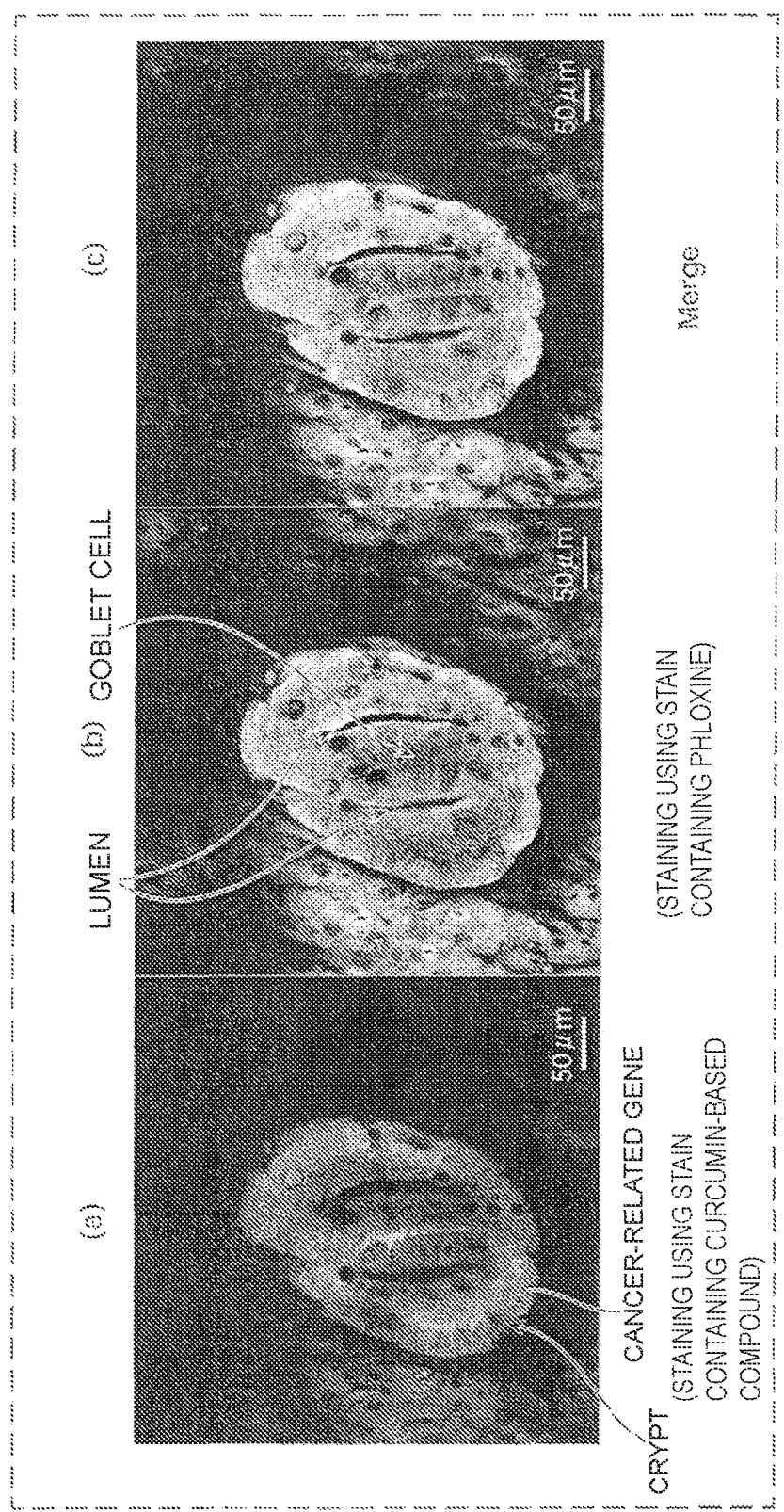

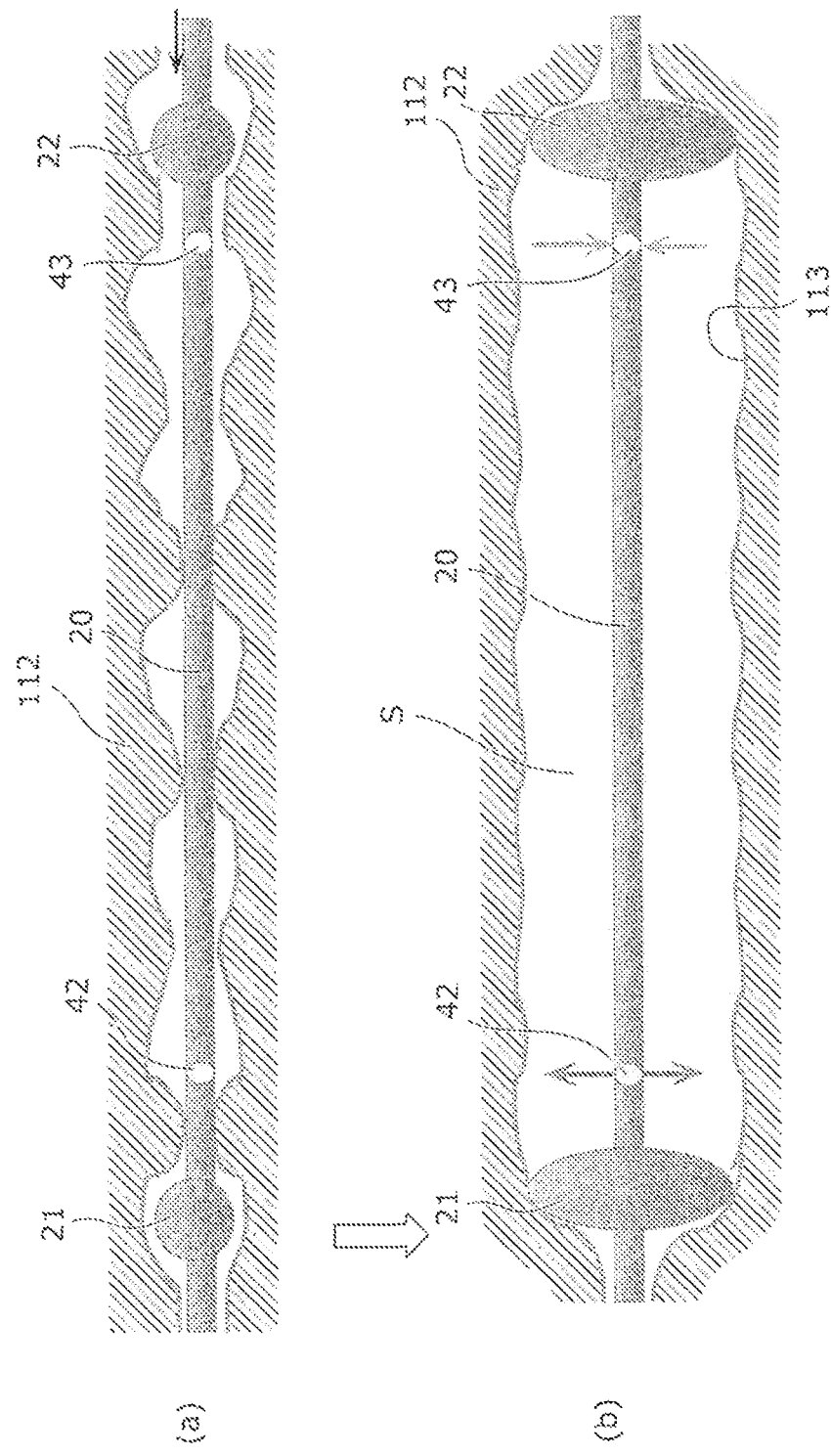
[Figure 7]

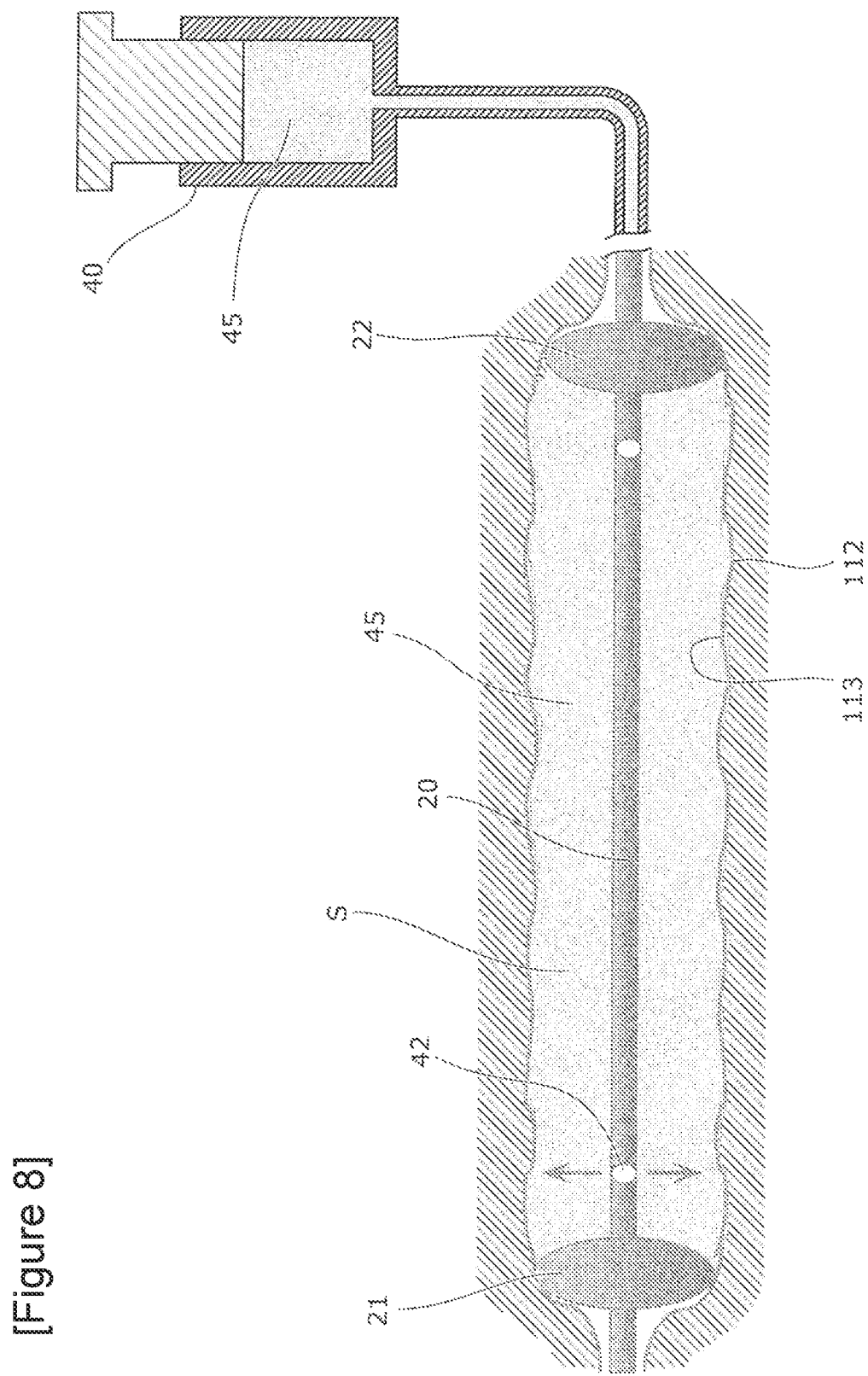
[Figure 8]

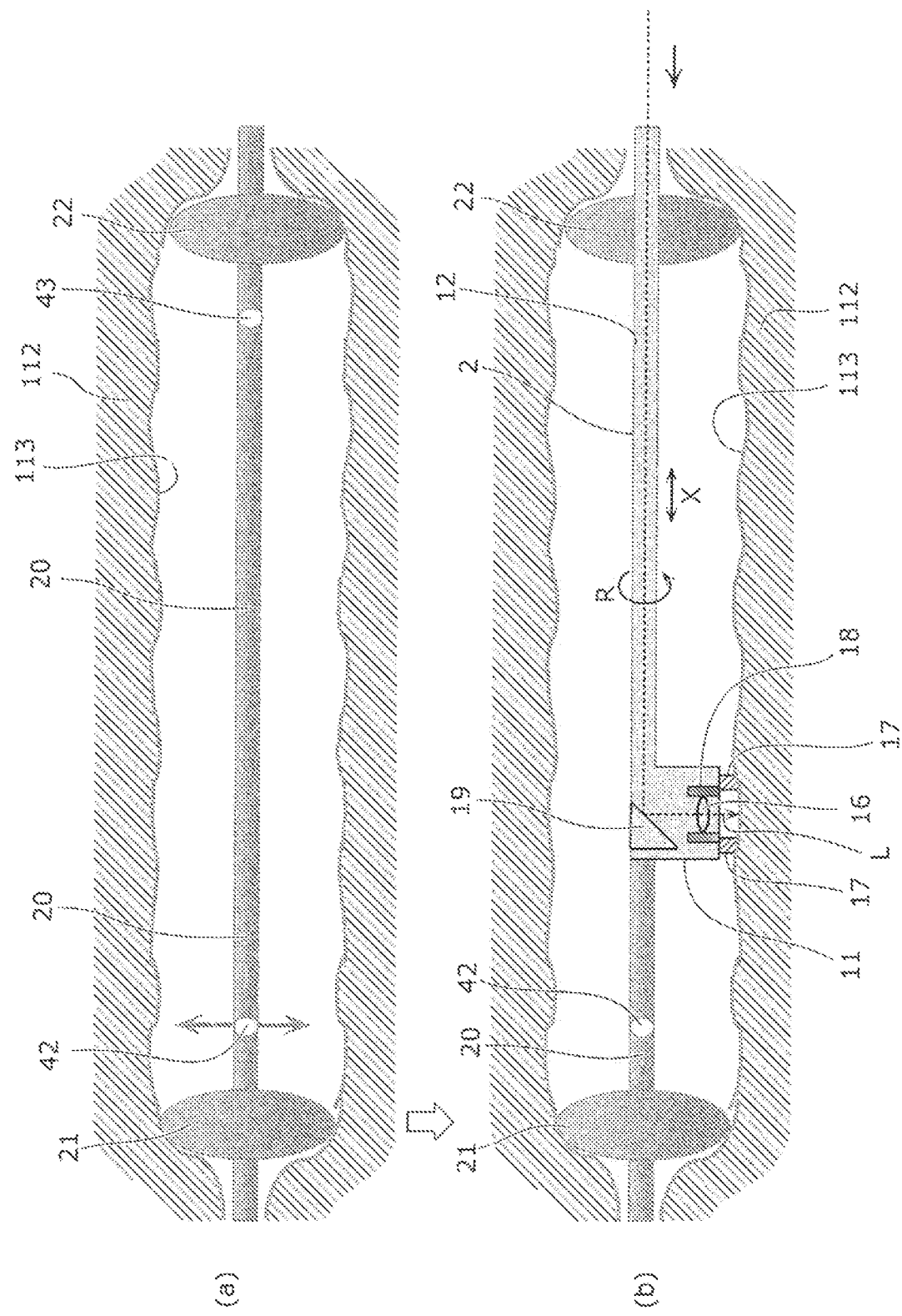

[Figure 10]
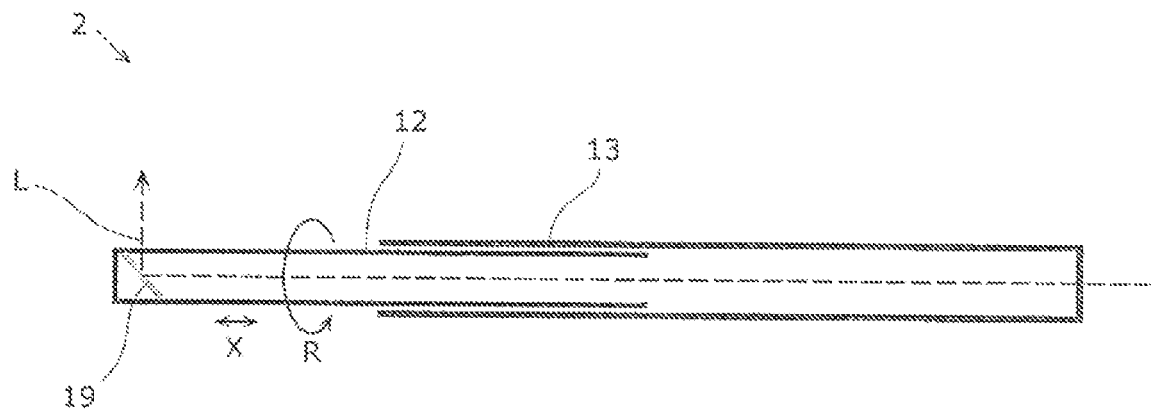
[Figure 11]
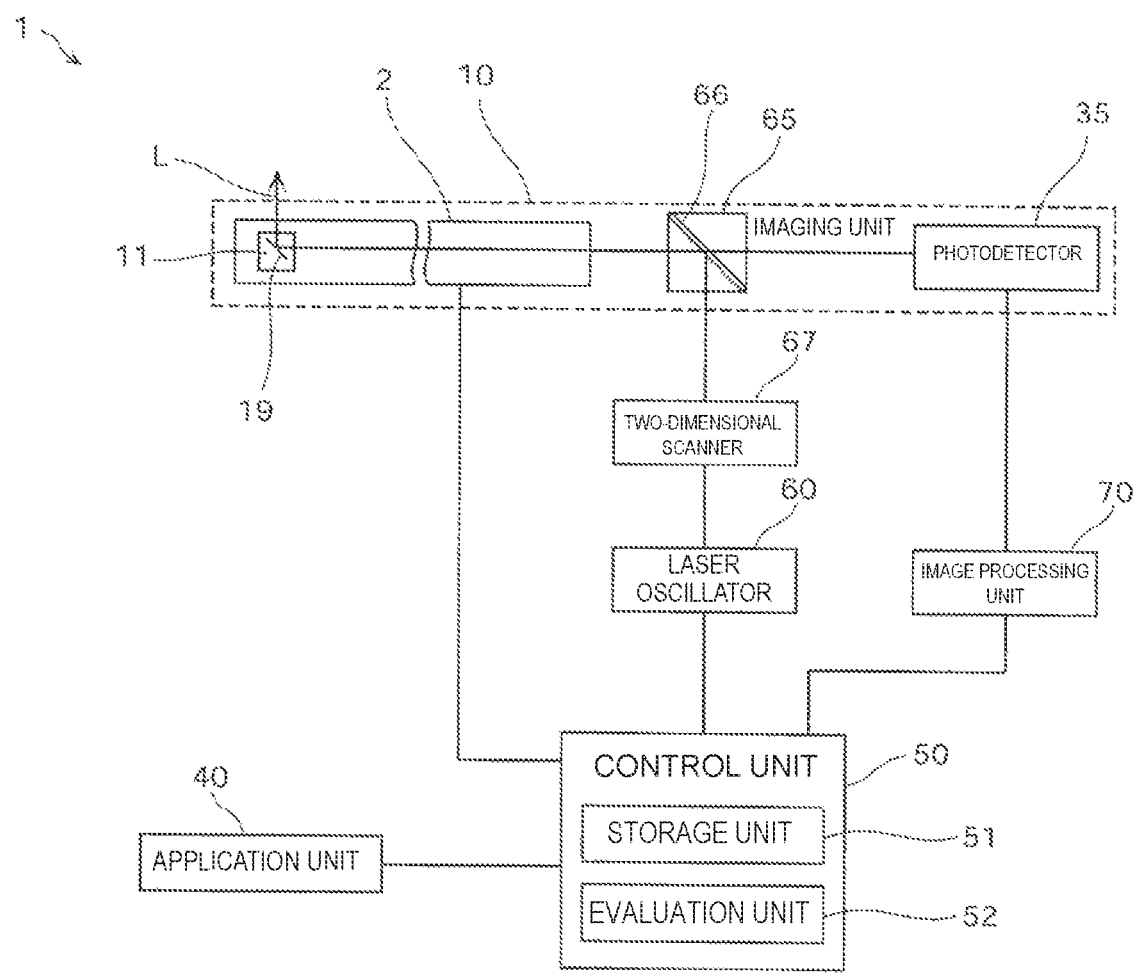

[Figure 12]
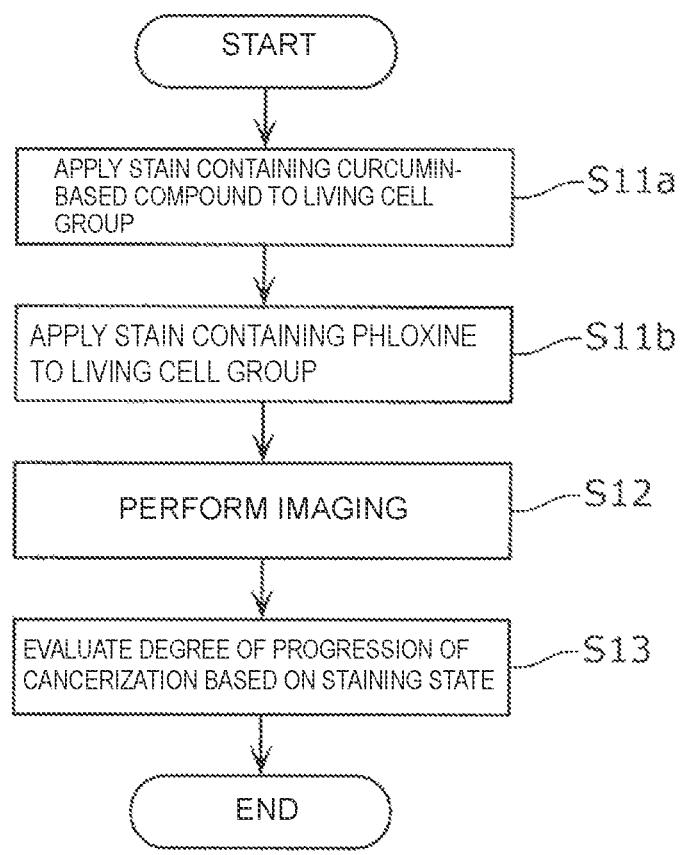

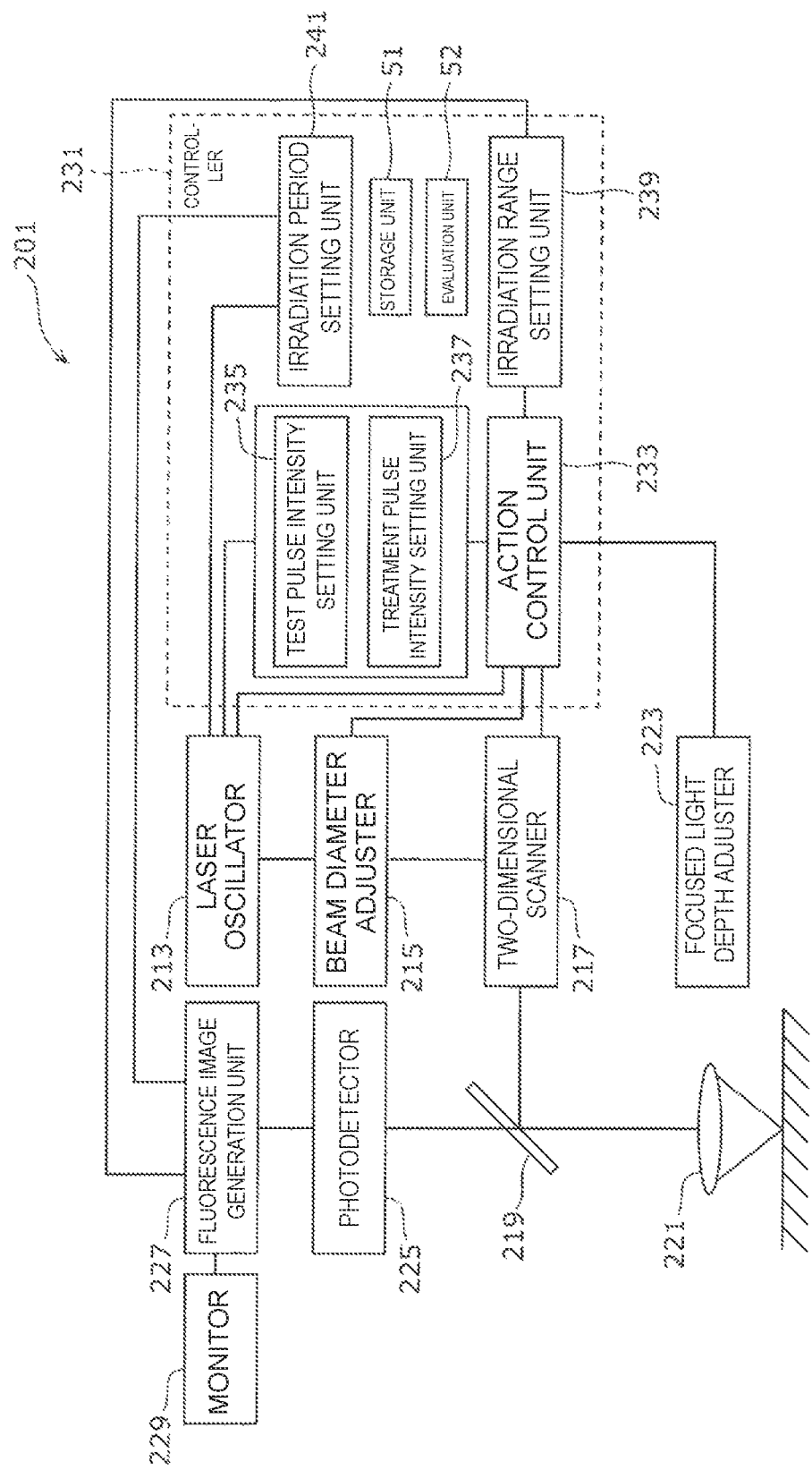
[Figure 13]

[Figure 14]
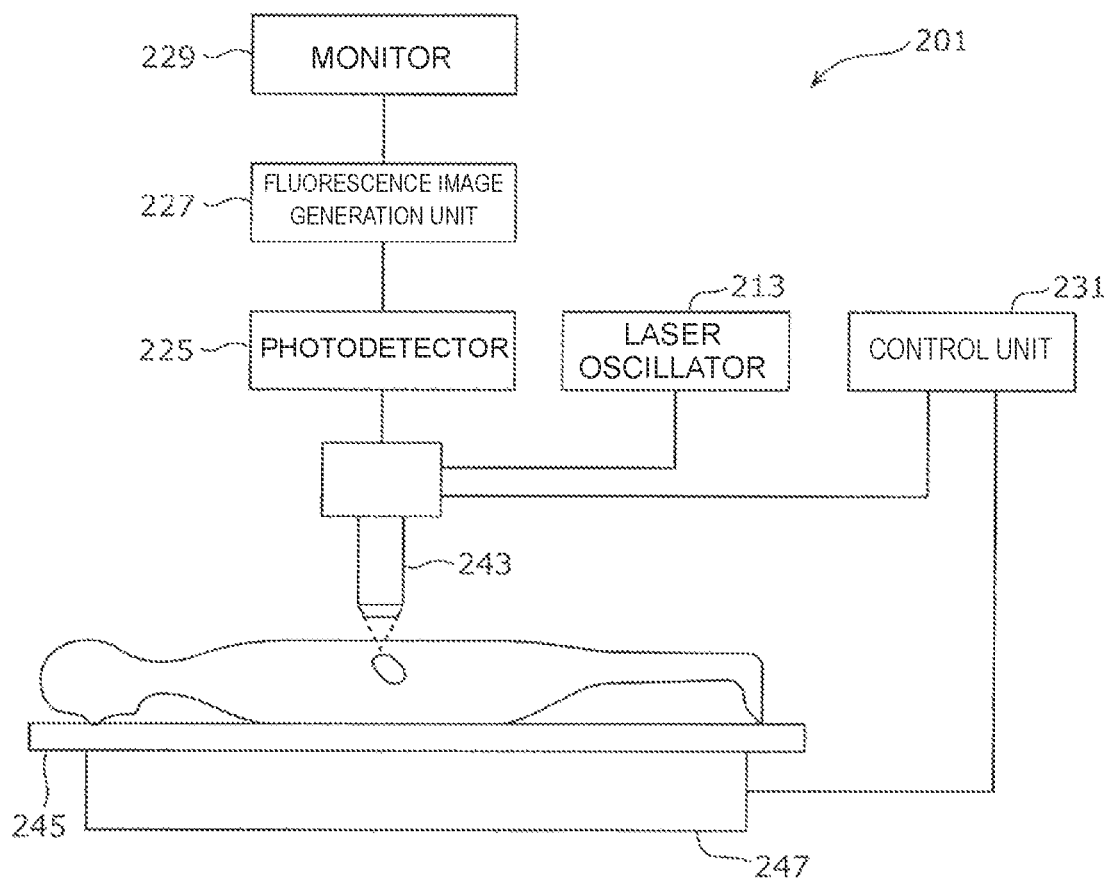

[Figure 16]
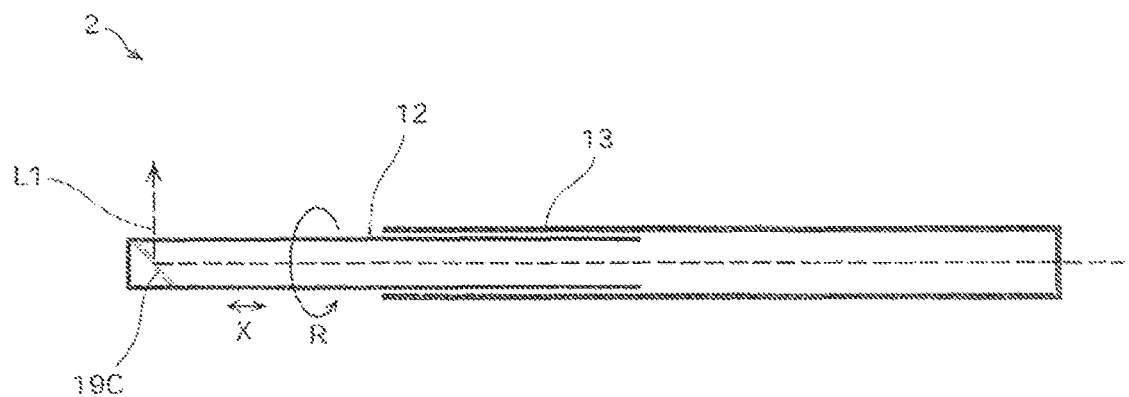
[Figure 17]
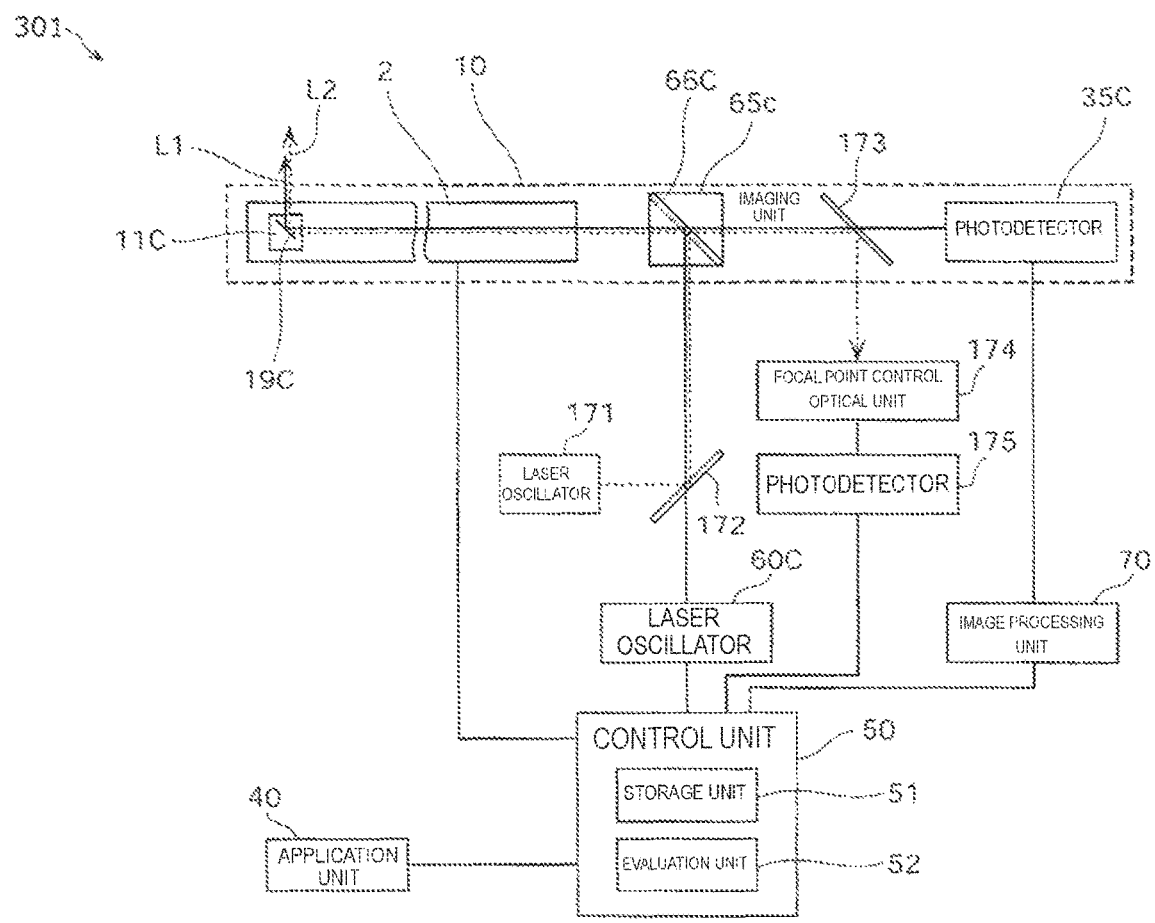

[Figure 18]
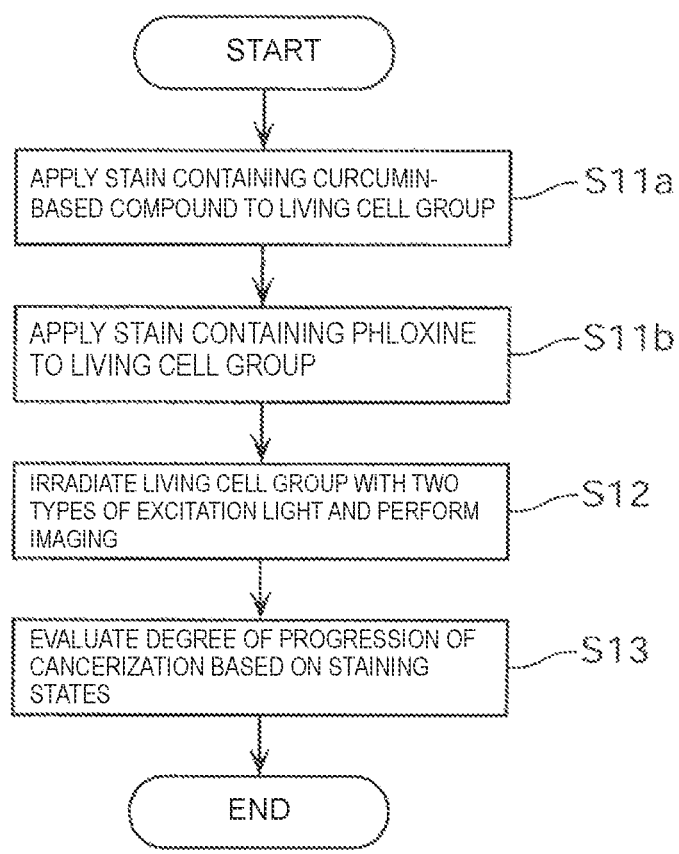

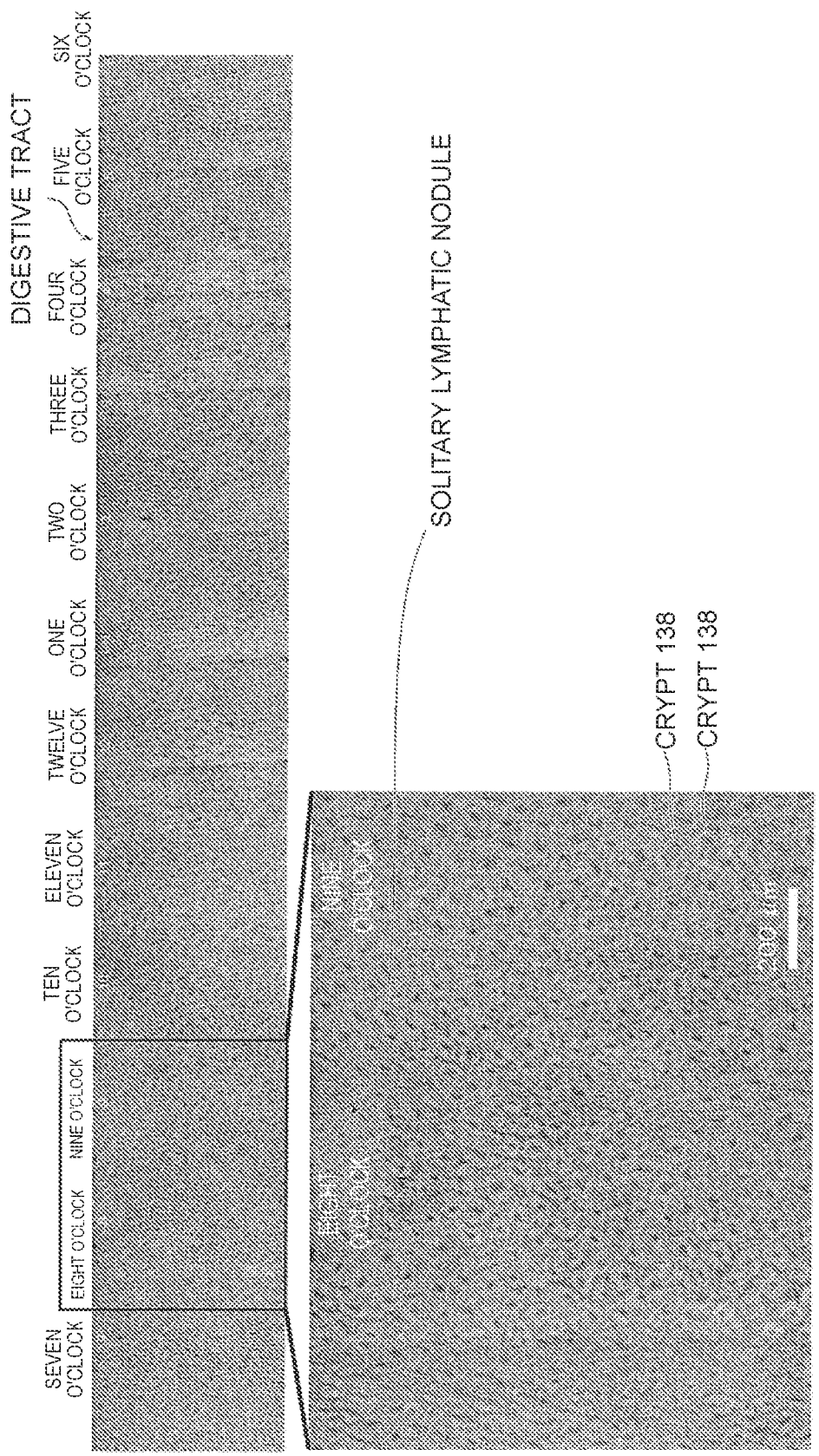
[Figure 19A]

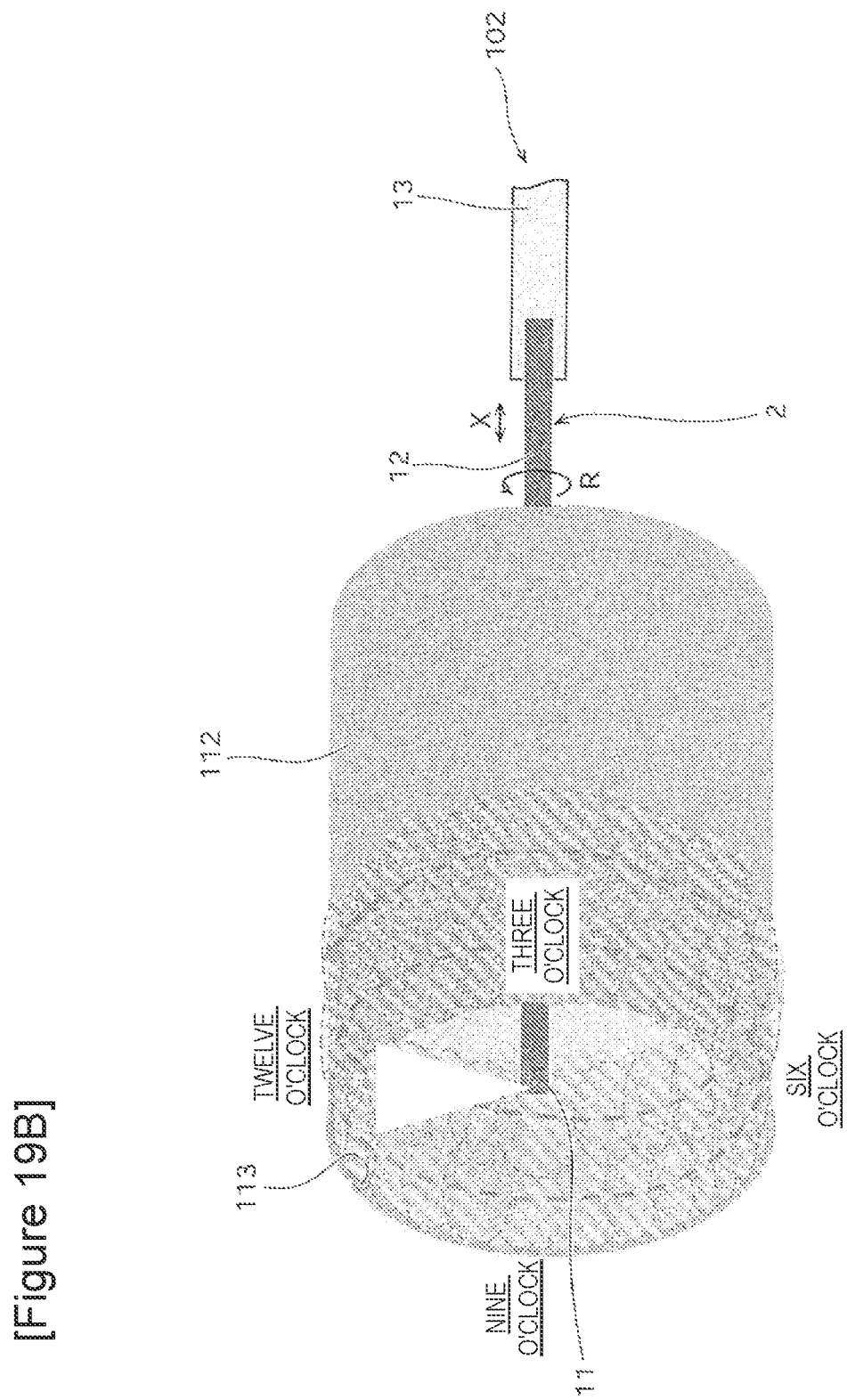
[Figure 19B]

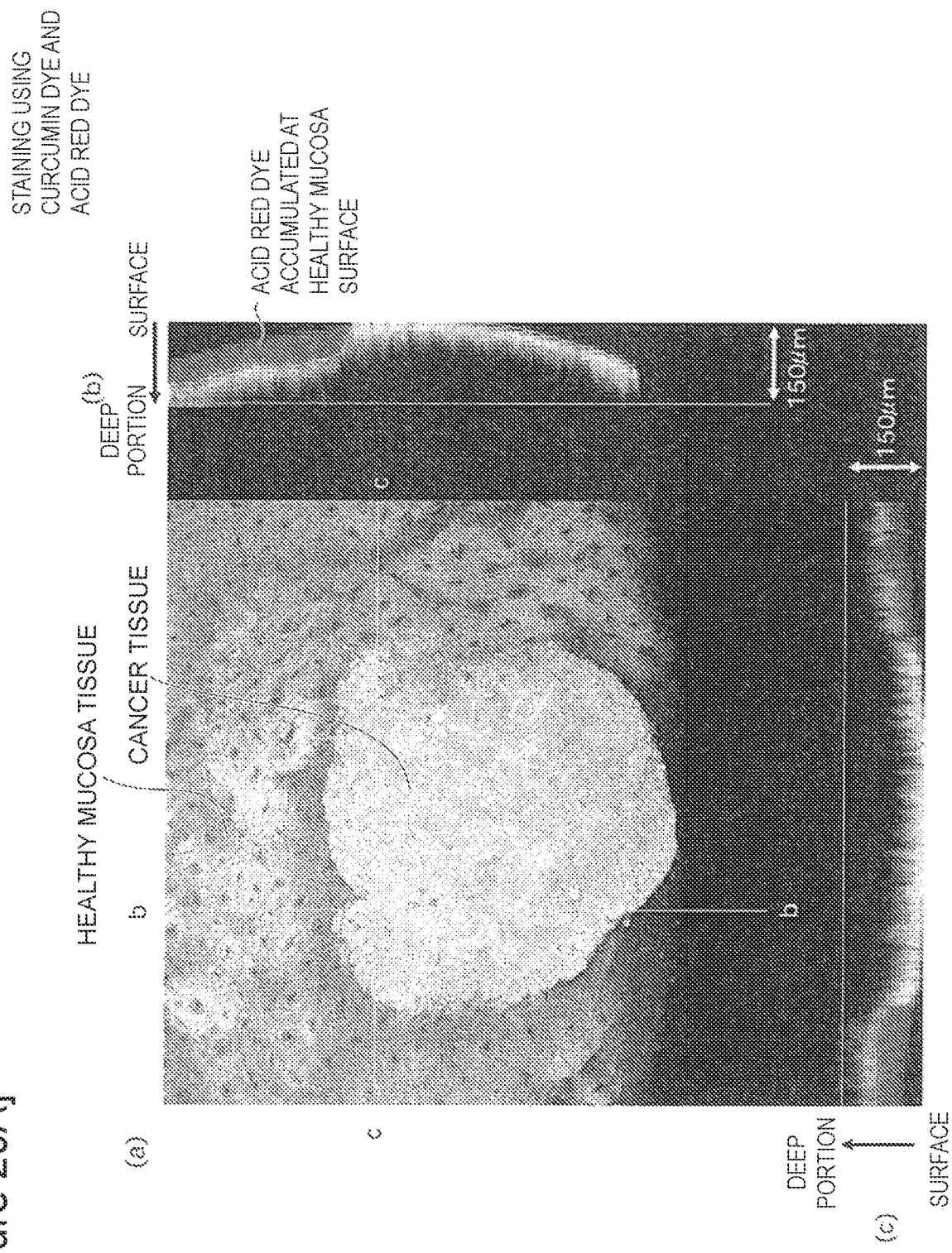
[Figure 20A]

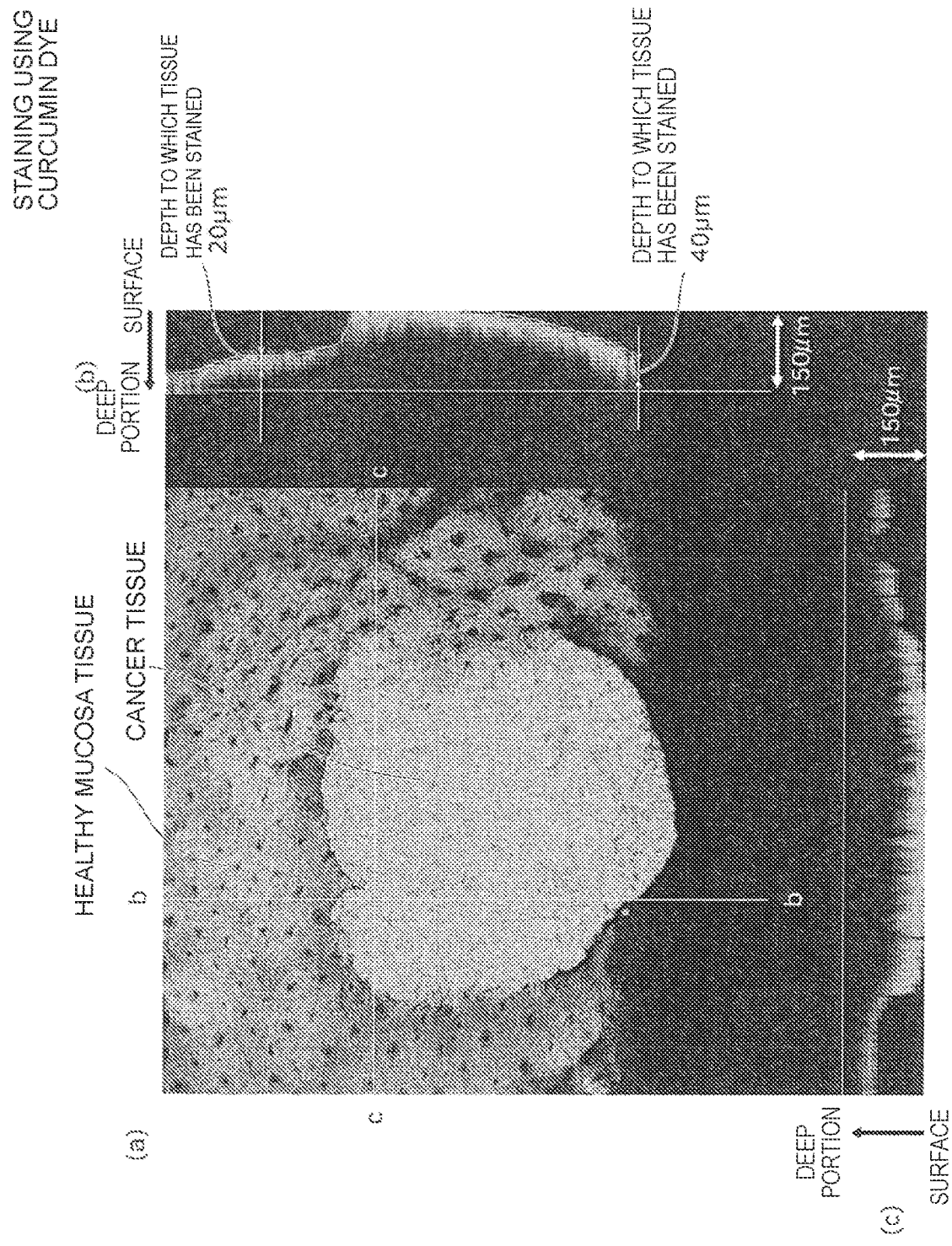
[Figure 20B]

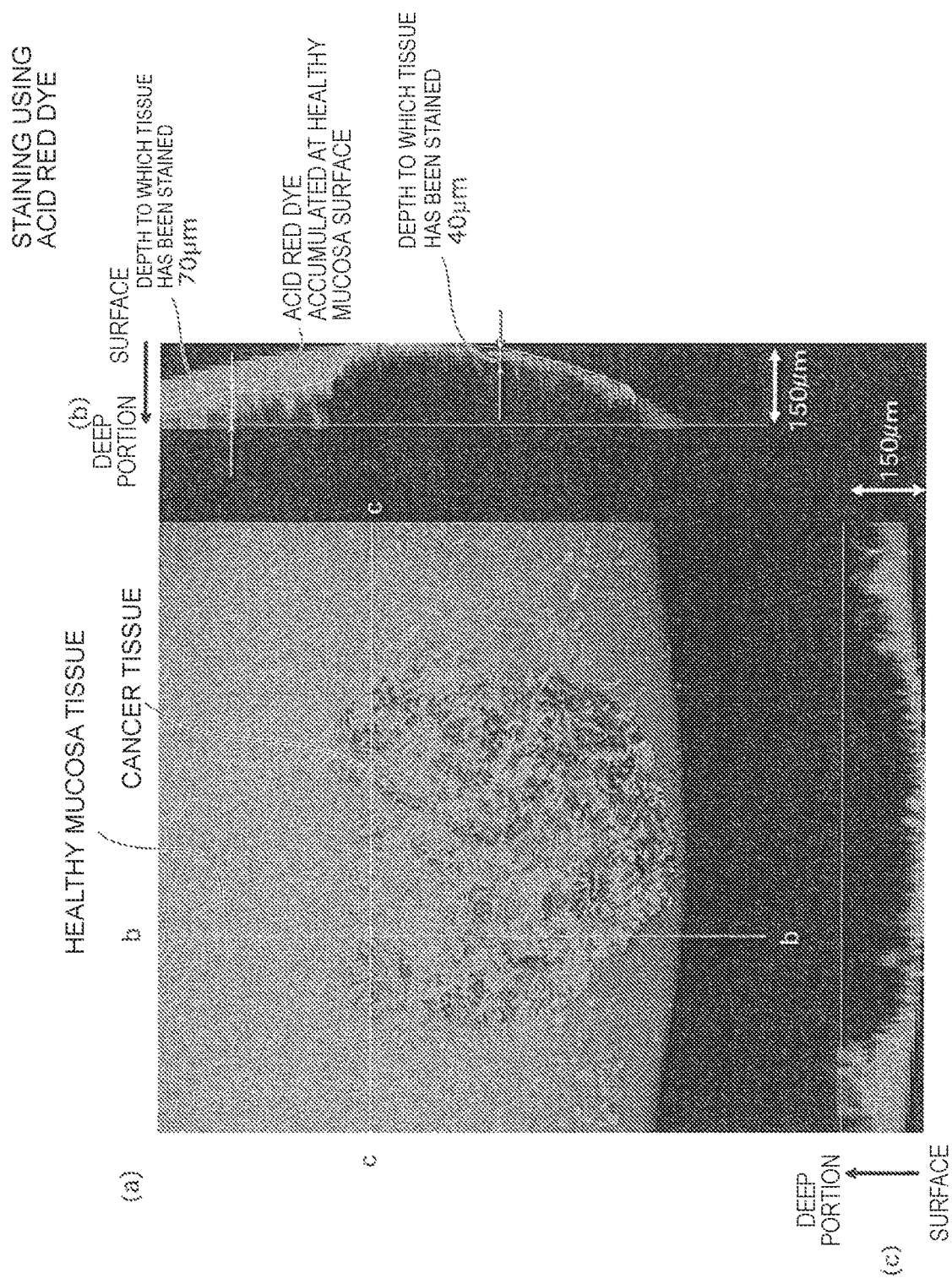
[Figure 20C]

CANCER TEST DEVICE, CANCER TEST METHOD, AND STAINING AGENT FOR USE IN CANCER TEST

TECHNICAL FIELD

The present invention relates to a cancer test device and a cancer test method for testing a cancerous living cell and a stain for use in a cancer test.

BACKGROUND ART

In recent years, as a method for checking a lesion in a living body (digestive tract, for example), there is a known method for imaging the form of a cell group in the living body to check whether or not a lesion, such as cancer cells, is present.

As an example of the method, Patent Literature 1 describes a method for staining a predetermined cell group in the living body in living body staining using a specific edible dye, such as curcumin and sulfuretin, and then applying multiphoton laser light to the stained cell group to readily detect the cancer cells because cancer cells are stained more heavily than healthy cells and further capture a fluorescence image of the individual cell forms in the living body. According to the method described above, since the cell group stained the living body emits fluorescence when the multiphoton laser light is applied thereto, a sharp image of the forms of the individual cells and nuclei in the living body can be generated. Whether or not a lesion, such as cancer cells, is present can therefore be precisely checked for pathological diagnosis.

CITATION LIST

Patent Literature

Patent Literature 1: International Publication No. WO 2014/157703

SUMMARY OF INVENTION

Technical Problem

The method described in Patent Literature 1 can be used to precisely check whether or not cancerization of a living cell has occurred. It is, however, required as a public requirement to grasp cancerization of a living cell as soon as possible.

The present invention achieves the requirement described above, and an object of the present invention is to provide a cancer test device and the like capable of grasping cancerization of a living cell in an early stage.

Solution to Problem

To achieve the object described above, a cancer test device according to an aspect of the present invention includes (1) an application unit that applies a stain to a living cell group, the stain selectively staining a cancer-related gene product of living cells in a chromatic color, (2) an imaging unit that images the living cell group to which the stain has been applied, and (3) an evaluation unit that evaluates, by the expression pattern, a grade of cancerization of the living cell group based on a staining state of the living cell group in an image produced by the imaging. A laser used in the imaging may be a multiphoton laser for a multiphoton laser microscope or a continuous-wave (CW) laser for a confocal laser microscope. The grade of cancerization used herein is so defined that a cancer cell having a high degree of the metastasis and infiltration capability, which the cancer cell inherently possesses, has a high grade of cancerization and cancer resistant to radiotherapy and chemotherapy has a high grade of cancerization.

According to the present aspect, the cancer test device evaluates the grade of cancerization based on the staining state of the cancer-related gene product of the living cell group, whereby cancerization of the living cell group can be grasped in an early stage. Further, since the grade of cancerization can be grasped, the prognosis of the cancer patient can be understood.

For example, the application unit may apply the stain that stains a ras-family cancer-related gene product that transmits a signal that promotes growth of the living cells.

Using the stain that stains the ras-family cancer-related gene product allows understanding of the tendency of the growth of the living cells, as in the present aspect, whereby development of cancer cells in the living cell group can be grasped in an early stage.

For example, the application unit may apply the stain containing phloxine, erythrosine, merbromin, fast green FCF, or meclocycline sulfosalicylate.

Using the stain shown in the present aspect allows staining of the ras-family cancer-related gene product, whereby development of cancer in the living cell group can be grasped in an early stage.

For example, the application unit may apply the stain that stains a STAT3-family cancer-related gene product that transmits a signal that promotes growth of the living cells.

Using the stain that stains the STAT3-family cancer-related gene product allows understanding of the tendency of the growth of the living cells, as in the present aspect, whereby development of cancer cells in the living cell group can be grasped in an early stage.

For example, the application unit may apply the stain containing a curcumin-based compound.

Using the stain shown in the present aspect allows staining of the STAT3-family cancer-related gene product, whereby development of cancer cells in the living cell group can be grasped in an early stage.

For example, the application unit may apply the stain containing a curcumin-based compound to the living cell group and then apply the stain containing phloxine, erythrosine, merbromin, fast green FCF, or meclocycline sulfosalicylate to the living cell group.

Applying the stain containing a curcumin-based compound before applying the stain containing phloxine, erythrosine, merbromin, fast green FCF, or meclocycline sulfosalicylate allows the contour of each of the cells and the shape of the nucleus in the cell to be clearly visualized, whereby a sharp image can be produced.

For example, the application unit may apply to the living cell group the stain that stains a STAT3-family cancer-related gene product that transmits a signal that promotes growth of the living cells and then apply the stain that stains a ras-family cancer-related gene product that transmits a signal that promotes growth of the living cells.

Applying the stain that stains the STAT3-family cancer-related gene product before applying the stain that stains the ras-family cancer-related gene product allows the STAT3-family cancer-related gene product to be clearly visualized, whereby a sharp image can be produced.

For example, the evaluation unit may perform the evaluation based on an area of a stained region of the living cell group.

According to the present aspect, the state of enhancement of expression of the cancer-related gene can be understood based on the area of the stained region, whereby the grade of cancerization can be precisely grasped.

For example, the evaluation unit may perform the evaluation based on the number of cells in a stained region of the living cell group.

According to the present aspect, the state of enhancement of expression of the cancer-related gene can be understood based on the number of cells in the stained region, whereby the grade of cancerization can be precisely grasped.

For example, the evaluation unit may perform the evaluation based on the number and average diameter of stained cell groups in a fixed area containing a stained region of the living cell group.

According to the present aspect, the state of enhancement of expression of the cancer-related gene can be understood based on the number and the average diameter of stained cell groups in the fixed area, whereby the grade of cancerization can be precisely grasped.

For example, the imaging unit may irradiate the living cell group to which the stain has been applied with multiphoton laser light or confocal laser light and image the living cell group.

Irradiating the living cell group with multiphoton laser light, as in the present aspect, allows the grade of cancerization to be readily grasped over the depth range greater than or equal to 10 μm but smaller than or equal to 1000 μm below the mucosa surface in the living body. Further, irradiating the living cell group with confocal laser light allows the grade of cancerization to be readily grasped over the depth range greater than or equal to 10 μm but smaller than or equal to 70 μm below the mucosa surface in the living body. The prognosis of the cancer patient can therefore be understood in an ultra-early stage before a cancer cell population appears on the mucosa surface.

For example, the imaging unit may image the cancer-related gene expression pattern of the cell population stained with the stain and having a diameter greater than or equal to 0.1 mm but smaller than or equal to 0.4 mm.

According to the present aspect, the grade of cancerization of the living cells in a pre-cancer state can be grasped, whereby the prognosis of the cancer patient can be understood in an early stage before a cancer cell population clearly manifests.

For example, the application unit may apply a plurality of different stains to the living cell group to stain a plurality of cancer-related gene products in colors different from one another, and the imaging unit may irradiate the plurality of cancer-related gene expression patterns stained in the different colors with a plurality of excitation light beams according to the stains and image the plurality of cancer-related gene expression patterns.

Irradiating the plurality of stained cancer-related gene expression patterns with the plurality of excitation light beams according to the stains allows precise detection of the plurality of cancer-related gene expression patterns.

For example, the stains may be formed of at least two types of stain, and the excitation light beams with which the plurality of cancer-related gene expression patterns are irradiated may be selected in correspondence with the types of the stain.

Using at least two types of stain and irradiating the plurality of cancer-related gene expression patterns with excitation light beams corresponding to the stains allows detection of at least two cancer-related gene expression patterns. Detecting the many cancer-related gene expression patterns as described above allows the grade of cancerization to be grasped from diverse viewpoints.

For example, the imaging unit may include a focal point position control unit and control the focal point position control unit to image the cancer-related gene expression pattern present over the depth range greater than or equal to 10 μm but smaller than or equal to 1000 below a surface in the living body stained with the stain.

According to the present aspect, the grade of cancerization of the interior of the living body over the depth range greater than or equal to 10 μm but smaller than or equal to 1000 μm below the mucosa surface can be grasped, whereby the prognosis of the cancer patient can be understood in an early stage before a cancer cell population appears on the mucosa surface.

For example, the focal point position control unit may be controlled to change a focal point at fixed intervals from the surface in the same imaging position in the living body stained with the stain to perform imaging at different-depth focal point positions, a plurality of captured images may be superimposed on each other in a focal point position information order into a stereoscopic image, and the evaluation may be performed based on a degree of penetration of the stain in the stereoscopic image.

According to the present aspect, the grade of cancerization of the interior of the living body can be grasped based on the degree of penetration of the stain in the stereoscopic image, whereby the prognosis of the cancer patient can be understood in an ultra-early stage before a cancer cell population appears on the mucosa surface.

A cancer test method according to another aspect of the present invention includes an application step of applying a stain to a living cell group, the stain selectively staining a cancer-related gene product of living cells in a chromatic color, an imaging step of imaging the living cell group to which the stain has been applied, and an evaluation step of evaluating a grade of cancerization of the living cell group based on a staining state of the living cell group in an image produced by the imaging.

According to the present aspect, the cancer test method evaluates the grade of cancerization based on the staining state of the cancer-related gene expression pattern of the living cell group, whereby cancerization of the living cell group can be grasped in an early stage. Further, since the grade of cancerization can be grasped, the prognosis of the cancer patient can be understood.

A stain for a cancer test according to another aspect of the present invention contains phloxine, erythrosine, merbromin, fast green FCF, or meclocycline sulfosalicylate, which stains a ras-family cancer-related gene product that transmits a signal that promotes growth of living cells, or a curcumin-based compound, which stains a STAT3-family cancer-related gene product that transmits a signal that promotes growth of the living cells, and the stain has a concentration that allows the stain to penetrate into a cytoplasm of the living cells within 10 minutes after the staining starts but does not penetrate into a nucleus of the cells.

Since the stain for a cancer test according to the present aspect penetrates into the cytoplasm but does not penetrate into the nucleus of the cells as long as the period having elapsed since the staining started is 10 minutes or shorter, the nucleus surrounded by the cytoplasm can be sharply visualized, whereby analysis of cancerization can be more distinctly performed.

Advantageous Effects of Invention

According to the present invention, cancerization of living cell can be grasped in a very early stage at which a cancerous portion has a diameter of about 1 mm or in an ultra-early stage.

Further, according to the primary configuration of the present invention, the expression pattern of a cancer-related gene can be analyzed, whereby the degree of risk that a cancer tumor affects the patient (vital prognosis) can be determined.

The observation target described above only includes the epithelial cells, the glandular cells, connective tissue, and capillaries in the mucosa surface on the inner wall of a digestive tract of a living body. Instead, fresh tissue within 20 minutes immediately after the tissue is surgically excised can be used as the observation material to image a cell form image similar to an image of living tissue.

BRIEF DESCRIPTION OF DRAWINGS

FIG. 1A is a diagrammatic view showing a state in which cancer-related gene products in a living cell act normally.

FIG. 1B is a diagrammatic view showing a state in which the cancer-related gene products in the living cell act abnormally. The cross star marks in FIG. 1B each indicate cancerous mutation that occurs in the corresponding cancer-related gene product.

FIG. 1C is a diagrammatic view showing a stepwise cancerization process of a living cell group on the inner wall surface of a digestive tract.

FIG. 1D shows an example of a human cancer cell growth curve.

FIG. 2A shows images of a cancer-related gene expression pattern of living cells associated with a specimen 1: The section (a) shows an image of an STAT3 cancer-related gene expression pattern stained with curcumin; the section (b) shows an image of a ras-family cancer-related gene expression pattern stained with phloxine; and the section (c) is an (a)+(b) superimposed image.

FIG. 2B shows images of a cancer-related gene expression pattern of living cells associated with a specimen 2, and the images are shown in the same manner as those in FIG. 2A.

FIG. 2C shows images of a cancer-related gene expression pattern of living cells associated with a specimen 3, and the images are shown in the same manner as those in FIG. 2A.

FIG. 3 shows images of a group of healthy living cells associated with a specimen 4.

FIG. 4A shows three panels (a), (b), and (c) in the upper row of showing the result of operation of double-staining the inner wall of a large intestine of a digestive tract of a laboratory mouse with a stain containing Acid Red and a stain containing a curcumin-based compound in living body staining, capturing cell images at the surface of the inner wall of the digestive tract and in the interior of the living body over the range from the surface to a depth of about 30 μm with a confocal laser microscope, and digitizing the images. The section (a) shows an image of the cells stained in living body staining using the stain containing Acid Red. The section (b) shows an image of the cells stained in living body staining using the stain containing a curcumin-based compound. The section (c) is an (a)+(b) superimposed image. The three panels (d), (e), and (f) in the lower row show images of the same site of the large intestine of the digestive tract of the laboratory mouse stained in the same living body staining as that in the upper row, fixed with formalin, and then imaged in the fluorescence antibody technique. The section (d) shows that intracellular actin filaments are visualized with Alexa-488-labeled phalloidin. The section (e) shows that the intracellular actin filaments are stained with anti-STAT3 antibody and Alexa-594-labeled secondary antibody at the same time so that the distribution of a cancer-related gene product STAT3 is shown. The section (f) is a (d)+(e) superimposed image.

FIG. 4B shows images of an ultra-early-cancer cell group of healthy large intestine mucosa of a laboratory mouse stained with curcumin in living body staining and imaged with a confocal laser microscope.

FIG. 4C shows an image of a sample of human stomach adenoma immediately after surgical excision, stained with curcumin in living body staining, and imaged with a multiphoton laser microscope, with a color region stained with the curcumin dye extracted.

FIG. 4D shows an image of a sample of the human stomach adenoma immediately after surgical excision, double-stained with curcumin and Acid Red in living body staining, and imaged under the multiphoton laser microscope.

FIG. 4E shows images of the inner wall of the digestive tract double-stained with the stain containing curcumin and the stain containing Acid Red and then imaged under the multiphoton laser microscope. The section (a) shows an image of a healthy digestive tract, and the section (b) shows an image of cancer in the ultra-early stage.

FIG. 5A is a diagrammatic view showing the arrangement of the cells of the large intestine, which is an example of a digestive tract.

FIG. 5B diagrammatically shows cancer cells in ultra-early cancer that develop in the digestive tract.

FIG. 5C is a diagrammatic view showing that the inner wall of the digestive tract is imaged under the multiphoton laser microscope and the confocal laser microscope and further showing examples of cell images captured (a) at the focal plane that coincides with the mucosa surface and (b) at the focal plane that is located at the depth of about 50 μm below the mucosa surface.

FIG. 6A shows a case where two pattern types, a cancer-related gene STAT3 expression pattern stained with curcumin in living body staining and a ras-family cancer-related gene expression pattern stained with phloxine in living body staining, of a lesion (circular structure seen in central portion) called ACF (atypical crypt foci), which is considered as one form of a pre-cancer state, are simultaneously analyzed by using images produced under the multiphoton laser microscope. The section (a) shows an image of the STAT3 cancer-related gene expression pattern stained with curcumin in living body staining. The section (b) shows an image of the ras-family cancer-related gene expression pattern stained with phloxine in living body staining. The section (c) is an (a)+(b) superimposed image.

FIG. 6B is an enlarged view of FIG. 6A and shows the case where the two pattern types, the cancer-related gene STAT3 expression pattern stained with curcumin in living body staining and the ras-family cancer-related gene expression pattern stained with phloxine in living body staining, of the lesion (circular structure seen in central portion) called ACF (atypical crypt foci), which is considered as one form of the pre-cancer state, are simultaneously analyzed by using images produced under the multiphoton laser microscope. The section (a) shows an image of the STAT3 cancer-related gene expression pattern stained with curcumin in living body staining. The section (b) shows an image of the ras-family cancer-related gene expression pattern stained with phloxine in living body staining. The section (c) is an (a)+(b) superimposed image.

FIG. 7 shows a state in which an insertion tube has been inserted into a digestive tract. The section (a) of FIG. 7 shows a state immediately after the insertion tube is inserted, and the section (b) of FIG. 7 shows a state in which a space is formed in the digestive tract.

FIG. 8 shows an example of an application unit of a cancer test device according to a first embodiment.

FIG. 9 The section (a) of FIG. 9 shows that the cancer test device according to the first embodiment is used to planarize the inner wall of a digestive tract, and the section (b) of FIG. 9 is a diagrammatic view showing a front-end-side end portion of the cancer test device.

FIG. 10 is a schematic view showing the structure of a front end portion of an endoscope in the cancer test device according to the first embodiment.

FIG. 11 is a block diagram showing the control configuration of the cancer test device according to the first embodiment.

FIG. 12 is a flowchart showing an example of the action of the cancer test device according to the first embodiment.

FIG. 13 is a block diagram showing the control configuration of a cancer test device according to a second embodiment.

FIG. 14 is a diagrammatic view showing the cancer test device according to the second embodiment.

FIG. 16 is a schematic view showing the entire endoscope.

FIG. 17 is a block diagram showing the control configuration of the cancer test device.

FIG. 18 is a flowchart showing an example of the action of the cancer test device according to the third embodiment.

FIG. 19A is a merged image of the inner wall of the digestive tract stained with the stain containing curcumin and the stain containing Acid Red.

FIG. 19B is the merged image of the inner wall of the digestive tract stained with the stain containing curcumin and the stain containing Acid Red and shows the positional relationship between an imaging axis and the position in the developed image.

FIG. 20A shows three-dimensional data images illustrating a cell form over a predetermined depth range below the inner wall surface (mucosa surface) and representing an extracted color region stained both with the curcumin dye and the Acid Red dye.

FIG. 20B shows images representing a color region stained with the curcumin dye and extracted from the image shown in FIG. 20A.

FIG. 20C shows images representing a color region stained with the Acid Red dye and extracted from the image shown in FIG. 20A.

Figure 15:
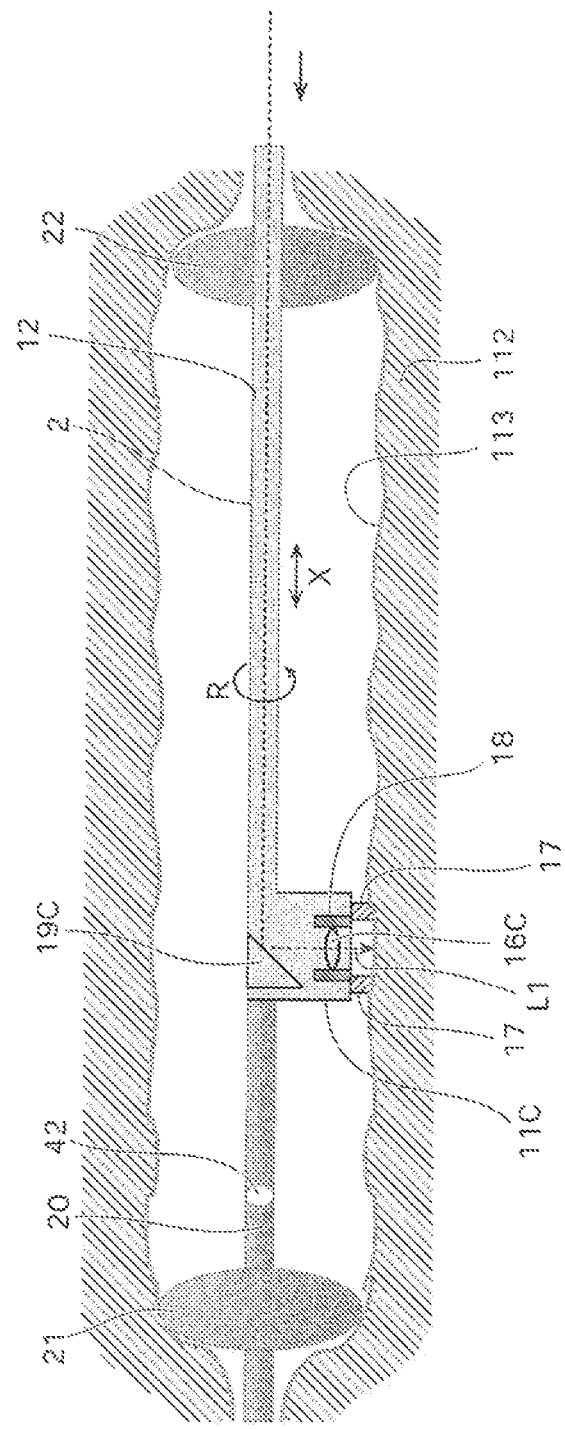
FIG. 15 is a schematic view showing a front-end-side end portion of an endoscope of a cancer test device according to a third embodiment.

DESCRIPTION OF EMBODIMENTS (Finding 1 on which Present Invention is Based)

The present invention is based on findings 1 and 2. Out of the findings, the finding 1 on which the present invention is based and a primary configuration of the invention associated with the finding 1 will first be described.

The cancerization mechanism, in which a healthy living cell transforms into a cancerous cell and the cancerous cell then grows, will first be described. FIG. 1A is a diagrammatic view showing a state in which cancer-related gene products in a living cell act normally. In the cell, there is a bidirectional signal transduction system that controls cell division and growth in the positive and negative directions. That is, there are a growth-promoting signal having the function of accelerating cell growth and a growth-inhibiting signal system having the function of inhibiting the growth. FIG. 1B is a diagrammatic view showing a state in which the cancer-related gene products in the living cell act abnormally. The cross star marks each indicate cancerous mutation that occurs in the corresponding cancer-related gene product.

A living cell is formed of a nucleus containing a cell growth gene and a cytoplasm that surrounds the nucleus. A cell contains a plurality of types of cancer-related genes each formed of proteins. The cancer-related genes are classified into those that belong to the ras (rat sarcoma) system and the STAT3 (signal transducer and activator of transcription 3) system, which each transmit the growth-promoting signal, and the APC (antigen presenting cell)/β-catenin family and the p53 (protein 53) system, which each transmit the growth-inhibiting signal, as shown in FIG. 1A. That is, the ras-family and STAT3-family cancer-related gene products are classified as gene products in the acceleration system, which transmits a cell growth promoting signal, and the APC/β-catenin-family and p53-family cancer-related gene are classified as gene products in the brake system, which transmits a cell growth inhibiting signal.

The mechanism that controls cell division and growth will be described. First, when a cell growth factor (EGF), which is an extracellular growth control substance, binds to a receptor located on the cell membrane of a living cell, the cancer-related gene products of the ras family and the STAT3 family, which belong to the accelerator system, are activated. When the resultant growth promoting signals are transmitted to the nucleus, a gene group necessary for cell growth is activated in the nucleus. On the other hand, in the cell, the cancer-related gene products of the APC/β-catenin family and the p53 family, which belong to the brake system, are always activated to some extent, and the resultant growth inhibiting signals inhibit the activation of the cell growth gene in the nucleus to attempt to inhibit the cell growth. In the case where the cancer-related genes in the living cell act normally, the effect of promoting the cell growth and the effect of inhibiting the cell growth work in a well-balanced manner, whereby the cells in the living body grow adequately.

In contrast, in the case where the ras-family or STAT3-family cancer-related gene product acts abnormally, the cancer-related gene product of the ras family or the STAT3 family, which belongs to the growth promoting signal system, has higher activity, so that the cell growth is enhanced more than necessary, as shown in FIG. 1B. Further, for example, in the case where the APC/β-catenin-family or p53-family cancer-related gene product acts abnormally, the cancer-related gene product of the APC/β-catenin family or the p53 family, which belongs to the growth inhibiting signal system, has lower activity, so that the function of inhibiting the cell growth decreases. As described above, when any of the plurality of types of cancer-related gene acts differently or abnormally, adequate growth in a healthy cell fails, and enhancement of abnormal cell growth, such as that in a cancer cell, starts.

FIG. 1C is a diagrammatic view showing a stepwise cancerization process of a living cell group on the inner wall surface of a digestive tract. In FIG. 1C, the cancerization process of the living cell group is divided into a first stage, a second stage, a third stage, and a fourth stage, which are sequentially shown.

The first stage is a stage in which cancerization is about to start in part of the living cell group. The first stage is believed to occur when the degree of activity of the APC/β-catenin-family cancer-related gene lowers and the function of inhibiting cell growth decreases accordingly. In this stage, it is shown that the cell growth is slightly enhanced, and that a pre-cancer state, which eventually may transform to a cancer cell, has at least occurred.

The second stage is another pre-cancer state in which the cancerization has advanced beyond the first stage. In the second stage, it is believed that the activity of the ras-family cancer-related gene rises so that the cell growth has been enhanced. It is further believed the STAT3-family cancer-related gene is likely to be activated in this stage. The cancer cell population has a small size having a diameter, for example, greater than or equal to 0.1 mm and smaller than or equal to 0.4 mm. The diameter of the cancer cell population is the diameter of a circle having the same area as the area of the cancer cell population. This stage is not a stage that immediately endangers the life of the patient, but it is desirably to lay a treatment plan or otherwise take measures in preparation for the future.

ACF (atypical crypt foci), which will be described later and is considered as one form of the pre-cancer state, is believed to be defined by the special name in correspondence with a cell group that belongs to the first and second stages and has clear morphological features characterized in that the opening or lumen of a gland, which normally has a circular shape, has an elongated slit-like shape and the number of goblet cells among the glandular cells decreases as compared with the number in the normal state.

The third stage is a stage in which part of the living cell group is infiltrated and cancer cells manifest. The third stage is believed to occur when the activity of the p53-family cancer-related gene lowers so that the function of inhibiting the cell growth decreases. In this stage, in which the activity of brake-system cancer-related gene products of both the p53-system and the APC/β-catenin-family lowers so that the function of inhibiting the cell growth greatly decreases, the growth of the cancer cells progresses at an accelerated tempo, and the cancer cells infiltrate the surrounding tissue. When the third stage is reached, the diameter of the portion in the third stage reaches 0.5 mm or greater, and if the third stage is left with no measure taken, cancer that causes the death of the individual is completed.

The fourth stage is a stage in which after the cancer cells completed in the third stage transform to cancer, further gene mutation occurs, and the cancer has progressed to malignant cancer, which is likely to further cause cell growth, infiltration, and metastasis. This stage is a stage in which the cancer metastasizes to remote organs other than the digestive tract and is a dangerous stage that endangers the life of the patient. It is believed that the speed at which the first stage progresses to the fourth stage depends on the state of the activity of the cancer-related genes.

FIG. 1D shows an example of a human cancer cell growth curve.

The number of cancer cells typically increases in accordance with a predetermined growth curve, as shown in FIG. 1D. For example, the growth curve has a small gradient for three years corresponding to the stage in which cancerization is about to start (period for which diameter of cancer cell population is smaller than 0.2 mm), whereas the gradient of the growth curve increases after four years and later (period for which diameter of cancer cell population is greater than or equal to 0.5 mm). The gradient of the growth curve then decreases after seven years and later. In general, the timing when cancer is clinically found and treated is after seven years or later. The reason for this is that no cancer cell population can be detected unless the diameter thereof increased to a value greater than or equal to 10 mm.

It is a noteworthy fact that the number of cells exponentially increases over the range of the growth curve indicated by the broken line A. The exponential increase means that the cancerous gene mutation that should occur in the first to third stages of the cancer cells has completed and the cancer cells repeatedly divide at a fixed uniform speed. If the cancer cell population can be detected at an early stage of the exponential increase (ultra-early cancer), that is, at a stage in which abnormality occurs in the cancer-related gene expression patterns but the cancer cell population itself has a small diameter of 1 mm or smaller, the cancer can be permanently cured because the ultra-early cancerous site is sufficiently small and can be readily fully removed. As described above, if the grade of the cancerization can be grasped in the form of abnormality in a cancer-related gene expression pattern in the ultra-early stage, the cancer can be permanently cured before the cancer develops to a dangerous stage.

Under the background described above, the present inventors have attempted to grasp the grade of cancerization by imaging a cancer-related gene expression pattern of a living cell group with a multiphoton laser microscope or a confocal laser microscope and visualizing the state of the activity of the cancer-related gene.

To visualize a cancer-related gene expression pattern of a living cell the present inventors have used a stain containing an edible dye to stain a cancer-related gene product in a chromatic color and imaged the stained cancer-related gene product. An edible dye is a natural dye or an artificial dye that is allowed to be administered to human (food coloring dye or dye that can be administered in the form of supplement, for example).

Specifically, a stain containing a curcumin-based compound (curcumin, $C_{21}H_{20}O_6$) was prepared as the stain that selectively stains the STAT3-family cancer-related gene product. Further, a stain containing phloxine ($C_{20}H_2Br_4Cl_4Na_2O_5$) was prepared as the stain that selectively stains the ras-family cancer-related gene expression pattern.

More specifically, a curcumin containing solution containing 1 wt % of curcumin was prepared as the stain containing a curcumin-based compound, and a phloxine containing solution containing 1 wt % of phloxine was prepared as the stain containing phloxine. The stain containing a curcumin-based compound may instead be a curcumin solution (undiluted liquid is, for example, liquid containing 5%-curcumin, 45%-glycerol, and 50%-ethanol) diluted with a physiological saline solution at a ratio ranging from 1/5 to 1/100. The stain containing 1%-phloxine may instead be a phloxine solution (10 mg/mL of undiluted liquid) with no change or having a concentration of 100% or diluted at a ratio of 1/10.

The stain containing a curcumin-based compound was used to stain the expressed STAT3-family cancer-related gene product in the living cell, and the stained product was then washed with physiological saline solution for about 10 seconds three times. The stain containing phloxine was used to stain the ras-family cancer-related gene expression pattern in the living cell, and the stained pattern was then washed with physiological saline solution for about 10 seconds three times. The thus performed double staining allowed simultaneous analysis of the amounts of expression of the STAT3-family and ras-family cancer-related gene products. The staining period for each of the stains ranged from 2 to 5 minutes. Since the concentrations described above allow the stains to penetrate into the cytoplasm but does not allow the stains to penetrate into the nucleus in the cell as long as the period having elapsed since the staining started is 10 minutes or shorter, the nucleus surrounded by the cytoplasm can be sharply visualized, whereby the analysis can be more distinctly performed.

The expression patterns of the STAT3-family and ras-family cancer-related gene products stained with the stains described above were imaged with a multiphoton laser microscope (FV1000MPE manufactured by Olympus Corporation). The wavelength of the laser light was 840 nm. An imaging target was the inner wall of the large intestine of a laboratory mouse, and the inner wall of the large intestine was so observed as to be divided into a plurality of sites where cancer cells developed (specimens 1, 2, and 3) and a healthy cell site where no cancer cell has developed (specimen 4).

FIG. 2A shows images of the cancer-related gene expression pattern of a group of living cell populations of the laboratory mouse large intestine associated with the specimen 1: The section (a) shows an image of the STAT3-family cancer-related gene product with the cancer cells stained more heavily than the healthy cells with the stain containing a curcumin-based compound; the section (b) shows an image of the ras-family cancer-related gene expression pattern stained with the stain containing phloxine; and the section (c) is an (a)+(b) superimposed image. FIG. 2A, and FIGS. 2B and 2C and FIG. 3, which will be described later, are each a monochromatic image but are inherently a color image.

In the section (a) of FIG. 2A, the STAT3-family cancer-related gene product is expressed in a green fluorescence color. The ratio of the region stained in the green fluorescence color to the entire screen, that is, the proportion of the region occupied by cells dominated by the STAT3-family cancer-related gene expression is 30%.

In the section (b) of FIG. 2A, the ras-family cancer-related gene is expressed in a red fluorescence color. The ratio of the region stained in the red fluorescence color to the entire screen, that is, the proportion of the region occupied by cells dominated by ras-family cancer-related gene expression is 80%.

In the section (c) of FIG. 2A, the region where the STAT3-family cancer-related gene product and the ras-family cancer-related gene expression pattern coexist is expressed in a yellow fluorescence color, the region where only the STAT3-family cancer-related gene expression exists is expressed in the green fluorescence color, and the region where only the ras-family cancer-related gene expression exists is expressed in the red fluorescence color. The ratio of the region stained in the yellow fluorescence color to the entire screen is 10%.

In the group of living cell populations of the laboratory mouse large intestine associated with the specimen 1, the proportion of the region occupied by cells dominated by STAT3-family cancer-related gene expression was 30%, the proportion of the region occupied by cells dominated by ras-family cancer-related gene expression was 80%, and the proportion of the region where the two types of cells described above coexist was 10%. The state of the group of living cell populations associated with the specimen 1 is believed to be the second or third stage (ultra-early cancer) shown in FIG. 1C in terms of the grade of cancerization.

That is, the stage of the group of living cell populations is diagnosed as follows: Cells that are positive in terms of both STAT3-family and ras-family account for 10%; the group of these cells has advanced beyond at least the second stage; the population of these cells has a diameter of at least 0.2 mm (see FIG. 1D); and it is therefore estimated that the group of living cell populations is likely to have already entered the third stage (ultra-early cancer).

FIG. 2B shows images of the cancer-related gene expression pattern of a group of living cell populations associated with the specimen 2, and the images are shown in the same manner as those in FIG. 2A.

In the section (a) of FIG. 2B, the ratio of the region stained in the green fluorescence color to the entire screen, that is, the proportion of the region of the STAT3-family cancer-related gene expression is 50%. In the section (b) of FIG. 2B, the ratio of the region stained in the red fluorescence color to the entire screen, that is, the proportion of the region of the ras-family cancer-related gene expression is 90%. In the section (c) of FIG. 2B, the ratio of the region stained in the yellow fluorescence color to the entire screen, that is, the proportion of the region where the STAT3-family cancer-related gene and the ras-family cancer-related gene coexist is 20%. In the group of living cells, the STAT3-family and ras-family cancer-related genes are activated, and cancerization that is diverse in terms of gene expression is recognized, as in the specimen 1 (see FIG. 2A). The stage of the group of living cell populations associated with the specimen 2 is diagnosed as follows: Cells that are positive in terms of both STAT3-family and ras-family account for 20%; the group of these cells has advanced beyond at least the second stage; the population of these cells has a diameter of at least 0.2 mm (see FIG. 1D); and it is therefore estimated that the group of living cell populations is likely to have already entered the third stage (ultra-early cancer).

FIG. 2C shows images of the cancer-related gene expression pattern of a group of living cell populations associated with the specimen 3, and the images are shown in the same manner as those in FIG. 2A.

In the section (a) of FIG. 2C, the ratio of the region stained in the green fluorescence color to the entire screen, that is, the proportion of the region of the STAT3-family cancer-related gene expression is 30%. In the section (b) of FIG. 2C, the ratio of the region stained in the red fluorescence color to the entire screen, that is, the proportion of the region of the ras-family cancer-related gene expression is 75%. In the section (c) of FIG. 2C, the ratio of the region stained in the yellow fluorescence color to the entire screen, that is, the proportion of the region where the STAT3-family cancer-related gene and the ras-family cancer-related gene coexist is 5%. In the group of living cells associated with the specimen 3, the ras-family cancer-related gene is not activated, so that the gene expression in the cancer cells is not as diverse as that in the specimen 1 (see FIG. 2A).

The stage of the group of living cell populations associated with the specimen 3 is diagnosed as follows: Cells that are positive in terms of both STAT3-family and ras-family account for 5%; the group of these cells has advanced beyond at least the second stage; and the population of these cells has a diameter of about 0.1 mm (see FIG. 1D). In consideration of the state in which the STAT3-family positive cells are scattered in the form of many island-shaped portions, it is expected that the mobility of the cells has been enhanced and the infiltration has increased, and it is then estimated that the cells are likely to have already entered the third stage (ultra-early cancer). The detailed cell-level analysis of the states of the expression of many cancer-related gene products allows cancer stage diagnosis and cancerization grade diagnosis. It is believed that the metastasis is evaluated based on the dispersibility of cancer cells, and that the size of a cell population indicates the growth ability.

As shown, for example, in the section (a) of FIG. 2C, a case where individual cancer populations per unit area each have a small diameter but there are a large number of scattered cancer populations is believed to indicate that metastasis advances. As described above, the fact that metastatic cancer has a small average size (diameter) can be incorporated in the analysis approach. It is desirable in this case that the metastatic level is classified into three to five stages, and that a determined metastatic level is described along with the grade of cancerization expressed, for example, by the ras and STAT3 stained areas.

FIG. 3 shows images of a group of healthy living cells of the large intestine of the laboratory mouse associated with the specimen 4. In the sections (a) to (c) of FIG. 3, no green, red, or yellow fluorescence color is present in the screen, but the screen is expressed in a dark color. In the group of living cells associated with the specimen 4 having no cancer cell, the amounts of expressed STAT3-family and ras-family cancer-related gene products are not enhanced.

Analysis of expression of cancer-related genes in a group of living cells as described above allows determination of the grade of cancerization. That is, according to the primary configuration of the present invention, ultra-early cancer having a so small lesion size that a current test device (such as endoscope) cannot detect even the presence of the ultra-early cancer can be found in an early stage, and the prognosis of the cancer patient can be understood through evaluation of the grade of the cancer cells. The cancer can be permanently cured by fully removing the cancerous site in an early stage as described above.

FIG. 4B shows images of healthy large intestine mucosa and colorectal cancer stained with curcumin in living body staining and imaged with a confocal laser microscope and shows that the contour of each cell and the shape of the nucleus in the cell can be clearly visualized because curcumin is loaded into the cytoplasm but is not loaded into the nucleus so that pathological diagnosis can be reliably performed. In the section (b) of FIG. 4B, since crypts cannot be seen due to the colorectal cancer site, unlike the section (a) of FIG. 4B, the section (b) of FIG. 4B can be used in cancer evaluation.

Further, the section (a) of FIG. 4C shows an image of a surgically excised fresh specimen of human stomach adenoma stained with curcumin ex vivo in living body staining and imaged with a multiphoton laser microscope. The section (a) of FIG. 4D shows an image of a surgically excised fresh specimen of human stomach adenoma double-stained with curcumin and Acid Red ex vivo in living body staining. Since the contour of each cell and the shape of the nucleus can be clearly visualized, pathological diagnosis can be reliably performed also in this case. The graphs drawn in the right section (b) of FIGS. 4C and 4D show that the hatched bands labeled with Filter1 and Filter2 represent the wavelength widths of filters used to measure the fluorescence, that E2 represents the characteristic of the fluorescence emitted from curcumin, and that E7 represents the characteristic of the fluorescence emitted from Acid Red. Therefore, in the section (a) of FIG. 4D, the difference in wavelength of the fluorescence provided by the two-color staining is expressed in the form of the difference in color. FIG. 4D shows a monochromatic image and is therefore considered to show the difference in contrast but is actually captured as an image that is clearly dividable in terms of wavelength. In FIGS. 4C and 4D, the regions which are labeled with II and where cancerization is about to start are each a kind of cytologic atypia, and nuclei in the gland are arranged in two rows and division due to cancer is about to start. That is, visualization of the nuclei allows clear grasp of a situation in which cancerization is about to start on a cell basis.

The present inventors have ascertained, as an example in which cancer-related gene expression patterns are selectively stained, that a stain containing a curcumin-based compound is used to selectively stain a STAT3-family cancer-related gene product in a chromatic color. FIG. 4A shows monochromatic images that are inherently color images. The images can be produced both with a confocal laser microscope and a multiphoton laser microscope.

The sections (a), (b), and (c) of FIG. 4A are images of a sample that is a double-stained living cell group of the inner wall of the intestine of a living laboratory mouse produced by staining the inner wall of the intestine with a 1%-curcumin solution and then staining the curcumin-stained inner wall with 1%-Acid Red ($C_{27}H_{29}N_2NaO_7S_2$). A confocal laser microscope was used as the image device.

In the section (a) of FIG. 4A, the region stained with Acid Red is shown in deep red, so that the structure of capillaries and connective tissue (mesh structure) around the glands of the large intestine is visualized. In the section (b) of FIG. 4A, the region stained with the curcumin-based compound is shown in deep green. The section (c) of FIG. 4A is an (a)+(b) superimposed image. It is believed based on the section (c) of FIG. 4A that ultra-early cancer has developed in the region heavily stained with the curcumin-based compound because the structure of the glands and the capillaries and connective tissue around the glands (crypt structure) stained with Acid Red disappears and is disturbed.

The three panels in the upper row of FIG. 4A show that (b) there is a cell group which is enclosed by the white-line rectangle and where the living body staining using the stain containing a curcumin-based compound stained cancer cells more heavily than healthy cells, and that comparison of the enclosed site with (a) the same site of the image of the cell group stained in the living body staining using the stain containing Acid Red shows that the mesh pattern (crypt pattern) in which the capillaries stained with Acid Red surround the glands disappears. It is therefore determined that the site containing the cell group heavily stained with the curcumin stain is ultra-early cancer. The three panels (d), (e), and (f) in the lower row of FIG. 4A show images of the same site of the large intestine of the digestive tract of the laboratory mouse imaged in the same living body staining as that in the upper row, fixed with formalin, and then imaged in the fluorescence antibody technique. The section (d) shows that intracellular actin filaments were visualized with Alexa-488-labeled phalloidin. The section (e) shows that the intracellular actin filaments were stained with anti-STAT3 antibody and Alexa-594-labeled secondary antibody at the same time so that the distribution of the cancer-related gene product STAT3 is shown. The section (f) is a (d)+(e) superimposed image.

The sections (d), (e), and (f) of FIG. 4A are produced by fixing the intestine of the laboratory mouse described above with formalin, then immunostaining the intestine with an anti-STAT3 antibody that bonds to the STAT3-family cancer-related gene product, and imaging the same location as those surrounded by the white frames in the sections (a), (b), and (c). In the sections (d) to (f), the samples were fixed with formalin and therefore slightly shrunk.

The three panels in the lower row were obtained by imaging the white rectangular sites in the upper three panels. The distribution of the cell group shown in the section (b) in the upper row and heavily stained with curcumin in the living body staining coincides with the distribution of the cell group shown in the section (e) in the lower row and having the cancer-related gene product STAT3 highly expressed, which suggests that living body staining of the living cells with curcumin detects the cancer-related gene product STAT3.

Further, out of the three panels in the lower row, comparison between the distribution of the cell group shown in the section (e) and having the cancer-related gene product STAT3 highly expressed and the distribution of the intracellular actin filaments in the section (d) indicates that the cell group in which STAT3 is highly expressed has a sparse distribution of the actin filaments, which indicates that the inter-cell bonding is sparse. Based on the fact that the inter-cell bonding is typically sparse in a cancerous cell, the cell group in which STAT3 is highly expressed is formed of cancerous cells.

In summary, the three panels in the lower row prove that cancerization has occurred in the central-part cell group that is poor in actin filaments, and that the cell group coincides with the cell group in which the cancer-related gene product STAT3 is highly expressed. Further, the three panels in the upper row prove that the cell group in which the cancer-related gene product STAT3 is highly expressed is formed of ultra-early cancer cells more heavily stained in the curcumin living body staining than the healthy cells.

These images were captured with a confocal laser microscope, and similar images can be captured with a multiphoton laser microscope.

The section (d) of FIG. 4A primarily shows the contours of the cells visualized by actin fluorescence. The section (e) of FIG. 4A shows cells immunostained with the anti-STAT3 antibody. The section (f) of FIG. 4A is the (d)+(e) superimposed image and shows that the amount of white actin reaction decreases in the island-shaped portion in a central portion of the screen, and that the amount of green STAT3-family protein immunoreaction increases. It is therefore believed that a large amount of STAT3-family cancer-related gene product has been expressed in the island-shaped portion.

Referring to the images in FIG. 4A, since the region in the section (c) of FIG. 4A, where cancer cells have developed, coincides with the region in the section (f) of FIG. 4A, where STAT3-family cancer-related gene product is detected, it is indicated that ultra-early cancer has developed and the cancer-related gene product relating to the ultra-early cancer has been expressed in the region heavily stained with the curcumin-based compound in the living cells. As described above, differences in luminance and fluorescence color or a difference in geometric pattern allows image-based detection of expression of a cancer-related gene in an ultra-early stage and analysis of the grade of cancerization in computer-based automatic diagnosis. The automatic diagnosis employs, for example, a method for identifying the expression location based on highly probable luminance and analyzing a regular distribution of the crypt structure to determine the grade of cancerization based on the degree of disappearance of the structure and the state of mixed fluorescence colors. In a method using a geometric pattern, the pattern varies on an organ basis. In the example in the section (c) of FIG. 4A, it is conceivable to employ, for example, a method for counting the number of dark portions in a fixed area of a 500-μm square (dark hole pattern) to quantify the density of the dark portions. The automatic diagnostic can further be useful for artificial-intelligence-based diagnosis for recognition from stored images of a large number of cancer-related gene expression patterns and healthy cell patterns. In addition to the hole pattern of the crypt structure, depending not only on the number of repetitions of dark and bright portions but the depth of penetration of a living body stain into a living cell, the depth of imaging and the wavelength in confocal and multiphoton laser microscopy, a difference between stains, and other factors, the geometric pattern is imaged as a different pattern in some cases, for example, in the sections (a) and (b) of FIG. 4E, which show images of stained intestine of a laboratory mouse. Measurement of the density of the island pattern based on the glands and capillaries, recognition of disturbance of the island pattern, for example, in the section (a) of FIG. 4E, and any other diagnosis method can be employed. Further, distance measurement, such as the interval between the dark portions, the diameters of the dark portions, and other factors in the section (c) of FIG. 4A and the interval in the island pattern, the diameter of the island pattern, and other factors in the section (a) of FIG. 4E, is useful in evaluation of the disturbance of the pattern.

As described above, detailed cell-level analysis of the states of expression of a large number of cancer-related gene products allows cancer stage diagnosis and cancerization grade diagnosis. It is believed that the metastasis is evaluated based on the dispersibility of cancer cells, and that the size of a cell population indicates the growth ability.

For example, a case where individual cancer populations per unit area each have a small diameter but there are a large number of scattered island-shaped populations is believed to indicate that metastasis advances. As described above, the fact that metastatic cancer has a small average size can be incorporated in the analysis approach.

(Finding 2 on which Present Invention is Based)

The finding 2, on which the present invention is based, and a primary configuration of the invention associated with the finding 2 will next be described.

The relationship between the internal structure of a living body and cancer cells will first be described.

The interior of a living body contains the digestive tract, the respiratory system, the renal/urinary system, the utero-ovarian reproductive system, and other organs, the cerebrospinal nervous system, and other body sites. Examples of the digestive tract may include the esophagus, the stomach, the small intestine, and the large intestine.

FIG. 5A is a diagrammatic view showing the arrangement of the cells of the large intestine, which is an example of a digestive tract 112. For example, the inner wall of the large intestine is formed of a gland 130, which secretes mucus, and an epithelium 120, which is located in a portion closer to an inner wall surface (mucosa surface) 113 than the gland 130 and absorbs water when coming into contact with food. The epithelium 120 is formed of a plurality of epithelial cells 121 arranged along the inner wall surface 113. The epithelial cells 121 each have a nucleus 125 and cytoplasm 126. The gland 130 is so shaped that part of the epithelium 120 is recessed in the form of a pot. The gland 130 is formed of a plurality of glandular cells 131, and the glandular cells 131 each have a nucleus 135 and cytoplasm 136. The recessed portions of the gland 130 are called crypts 138 of the gland 130. A basement membrane 137, capillaries 132, and connective tissue 133 are formed in the portion inside the epithelial cells 121 and the portion around the glandular cells 131. A thin layer of the mucus secreted from the gland 130 is formed on the surfaces of the epithelial cells 121, and the epithelial cells 121 are protected by the mucus layer.

FIG. 5B diagrammatically shows a cancer cell population 152, which develops in the digestive tract 112. The ultra-early-stage cancer cell population 152, which develops in the digestive tract 112, is generally believed to develop in a position below the inner wall surface (mucosa surface) 113 of the digestive tract 112 at a depth of about 1 mm or smaller. If the early-stage cancer cell population 152, which has not yet reached and penetrated into a muscular layer of mucosa 160, can be found over a wide range of the mucosa of the digestive tract with no missing cancer cell population, the number of conditions leading to an advanced cancer, which is a state in which the cancer cell population proliferates beyond the muscular layer of mucosa 160 and spreads to another organ, can be reduced.

FIG. 5C is a diagrammatic view showing that the inner wall of the digestive tract 112 is imaged under a multiphoton laser microscope and a confocal laser microscope. To irradiate the inner wall of the digestive tract 112, which is an imaging target, with laser light L, an objective lens 16 of the multiphoton laser microscope and the confocal laser microscope is so disposed as to face the inner wall surface 113 of the digestive tract 112, as shown in FIG. 5C. FIG. 5C is a diagrammatic view with the left half of FIG. 5C showing that the inner wall of the digestive tract is imaged under the multiphoton laser microscope or the confocal laser microscope and the right half of FIG. 5C showing examples of cell images captured (a) at the focal plane that is the plane of the cross section taken along the line a-a and that coincides with the mucosa surface and (b) at the focal plane that is the plane of the cross section taken along the line b-b and that is located at the depth of about 50 μm below the mucosa surface. The multiphoton laser microscope allows imaging over the range from the mucosa surface to a depth of about 500 μm or a depth of 1000 μm, and the confocal laser microscope allows imaging over the range from the mucosa surface to a depth of about 50 μm or a depth of 100 μm.

To primarily image the epithelial cells 121, the objective lens 16 is so disposed that the focal point of the objective lens 16 coincides with the inner wall surface (mucosa surface) 113. As a result, the epithelial cells 121 and other parts are imaged as shown in the section (a) of FIG. 5C, which is a diagrammatic view taken along the line a-a in FIG. 5C. On the other hand, to primarily image the glandular cells 131, the capillaries 132, and the connective tissue 133, the objective lens 16 is so disposed that the focal point of the objective lens 16 coincides with a position below the inner wall surface (mucosa surface) 113 at a depth of 10 μm or greater. As a result, the glandular cells 131, the capillaries 132, and the connective tissue 133 are imaged as shown in the section (b) of FIG. 5C, which is a diagrammatic view taken along the line b-b in FIG. 5C.

For example, if the size and shape of a cancer-related gene expression pattern that appears in the nucleus 125 or 135 or a crypt 138 of the gland 130 can be detected in the pre-cancer state (second stage shown in FIG. 1C), the grade of cancerization can be determined in the ultra-early stage, in which the diameter of the cancer cell population is greater than or equal to 0.5 mm but smaller than or equal to 1 mm.

FIG. 6A shows images of a cancer-related gene expression pattern of living cells. FIG. 6B is an enlarged view of FIG. 6A. FIGS. 6A and 6B show monochromatic images that are inherently color images.

FIG. 6A shows a case where two pattern types, a cancer-related gene STAT3 expression pattern stained with curcumin in living body staining and a ras-family cancer related gene expression pattern stained with phloxine in living body staining, of a lesion (circular structure seen in central portion) called ACF (atypical crypt foci), which is considered as one form of the pre-cancer state, are simultaneously analyzed by using the images produced under the multiphoton laser microscope. The section (a) shows an image of the STAT3 cancer-related gene expression pattern stained with curcumin in living body staining. The section (b) shows an image of the ras-family cancer-related gene expression pattern stained with phloxine in living body staining. The section (c) is an (a)+(b) superimposed image.

FIGS. 6A and 6B show images produced by actually imaging the cancer-related gene expression patterns stained with a stain 45 under the multiphoton laser microscope (FV1000MPE manufactured by Olympus Corporation). The wavelength of the laser light was 840 nm, and the imaging target was a laboratory mouse. The stain is the same as the stain shown in the finding 1, the stain containing a curcumin-based compound (curcumin, $C_{21}H_{20}O_6$) as the stain that selectively stains the STAT3-family cancer-related gene product, and the stain containing phloxine ($C_{20}H_2Br_4Cl_4Na_2O_5$) as the stain that selectively stains the ras-family cancer-related gene expression pattern.

FIGS. 6A and 6B each show a state in which part of the crypts 138 has been stained in green and the STAT3-family cancer-related gene product has been expressed in the crypts 138. The structure of the central portion of FIGS. 6A and 6B is called ACF (atypical crypt foci) pre-cancer state. The structure of the central portion in FIGS. 6A and 6B forms a gland-like structure in which glandular cells are arranged. The opening or lumen of the gland in the central portion has a circular shape in the healthy colorectal mucosa, whereas the structure of the central portion in FIGS. 6A and 6B has an elongated slit-shaped opening, and the number of goblet cells among the glandular cells decreases than that under the healthy condition. The structure of the central portion therefore has obvious morphological characteristics of ACF. In the pre-cancer state ACF, (a) slight enhancement of the STAT3 cancer-related gene expression stained with curcumin in living body staining and (b) moderate enhancement of ras-family cancer-related gene expression stained with phloxine in living body staining are recognized. Further, the crypts 138 in the healthy state each have a roughly circular shape, whereas in the ACF pre-cancer state shown in FIGS. 6A and 6B, two crypts 138 adjacent to each other each have an elongated deformed shape, from which it can be determined that the living cells are in an abnormal state. As described above, detecting the size and shape of each cancer-related gene expression pattern in the pre-cancer state allows determination of the grade of cancerization in the early stage and understanding of the prognosis of the cancer patient.

First Embodiment

A first embodiment will be described below in detail with reference to the drawings.

The embodiments described below are each a preferable specific example of the present invention. Numerical values, shapes, materials, constituent elements, the positions where the constituent elements are arranged, the form in accordance with which the constituent elements are connected to each other, steps, the order of the steps, and other factors shown in the following embodiments are presented by way of example and are not intended to limit the present invention. The present invention is specified by the claims. Therefore, out of the constituent elements in the following embodiments, a constituent element that is not described in any independent claim will be described as an arbitrary constituent element. Further, in the drawings, substantially the same configurations have the same reference character, and a duplicated description of such configurations will be omitted or simplified.

[1. Overall Configuration of Cancer Test Device]

A cancer test device according to the present embodiment is a device capable of finding cancer cells having developed in the digestive tract, the respiratory system, the renal/urinary system, the utero-ovarian reproductive system, the cerebrospinal nervous system, and other body sites in an early stage of the cancer. The cancer test device can not only perform the cancer test but treat the cancer cells having developed in the living body. Further, the cancer test device can handle not only the interior of a living body but a fresh ex-vivo sample within about 20 minutes immediately after the sample is surgically excised with the sample kept intact and can pathologically diagnose cancer and analyze the expression of the cancer-related genes in the same method as that used for the interior of the living body. For example, a sample needs to be frozen, sliced into a thin specimen, and stained with hematoxylin and eosin (HE) in related art, so that whether or not cancer cells are present in a resection stump is pathologically diagnosed and requires at least 20 minutes. On the other hand, the approach according to the present embodiment allows accurate diagnosis with no missing lesion in 3 to 5 minutes (rapid intraoperative diagnosis). Further, the cancer test device and test method according to the present invention are applicable to even an excised, cultured-state ips cell, an ES cell, a MUSE cell, or any other cell other than a living body.

Further, the cancer test device according to the present embodiment is an endoscope-shaped test device. The following description will be made with reference to a case where the digestive tract in a living body is tested.

[1.1. Configuration for Test Preparation]

The configuration of the cancer test device for test preparation will first be described.

Since the inner wall of an actual digestive tract has irregularities, it is desirable to widen the digestive tract to make the digestive tract imageable before the inner wall is imaged by using the cancer test device. To this end, the cancer test device according to the present embodiment includes an insertion tube that widens the digestive tract.

FIG. 7 shows a state in which an insertion tube 20 has been inserted into the digestive tract 112. The section (a) of FIG. 7 shows a state immediately after the insertion tube 20 is inserted, and the section (b) of FIG. 7 shows a state in which a space S is formed in the digestive tract 112.

The insertion tube 20 has a supply port 42, through which fluid is supplied, and a recovery port 43, through which the supplied fluid is recovered, as shown in the section (a) of FIG. 7. The insertion tube 20 is further provided with a first balloon 21 and a second balloon 22. The first balloon 21 and the second balloon 22 bulge and shrink when the fluid (gas or liquid) is injected into and discharged from the balloons 21 and 22. The first balloon 21 is provided in a position shifted from the supply port 42 toward the front end of the insertion tube 20, and the second balloon 22 is provided in a position shifted from the recovery port 43 toward the rear side of the insertion tube 20 (opposite the front end). Causing the first balloon 21 and the second balloon 22 to bulge in the digestive tract 112 creates a closed space S sandwiched between the first balloon 21 and the second balloon 22, as shown in the section (b) of FIG. 7.

[1.2. Basic Configuration of Cancer Test Device]

The basic configuration of a cancer test device 1 will next be described with reference to FIGS. 8 to 11. FIG. 8 shows an example of an application unit 40 of the cancer test device 1.

The cancer test device 1 according to the present embodiment includes the application unit 40, which applies a stain 45 onto the inner wall of the digestive tract 112 in the closed space S.

The cancer test device 1 supplies the stain 45 from the application unit 40, which contains the stain 45, via the insertion tube 20 and the supply port 42 into the space S to apply the stain 45 onto the inner wall of the digestive tract 112, as shown in FIG. 8. Cancer-related gene products in living cells of the digestive tract 112 are stained with the applied stain 45 in a chromatic color.

The stain 45 may, for example, be a single stain formed of a stain containing a curcumin-based compound or a stain containing phloxine. It is, however, desirable to use two stains, the stain containing a curcumin-based compound and the stain containing phloxine. Using the stain 45 containing a curcumin-based compound allows grasp of the state of a STAT3-family cancer-related gene expression pattern, and using the stain 45 containing phloxine allows grasp of the expression state of a ras-family cancer-related gene product.

Curcumin-based compounds include not only curcumin, of course, but highly water-soluble curcuminoid (mixture of several types of curcumin derivatives).

The stain that stains the ras-family cancer-related gene expression pattern can, in place of phloxine described above, be a stain containing any of the following materials:

erythrosine ($C_{20}H_8I_4O_5$)
merbromin ($C_{20}H_8Br_2HgNa_2O_6$)
fast green FCF ($C_{37}H_{34}N_2Na_2O_{10}S_3$)
meclocycline sulfosalicylate ($C_{29}H_{27}ClN_2O_{14}S$)

Before the staining, the interior of the digestive tract 112 may be cleaned and the mucus in the digestive tract 112 may be removed via the supply port 42 and the recovery port 43.

The section (a) of FIG. 9 shows that the cancer test device 1 is used to planarize the inner wall of the digestive tract 112.

After the stain 45 is applied to a cell group in the living body, gas is, for example, supplied via the supply port 42 to cause the digestive tract 112 to bulge, as shown in the section (a) of FIG. 9. As a result, the inner wall of the digestive tract 112 is stretched and planarized. It is desirable that the irregularities of the planarized inner wall surface 113 have a height difference, for example, smaller than or equal to 0.2 mm. Planarizing the inner wall of the digestive tract 112 allows precise grasp of the states of the inner wall surface 113 and the cancer-related genes in the living cell group in a position below the inner wall surface 113 at a predetermined depth.

The section (b) of FIG. 9 is a schematic view showing a front-end-side end portion of an endoscope 2 of the cancer test device 1 in FIG. 11. FIG. 10 is a schematic view showing the structure of a rotary portion at the front end of the endoscope 2. FIG. 11 is a block diagram showing the control configuration of the cancer test device 1.

The cancer test device 1 includes, in addition to the application unit 40 described above, an imaging unit 10 including the endoscope 2, and a control unit 50, which controls the motion of the imaging unit 10 and the application unit 40. The control unit 50 includes an evaluation unit 52, which evaluates the grade of cancerization, and a storage unit 51, which stores information that serves as an evaluation reference when the grade of cancerization is evaluated. The evaluation unit 52 and the storage unit 51 will be described later.

The cancer test device 1 further includes a laser oscillator 60, an optical part 65, and an image processing unit 70.

Laser light L emitted from the laser oscillator 60 is reflected off a dichroic mirror 66, which is the optical part 65, further reflected off a mirror 19 in the endoscope 2, and applied to the living body. The cancer-related gene products in the living cells irradiated with the laser light L produce fluorescence, and the fluorescence is reflected off the mirror 19, passes through the dichroic mirror 66, and is detected with a photodetector 35. The light detected with the photodetector 35 is converted into an electric signal, and the image processing unit 70 forms an image according to the electric signal. A two-dimensional scanner 67 is built in the space between the laser oscillator 60 and the dichroic mirror 66 (FIG. 11). The two-dimensional scanner 67 scans a fixed area of an imaging target region with the radiated laser light in the X-Y directions to allow the laser light, which acts as a point, to form a planar image. Since the color of the fluorescence changes in accordance with the stain, the photodetector 35 is formed of a plurality of photodetectors, and a color separation optical filter is disposed on the upstream side of the photodetector 35 for color separation. The color may instead be separated by using a CMOS (complementary metal oxide semiconductor) device or a CCD (charge coupled device) as the photodetector 35.

The laser oscillator 60 to be used in the multiphoton laser microscope is configured to have a pulse width ranging from several tens to several hundreds of femtosecond and a pulse frequency ranging from several tens to several hundreds of megahertz. The laser light L in the present embodiment is two-photon laser light, which is a kind of multiphoton laser light, and the laser oscillator 60 uses, for example, a pulse laser capable of emitting light having a wavelength of 800 nm and a power of 3.2 W at the maximum. In the imaging operation, the laser outputs laser light having a power ranging from 0.16 to 0.32 W. Setting the wavelength at 800 nm or longer can prevent photons that belong to the ultraviolet region (wavelength shorter than 400 nm) from being produced in the half-wavelength light produced in the multiphoton excitation process. The laser oscillator 60 to be used in the confocal laser microscope is, for example, a continuous-wave (CW) laser outputting light having a visible wavelength for a typical confocal laser microscope.

The dichroic mirror 66, which is the optical part 65, reflects light having the same wavelength as that of the laser light L and transmits light having the other wavelengths. The laser light L emitted from the laser oscillator 60 is therefore reflected off the dichroic mirror 66 toward the mirror 19. On the other hand, the fluorescence produced in the cancer-related gene products is reflected off the mirror 19, then passes through the dichroic mirror 66, and reaches the photodetector 35. The optical part 65 can instead be formed, for example, of a prism or a λ/4 plate.

The imaging unit 10 includes the endoscope 2 and the photodetector 35 and applies the laser light L to the interior of the living body (living cell group) to image the intracellular fluorescence intensity of the fluorescence emitted from the living-body stain and the intracellular distribution form of the living-body stain, the intracellular fluorescence intensity and the intracellular distribution form reflecting a specific cancer-related gene product expression pattern. The imaging unit 90 includes a focal position control unit and controls the focal position control unit to image the cancer-related gene expression pattern stained with the stain.

The photodetector 35 detects the fluorescence produced when the laser light L is applied to the living cells and converts the fluorescence into an electric signal according to the intensity of the fluorescence. The photodetector 35 can, for example, be a photomultiplier or a CCD semiconductor image sensor.

The endoscope 2 includes an inner tube 12 and an outer tube 13, which surrounds part of the outer surface of the inner tube 12, as shown in FIG. 10. The inner tube 12 and part of the outer tube 13 are inserted into the living body. The inner tube 12 has a length, for example, of 50 mm and an outer diameter ranging, for example, from 3 to 10 mm. A linear-motion actuator is attached to the inner tube 12, and the inner tube 12 is movable relative to the outer tube 13 in the axial direction X by about 25 mm. An ultrasonic motor is further attached to the inner tube 12, and the inner tube 12 is revolvable relative to the outer tube 13 over 360°. The action of the inner tube 12 in the axial direction X or the revolutional direction R is controlled by the control unit 50.

An imaging head 11 is provided at a front-end-side end portion of the inner tube 12 of the endoscope 2. The imaging head 11 is inserted along with the inner tube 12 into the living body in such a way that the imaging head 11 and the inner tube 12 pass by the insertion tube 20, as shown in the section (b) of FIG. 9. The imaging head 11 is so controlled as to move in the living body based on the actions of the inner tube 12 in the axial direction X and the revolutional direction R.

The imaging head 11 includes the objective lens 16, a focal point changer 18, a spacer 17, and the mirror 19.

The mirror 19 is a part that redirects the laser light L outputted from the laser oscillator 60 toward the objective lens 16 or redirects the fluorescence emitted from the cancer-related gene products toward the photodetector 35, as described above.

The objective lens 16 is so provided as to face the inner wall surface 113 of the living body. The objective lens 16 to be used can be a lens having a diameter ranging from 3 mm to 5 mm, which allows the objective lens 16 to be readily inserted into the living body.

The focal point changer 18 is, for example, a piezoelectric actuator and moves the objective lens 16 in the optical axis direction to change the position of the focal point of the objective lens 16. The focal point changer 18 operates under the control of the control unit 50 and can adjust the focal point over a depth range from 0 to 1000 μm below the surface of the inner wall surface 113.

The spacer 17 has, for example, an annular shape and is provided around the space between the objective lens 16 and the inner wall surface 113. The spacer 17 is a part not only for preventing the objective lens 16 from coming into contact with the inner wall of the living body but for maintaining a fixed distance between the objective lens 16 and the inner wall surface 113.

The image processing unit 70 stores the converted electric signal (fluorescence intensity) from the photodetector 35 and the coordinate position of the imaging unit 10 sent from the control unit 50 with the electric signal and the coordinate position related to each other and processes the data on the electric signal and the coordinate position to generate a digital image. The generated digital image is, for example, displayed on a monitor, printed out, or recorded on the storage unit 51 in the control unit 50. The coordinate position of the imaging unit 10 may be expressed, for example, in the form of the distance from a reference location on the patient (throat or anus, for example) and the angle of revolution of the imaging head 11.

The control unit 50 is formed, for example, of a CPU, a ROM, and a RAM. The control unit 50 controls the action of the imaging head 11 via the inner tube 12. Specifically, the control unit 50 controls the movement of the imaging head 11 not only in the revolutional direction R along the inner circumference of the inner wall of the digestive tract 112 but in the tract longitudinal direction of the digestive tract 112 (along axis X of digestive tract). The control unit 50 further changes the position of the objective lens 16 in the optical axis direction by controlling the action of the focal point changer 18 to control the position where the focus is achieved in the living body. The control unit 50 can further adjust the laser power by controlling the laser oscillator 60.

The control unit 50 includes the evaluation unit 52, which evaluates the grade of cancerization, and the storage unit 51, which stores information that serves as an evaluation reference when the grade of cancerization is evaluated, as described above.

The storage unit 51 stores information on the grade of cancerization and information on the staining state of the living cell group with the two pieces of information related to each other. The grade of cancerization is, for example, expressed by the first to fourth stages divided in accordance with the state of the activity of each of the cancer-related genes, as shown in FIG. 1C. The information on the staining state of the living cell group contains, for example, the area of or the number of cells in the stained region (region stained in chromatic color) of the living cell group in each of the stages described above. The area of or the number of cells in the stained region varies in accordance with the type of the stain to be used and therefore needs to be acquired in advance in accordance with the stain to be used.

The evaluation unit 52 evaluates the grade of cancerization by comparing the staining state of a captured image with information on the staining states stored in the storage unit 51. For example, the evaluation unit 52 compares the area of or the number of cells in the stained region in the captured image with the area of or the number of cells in the stained region in each of the stages that is stored in the storage unit 51 to determine the stage to which the staining state of the living cell group belongs.

The cancer test device 1 according to the present embodiment includes the application unit 40, which applies to a living cell group the stain 45, which selectively stains a cancer-related gene expression pattern of the living cells in a chromatic color, the imaging unit 10, which images the living cell group to which the stain 45 has been applied, and the evaluation unit 52, which evaluates the grade of cancerization of the living cell group based on the staining state of the living cell group in the captured image. As image information, in addition to the area of or the number of cells in the stained region, a difference in the luminance or fluorescence color of the stained region or a difference in the geometric pattern of the stained region is used. The automatic diagnosis employs, for example, a method for identifying the expression location based on highly probable luminance and determining the grade of cancerization based on the state of mixed fluorescence colors. The method using the geometric pattern, although the pattern varies on an organ basis, can be a method for digitizing the density of dark portions (dark hole pattern), a method for digitizing the density of island-shaped patterns and recognizing disturbance of the island-shaped patterns, as described with reference to the section (c) of FIG. 4A and the section (a) of FIG. 4E, or any other diagnosis method. Further, it is effective to use the interval between the dark portions, the diameters of the dark portions, the interval in the island-shaped pattern, the diameter of the island-shaped pattern, or any other measured distance to evaluate and diagnose disturbance of the pattern.

The thus configured cancer test device 1 evaluates the grade of cancerization based on the staining state of the cancer-related gene expression patterns of the living cell group, whereby cancerization of the living cell group can be grasped in an early stage. Further, since the grade of cancerization can be grasped, the prognosis of the cancer patient can be understood.

Further, the cancer test device 1 can image, out of cancer-related gene expression patterns stained with the stain 45, a cancer-related gene expression pattern in a cell population having an average diameter at least greater than or equal to 0.1 mm but smaller than or equal to 0.4 mm. The grade of cancerization of the living cells in the pre-cancer state can therefore be grasped, whereby the prognosis of the cancer patient can be understood in the ultra-early stage before the cancer cell population 152 clearly manifests. The diameter of a cancer-related gene expression pattern is the diameter of a circle having the same area as the area of the cancer-related gene expression pattern. The average diameter is calculated by measuring the diameter described above of each stained cell group present in a fixed area and dividing the diameters by the number of stained cell groups.

Further, the cancer test device 1 according to the present embodiment can image a cancer-related gene expression pattern stained with the stain 45 and present over the depth range greater than or equal to 10 μm but smaller than or equal to 1000 μm below the mucosa surface in a living body. The grade of cancerization of the interior of the living body over the depth range greater than or equal to 10 μm but smaller than or equal to 1000 below the mucosa surface can therefore be grasped, whereby the cancer cell population 152 can be detected with no missing part in the ultra-early stage before the cancer cell population appears on the mucosa surface, and the prognosis of the cancer patient can be understood (FIG. 19A). For example, cellular morphological fluorescence images over a depth range from 10 μm to 50 μm below the mucosa surface of a digestive tract can be converted into a full-circumference panoramic image around the circumference of the digestive tract, as shown in FIG. 19A. As a result, "cancer detection with no missing part" can be achieved based on the image because the full circumference imaging is guaranteed. FIG. 19B shows the endoscope 2 of a cancer test device 1A.

The endoscope 2 of the cancer test device 1A includes the inner tube 12 and the outer tube 13, which surrounds part of the outer surface of the inner tube 12. A linear-motion actuator is attached to the inner tube 12, and the inner tube 12 is movable relative to the outer tube 13 in the axial direction X. An ultrasonic motor is further attached to the inner tube 12, and the inner tube 12 is revolvable relative to the outer tube 13 over 360°. The action of the inner tube 12 in the axial direction X or the revolutional direction R is controlled by the control unit 50. The cancer test device 1A allows understanding of the distance to a lesion in the axial direction X and the angle in the revolutional direction R with respect to a predetermined position, for example, the anus in the case of the large intestine and the mouse in the case of the stomach, whereby the position of the lesion can be identified.

[2. Example of Action of Cancer Test Device]

An example of the action of the cancer test device 1 according to the present embodiment will next be described. FIG. 12 is a flowchart showing an example of the action of the cancer test device 1.

A cleaning liquid is first supplied into the closed space S via the supply port 42 (not shown) before the stain 45 is applied in FIG. 8. The inner wall surface 113 of the digestive tract 112 is thus cleaned. The cleaning liquid is then sucked and recovered via the recovery port 43. A pronase liquid is then supplied via the supply port 42 into the closed space S. Excess of the mucus having adhered to the inner wall surface 113 of the digestive tract 112 is thus removed. The pronase liquid is then sucked and recovered via the recovery port 43.

The application unit 40 then applies the stain 45 containing a curcumin-based compound to a living cell group (S11a: application step). Specifically, the stain 45 containing a curcumin-based compound is supplied via the supply port 42 into the closed space S to fill the closed space S with the stain 45. The stain 45 is then left for 2 to 5 minutes, and the space S is then cleaned with the cleaning liquid. The STAT3-family cancer-related gene product in the living cell group in the digestive tract 112 is thus stained with the stain 45 containing a curcumin-based compound.

The application unit 40 containing the stain 45 containing phloxine is then used to apply the stain 45 containing phloxine to the living cell group (S11b: application step). Specifically, the stain 45 containing phloxine is supplied via the supply port 42 into the closed space S to fill the closed space S with the stain 45. The stain 45 is then left for 2 to 5 minutes, and the space S is then cleaned with the cleaning liquid. The ras-family cancer-related gene expression pattern in the living cell group in the digestive tract 112 is thus stained with the stain 45 containing phloxine. The application of the two types of stain 45 causes the living cell group in the inner wall of the digestive tract 112 to be double stained.

The imaging unit 10 then images the cancer-related gene expression patterns of the living cell group stained with the stains (S12: imaging step). Specifically, the control unit 50 performs the imaging while controlling the movement of the imaging head 11 not only in the revolutional direction R along the inner wall of the digestive tract 112 but in the tract longitudinal direction of the digestive tract 112 (along axis X of digestive tract).

The evaluation unit 52 then evaluates the grade of cancerization and the prognosis of the cancer patient based on the staining state in the captured image (S13: evaluation step).

Specifically, the area and the number of cells in the stained region stained with the stains 45 are determined. The area of each of the stained regions is determined by evaluating whether or not the staining has been performed for each pixel of the captured image based on a predetermined threshold and replacing the number of pixels determined to have been stained with a corresponding area. The number of cells in each of the stained regions is determined based on the number of nuclei of the cell or the number of compartments separated by the cell membrane in the stained region. Data on the resultant area or the number of cells is then compared with data stored in the storage unit 51 and representing the area or the number of cells to evaluate the grade of cancerization and the prognosis of the cancer patient.

For example, when the area of the stained region stained with the stain 45 containing phloxine is greater than or equal to 0.0075 mm$^2$ but smaller than 3 mm$^2$, it may be considered that the expression of the ras-family cancer-related gene product has been enhanced, and it may therefore be determined that the grade of cancerization is the second stage (see FIG. 1C) or later. For example, when the number of cells in the stained region stained with the stain 45 containing phloxine is greater than or equal to 8 but smaller than 512, it may be considered that the expression of the ras-family cancer-related gene product has been enhanced, and it may therefore be determined that the grade of cancerization is the second stage or later. Further, the second stage and the following stages may further be divided into sub-stages for the evaluation of the grade of cancerization and the prognosis of the cancer patient.

The grade of cancerization may be evaluated based on the state of the expression of the ras-family cancer-related gene product, as described above, but not necessarily. The grade of cancerization may instead be evaluated by using the stain 45 containing a curcumin-based compound based on the state of activity of the STAT3-family cancer-related gene. Still instead, a predetermined stain may be used to stain the APC/β-catenin-family or p53-family cancer-related gene expression pattern, and whether or not the amplitude of the growth inhibiting signal has decreased may be examined for evaluation of the grade of cancerization and the prognosis of the cancer patient.

The multiphoton-laser-microscope-based cancer test device 1 according to the present embodiment can also be used to remove a cancerous portion (cancer cell population) with the laser light.

For example, in a case where an image produced by the imaging unit 10 contains a cancerous portion, the power of the laser light L is increased as compared with the power in the imaging under the multiphoton laser microscope, and the laser light L having the increased power is applied to the cancerous portion to specifically remove (evaporate) only the cancerous portion. The laser power in the removing operation is 10 to 20 times the power in the imaging operation or ranges from 2 to 3 W. The cancerous portion can therefore be reliably removed in an early stage of the cancerous portion.

Second Embodiment

A cancer test device according to a second embodiment is a stationary test device and used in a case where a patient is externally tested or tissue cells immediately after removed from a patient but within about 20 minutes are tested.

A cancer test device 201 according to the present embodiment includes a laser oscillator 213, a beam diameter adjuster 215, a two-dimensional scanner 217, a dichroic mirror 219, an objective lens 221, a focused light depth adjuster 223, a photodetector 225, a fluorescence image generation unit 227, a monitor 229, and a control unit 231, as shown in FIG. 13.

The laser oscillator 213 to be used is configured to have a pulse width ranging from several tens to several hundreds of femtosecond and a pulse repetition frequency ranging from several tens to several hundreds of megahertz and further configured to be capable of adjusting the power of the pulse laser light or a CW laser outputting light having a visible wavelength for a typical confocal laser microscope.

In a case where the pulse laser for the multiphoton laser is used, the beam diameter adjuster 215 is a beam expander that changes the beam diameter of the pulse laser light in accordance with a beam diameter adjustment signal from the control unit 231.

The two-dimensional scanner 217 is formed, for example, of two galvanometric mirrors and changes the position where the pulse laser light is focused in two axial directions perpendicular to the optical axis.

The dichroic mirror 219 separates fluorescence produced in a cancer-related gene product in living cells when the living cells are irradiated with the pulse laser light.

The objective lens 221 focuses the pulse laser light emitted from the laser oscillator 213 in the living cells and focuses the fluorescence produced in the cancer-related gene product in the multiphoton absorption phenomenon. The focused light depth adjuster 223 can move the objective lens 221 in the optical axis direction based on a control signal, so that the focused light position where the laser light is focused can be adjusted.

The photodetector 225 detects the fluorescence produced in the cancer-related gene product and converts the fluorescence into an electric signal according to the intensity of the fluorescence.

The scan state of the two-dimensional scanner 217 and the adjusted focused light position provided by the focused light depth adjuster 223 (position in depth direction) are parameters representing the coordinates of the focused light position, and the fluorescence image generation unit 227 stores the parameters representing the coordinates and the electric signal (that is, fluorescence intensity) sent from the photodetector 225 with the parameters and the electric signal related to each other and processes the data on the parameters and the electric signal to produce a fluorescence image. The produced fluorescence image is displayed on the monitor 229.

The control unit 231 includes an action control unit 233, a test pulse intensity setting unit 235, an irradiation range setting unit 239, and an irradiation period setting unit 241. The action control unit 233 controls the actions of the laser oscillator 213, the beam diameter adjuster 215, the two-dimensional scanner 217, and the focused light depth adjuster 223.

The test pulse intensity setting unit 235 sets pulse laser light intensity suitable for acquisition of a fluorescence image of a cancer-related gene expression pattern to test the living cells.

The irradiation range setting unit 239 sets the range over which the living cells are irradiated with the pulse laser light. The action control unit 233 then controls the actions of the two-dimensional scanner 217 and the focused light depth adjuster 223 to cause the pulse laser light to be radiated and focused at the set depth within the set irradiation range. The irradiation period setting unit 241 sets a period for which the living cells are irradiated with the pulse laser light. The action control unit 233 controls the power of the pulse laser light from the laser oscillator 213 to cause the pulse laser light to be radiated only for the set period.

The control unit 231 in the present embodiment includes the same storage unit 51 and evaluation unit 52 as those in the first embodiment. That is, the cancer test device 201 evaluates the grade of cancerization and prognosis of the living cell group based on the staining state of the living cell group in the captured image.

The cancer test device 201, which evaluates the grade of cancerization based on the staining state of the cancer-related gene expression pattern in the living cell group, can grasp the cancerization of the living cell group in an early stage. Further, the cancer test device 201, which allows grasp of the grade of cancerization based on the state of expression of the cancer-related gene, allows understanding of the prognosis of the cancer patient.

The cancer test device 201 includes a treatment pulse intensity setting unit 237, which can set pulse laser light intensity intense enough to destroy the living cells for treatment thereof. Cancer treatment can therefore be performed on the found cancer cell population in an early stage.

In addition to the above, the cancer test device 201 according to the present embodiment can be implemented in a variety of other forms.

For example, the beam diameter adjuster 215, the two-dimensional scanner 217, an optical system formed of the dichroic mirror 219, the objective lens 221, and the optical path therebetween, and the focused light depth adjuster 223 may be provided in a laser light radiation head 243, and a patient fixation bench 245, on which a patient lies, and a mover 247 may be further provided, as shown in FIG. 14 to perform a cancer test.

Further, for example, in a state in which part of a living cell group is scraped off a patient and the scraped living cell group is placed on a tray (specimen mount), the cancer test device 201 can be used to image the living cell group and evaluate the grade of cancerization. In this case, the stain 45 may be applied to the living cell group before the living cell group is scraped off or after the living cell group is scraped off but before the imaging.

Third Embodiment

[1. Basic Configuration of Cancer Test Device]

The basic configuration of a cancer test device 301 according to a third embodiment, which is a case where a CW laser outputting light having a visible wavelength for a typical confocal laser microscope is used, will next be described with reference to FIGS. 15 to 18.

FIG. 15 is a schematic view showing a front-end-side end portion of the endoscope 2 of the cancer test device 301 in FIG. 17. FIG. 16 is a schematic view showing the entire endoscope 2. FIG. 17 is a block diagram showing the control configuration of the cancer test device 301.

The cancer test device 301 includes the imaging unit 10, which includes the endoscope 2, the control unit 50, and the image processing unit 70, as shown in FIG. 17. The cancer test device 301 further includes a laser oscillator 60C and an optical part 65C. The cancer test device 301 still further includes the application unit 40, which supplies a stain to the interior of a living body (see FIG. 8).

The laser light L1 emitted from the laser oscillator 60C is reflected off a dichroic mirror 66C, which is the optical part 65C, further reflected off a mirror 19C in the endoscope 2, and applied to the living body. Living cells irradiated with the laser light L1 produce fluorescence, and the fluorescence is reflected off the mirror 19C, passes through the dichroic mirror 66C, and is detected with a photodetector 35C. The light detected with the photodetector 35C is converted into an electric signal, and the image processing unit 70 forms an image according to the electric signal. Since the color of the fluorescence changes in accordance with the stain, the photodetector 35C can be formed of a plurality of photodetectors, and a color separation optical filter can be disposed on the upstream side of the photodetector 35C for color separation. The actions, functions, and roles of the parts described above are roughly the same as those in FIG. 11, but the reference numerals of the parts are suffixed with "C" representing the first letter of the CW laser for distinction purposes because a confocal laser microscope differs in principle from a multiphoton laser microscope.

The laser oscillator 60C includes a plurality of lasers that allow the wavelength of the laser light L1 to be changed stepwise over a wavelength range from 405 to 980 nm, and the wavelength is selected in accordance with the characteristics of a fluorescence reaction that occurs in a measurement target. The lasers may each operate in pulses or continuous oscillation. In the case of pulse operation, the operation frequency is at least several tens of kilohertz, and the duty ranges from 5% to 50%. The frequency and duty ranges are so selected in consideration of the imaging sweep frequency that a sharp image is produced. The laser light L1 in the present embodiment is confocal laser light, and the laser oscillator 60C uses, for example, a laser capable of emitting light having an intensity peak wavelength of 488 nm, 594 nm, or 647 nm and a power of 30 mW at the maximum. The power of the laser light emitted from the laser in the imaging operation ranges from 5 to 10 mW, but not necessarily. The laser oscillator 60C can adjust the intensity of the laser light L1 in accordance with the degree of staining and the degree of the intensity of fluorescence.

The dichroic mirror 66C, which is the optical part 65C, reflects light having the same wavelength as that of the laser light L1 and transmits light having the other wavelengths. The laser light L1 emitted from the laser oscillator 60C is therefore reflected off the dichroic mirror 66C toward the mirror 19C. On the other hand, the fluorescence produced in the living cells is reflected off the mirror 19C, then passes through the dichroic mirror 66C, and reaches the photodetector 35C. The optical part 65C can instead be formed, for example, of a prism or a λ/4 plate.

The imaging unit 10 includes the endoscope 2 and the photodetector 35C and applies the laser light L1 to the interior of the living body to image the cell form in the living body.

The photodetector 35C detects the fluorescence produced when the laser light L1 is applied to the living cells and converts the fluorescence into an electric signal according to the intensity of the fluorescence. The photodetector 35C can, for example, be a photomultiplier or a CCD semiconductor image sensor. A pinhole or any other component is provided as a part that provides the confocal laser function.

The endoscope 2 includes the inner tube 12 and the outer tube 13, which surrounds part of the outer surface of the inner tube 12, as shown in FIG. 16. The inner tube 12 and part of the outer tube 13 are inserted into the living body. The inner tube 12 has a length, for example, of 50 mm and an outer diameter ranging, for example, from 3 to 10 mm. A linear-motion actuator is attached to the inner tube 12, and the inner tube 12 is movable relative to the outer tube 13 in the axial direction X by about 25 mm. An ultrasonic motor is further attached to the inner tube 12, and the inner tube 12 is revolvable relative to the outer tube 13 over 360°. The action of the inner tube 12 in the axial direction X or the revolutional direction R is controlled by the control unit 50.

An imaging head 11C is provided at a front-end-side end portion of the inner tube 12 of the endoscope 2. The imaging head 11C is inserted along with the inner tube 12 into the living body in such a way that the imaging head 11C and the inner tube 12 pass by the insertion tube 20, as shown in FIG. 15. The imaging head 11C is so controlled as to move in the living body based on the actions of the inner tube 12 in the axial direction X and the revolutional direction R.

The imaging head 11C includes an objective lens 16C, the focal point changer 18, the spacer 17, and the mirror 19C.

The mirror 19C is a part that redirects the laser light L1 outputted from the laser oscillator 60C toward the objective lens 16C or redirects the fluorescence emitted from the living cells toward the photodetector 35C, as described above.

The objective lens 16C is so provided as to face the inner wall surface 113 of the living body. The objective lens 16C has, for example, a diameter of 10 mm, a magnification of 10 times, a resolution of 5 µm, and an imaging field of view of 3 mm×3 mm. The objective lens 16C instead has a diameter of 12 mm, a magnification of 40 times, a resolution of 10 µm, and a field of view of 7.5 mm×7.5 mm. The wider the imaging field of view, the better. The objective lens 16C may still instead be so configured that part of a lens having either of the diameters described above is cut or the diameter of the objective lens 16C is reduced to a value ranging from 3 mm to 5 mm so that the objective lens is readily inserted into the living body with the same resolution maintained. The objective lens 16C may be so disposed as to incline with respect to the inner wall surface 113. Performing the imaging with the objective lens 16C inclining allows the cell forms of the epithelium 120 and the gland 130 to be simultaneously observed.

The focal point changer 18 is, for example, a piezoelectric actuator or an electromagnetic actuator and moves the objective lens 16C in the optical axis direction to change the position of the focal point of the objective lens 16C. The focal point changer 18 operates under the control of the control unit 50 and can adjust the focal point over a depth range from 0 to 75 µm below the inner wall surface (mucosa surface) 113. Changing the position of the focal point allows imaging of the state of the living body at a predetermined depth below the inner wall surface 113 of the digestive tract 112.

The spacer 17 has, for example, an annular shape and is provided around the space between the objective lens 16C and the inner wall surface 113. The spacer 17 is a part not only for preventing the objective lens 16C from coming into contact with the inner wall of the living body but for maintaining a fixed distance between the objective lens 16C and the inner wall surface 113. The distance between the objective lens 16C and the inner wall surface (mucosa surface) 113 is set at an appropriate value, for example, a value greater than or equal to 1 mm but smaller than or equal to 10 mm by exchanging the spacer 17 to another before the imaging starts or adding a distance changeable mechanism using an actuator or any other device. The control unit 50 controls the movement of the imaging head 11C (inner tube 12) with the spacer 17 being in contact with the inner wall surface 113 and maintains the fixed distance from the objective lens 16C to the inner wall surface 113.

The control unit 50 is formed, for example, of a CPU, a ROM, and a RAM. The control unit 50 controls the action of the imaging head 11 via the inner tube 12. Specifically, the control unit 50 controls the movement of the imaging head 11C not only in the circumferential direction along the inner circumference of the inner wall of the digestive tract 112 but in the tract longitudinal direction of the digestive tract 112 (along axis of digestive tract). The control unit 50 further changes the position of the objective lens 16C in the optical axis direction by controlling the action of the focal point changer 18 to control the position where the focus is achieved in the living body. The control unit 50 can further adjust the laser power by controlling the laser oscillator 60C.

The image processing unit 70 stores the converted electric signal (fluorescence intensity) from the photodetector 35C and the coordinate position of the imaging unit 10 sent from the control unit 50 with the electric signal and the coordinate position related to each other and processes the data on the electric signal and the coordinate position to generate a digital image. The generated digital image is, for example, displayed on a monitor, printed out, or recorded on a storage device. The coordinate position of the imaging unit 10 may be expressed, for example, in the form of the distance from a reference location on the patient (throat or anus, for example) and the angle of revolution of the imaging head 11C.

The confocal-laser-endoscope-based cancer test device 301 according to the present embodiment includes the imaging unit 10, which includes the imaging head 11C, which is inserted into a living body, and images the living body by applying the laser light to the living body via the imaging head 11C, and the control unit 50, which controls the operation of the imaging head 11C. The imaging head 11C includes the objective lens 16C and the focal point changer 18, which is capable of changing the position of the focal point of the objective lens 16C in the depth direction of the living body, and the control unit 50 causes the focal point changer 18 to operate in such a way that the position of the focal point has a predetermined depth deeper than or equal to 10 µm but shallower than or equal to 100 µm (desirably deeper than or equal to 10 µm but shallower than or equal to 70 µm) below the mucosa surface in the living body. The imaging unit 10 applies the laser light to a cell group present in the living body and stained with the stain 45, which selectively stains the cell group in a chromatic color, and images the stained cell group at the predetermined depth.

A method for controlling the focal point with a fixed positional relationship between the objective lens 16C and the mucosa surface maintained will be described. Reference character 171 in FIG. 17 denotes a second laser oscillator, which emits continuous parallelized light as reference light L2, for example, having a wavelength of 680 nm and a power of about 5 mW. A beam splitter, a half-silvered mirror, or any other component causes the light from the second laser oscillator 171 to travel along the optical path of the light from the laser oscillator 60C. In FIG. 17, the optical path of the reference light L2 is drawn with a broken line slightly shifted from the optical path of the light from the laser oscillator 60C for ease of understanding. The reference light L2 described above travels along roughly the same path as that of the cancer-test laser light L1 but travels along a different optical path beyond a beam splitter 173 and enters a focal point control optical unit 174. In a case where the position of the focal point of the objective lens 16C changes, a cylindrical lens, a beam splitter, and other components form an optical part configuration capable of detecting the amount of change in the position of the focal point. Reference character 175 denotes a photodetector that is typically divided into 2 or 4 blocks. The light detected with the thus configured photodetector is converted, for example, with a differential amplifier into an electric signal proportional to a change in the positional relationship between the objective lens 16C and the mucosa surface. The control of the position of the objective lens described above is used, for example, in an optical disk device and is fully applicable to an endoscope device. To apply the position control described above to a cancer test device, a point to be aware of is that the laser light L1 for imaging and the reference light L2 preferably have different wavelengths so that the two light beams are readily separated from each other. Separating the wavelengths of the two light beams from each other by at least 100 nm achieves optical characteristics of the imaging system and the focal point control system that allow the two light beams to be satisfactorily separate from each other. In the case where the focal point control system described above is provided, applying bias voltage to the control system allows fine adjustment of the position of the focal point. Changing the bias voltage stepwise allows automatic control of the position where the laser light L1 is focused in the depth direction.

The transmittance or reflectance of the optical parts 11C, 35C, 65C, 66C, 172, 173, and 174 greatly depends on the wavelength of the laser light beams L1 and L2. Modularizing the optical parts in accordance with the wavelengths of the laser light beams and preparing a plurality of modules can therefore readily handle a situation in which the wavelengths of the laser light beams are changed in accordance with the stain to be used or a body site to be tested.

As described above, even the cancer test device 301 including the confocal laser endoscope can acquire images at the depths deeper than or equal to 10 µm but shallower than or equal to 70 µm below the inner wall surface (mucosa surface) 113 of the living body. As a result, a lesion can be readily found, and selecting the wavelengths and the intensities of the laser light beams allows acquisition of images with no load on the patient, such as optical damage of cells irradiated with the laser light.

[2. Action of Cancer Test Device]

The action of the cancer test device 301 according to the present embodiment will next be described. FIG. 18 is a flowchart showing an example of the action of the cancer test device 301. In the cancer test device 301 according to the present embodiment, the two different stains 45 are applied to a living cell group to stain two cancer-related gene expression patterns in colors different from each other, and the stained cancer-related gene expression patterns are imaged.

A cleaning liquid is first supplied into the closed space S via the supply port 42 (not shown) before the stains 45 are applied. The inner wall surface 113 of the digestive tract 112 is thus cleaned. The cleaning liquid is then sucked and recovered via the recovery port 43. A pronase liquid is then supplied via the supply port 42 into the closed space S. Excess of the mucus having adhered to the inner wall surface 113 of the digestive tract 112 is thus removed. The pronase liquid is then sucked and recovered via the recovery port 43.

The application unit 40 then applies the stain 45 containing a curcumin-based compound to the living cell group (S11a: application step). Specifically, the stain 45 containing a curcumin-based compound is supplied via the supply port 42 into the closed space S to fill the closed space S with the stain 45. The stain 45 is then left for 2 to 5 minutes, and the space S is then cleaned with the cleaning liquid. The STAT3-family cancer-related gene product in the living cell group in the digestive tract 112 is thus stained with the stain 45 containing a curcumin-based compound.

The application unit 40 containing the stain 45 containing phloxine is then used to apply the stain 45 containing phloxine to the living cell group (S11b: application step). Specifically, the stain 45 containing phloxine is supplied via the supply port 42 into the closed space S to fill the closed space S with the stain 45. The stain 45 is then left for 2 to 5 minutes, and the space S is then cleaned with the cleaning liquid. The ras-family cancer-related gene expression pattern in the living cell group in the digestive tract 112 is thus stained with the stain 45 containing phloxine.

The imaging unit 10 then images the cancer-related gene expression patterns of the living cell group stained with the two stains 45 described above (S12: imaging step). Specifically, the cancer-related gene expression patterns stained in the two different colors are irradiated with excitation light beams having two different wavelengths to allow the imaging unit 10 to image the plurality of cancer-related gene expression patterns. In the present embodiment, the laser light L1 having a wavelength of 488 nm is radiated as the excitation light beams for causing the cancer-related gene expression pattern stained with the stain 45 containing a curcumin-based compound to emit fluorescence, and the laser light L1 having a wavelength of 594 nm is radiated as the excitation light beams for causing the cancer-related gene expression pattern stained with the stain 45 containing phloxine to emit fluorescence. The cancer-related gene expression patterns stained in the two colors are then sequentially irradiated with the two types of laser light L1, and fluorescence produced by the irradiation is detected with the photodetector 35C.

The evaluation unit 52 then evaluates the grade of cancerization and the prognosis of the cancer patient based on the staining states in the captured image (S13: evaluation step).

As described above, the cancer-related gene expression patterns stained with the two stains 45 are each irradiated with excitation light beams according to the corresponding stain 45 for detection of the state of the activity of the plurality of cancer-related genes and evaluation of the grade of cancerization. Further, irradiating each of the cancer-related gene expression patterns with the laser light L1 having a single wavelength as described above allows stable detection of the fluorescence emitted from the cancer-related gene expression pattern.

The above description has been made with reference to the case where the two stains 45 and excitation light beams corresponding thereto are used to detect two cancer-related gene expression patterns, but not necessarily. Three or more stains 45 and excitation light beams corresponding thereto may be used to detect three or more cancer-related gene expression patterns. The stain 45 is not limited to a curcumin-based compound or phloxine and may instead be High Red V80, sulfuretin, erythrosine, epigallocatechin-gallate, indocyanine green, malvidin, β-carotene, High Red BL, 6-gingerol, myricetin, tricenidine, or petunidine.

For example, use of the stain 45 that stains the cancer-related gene expression pattern of the APC/β-catenin family or the p53 family, which is a brake-system gene, allows examination of whether or not the amplitude of the cell growth inhibiting signal has decreased. Therefore, a brake-system gene can be detected, and the prognosis of the cancer patient can be evaluated.

As described above, staining cancer-related gene expression patterns with many stains 45 and irradiating each of the stained cancer-related gene expression patterns with excitation light beams according to the corresponding stain 45 allows detection of the many cancer-related genes. The grade of cancerization can therefore be analyzed from diverse viewpoints, whereby the probability of evaluation of the prognosis can be increased.

Determination of a cancerous site and a healthy site based on the permeability difference of the edible pigments between these two sites will next be described.

A case where a cell form in a living body is imaged under the multiphoton laser microscope (FV1000MPE manufactured by Olympus Corporation) while changing the depth of the focal point and a plurality of captured images are cut in a predetermined position to create a cross-sectional image (tomographic image) will be described with reference to FIGS. 20A, 20B, and 20C. A laboratory mouse was used as the living body.

FIGS. 20A to 20C show images illustrating the cell form over a predetermined depth range below the inner wall surface (mucosa surface), specifically, three-dimensional data images obtained by performing imaging at 2-μm intervals from the mucosa surface (depth 0) to a depth of 150 μm and layering the captured 75 images in total on one another. In each of FIGS. 20A to 20C, the section (a) shows an image of the cell group in a plan view viewed in the direction perpendicular to the inner wall surface 113, the section (b) shows a cross-sectional image of the section (a) taken along the line b-b, and the section (c) shows a cross-sectional image of the section (a) taken along the line c-c.

As the stain for staining the cell group, both the stain containing curcumin and the stain containing Acid Red (red #106) were used. The staining period was set at 5 minutes. The staining period is the period for which the stain is caused to be in contact with the cell group and the dye of the stain is allowed to penetrate into the cells themselves or the gaps between the cells.

FIGS. 20A to 20C show images obtained by imaging the same cell group at the same time and filtering the images to extract different colors (wavelengths). FIG. 20A shows images representing the extracted color region stained both with the curcumin dye and the Acid Red dye. FIG. 20B shows images representing the extracted color region stained with the curcumin dye. FIG. 20C shows images representing the extracted color region stained with the Acid Red dye. FIGS. 20A to 20C show monochromatic images that are inherently color images, and the difference in the tendency of the staining performed by the stains causes the region stained with the curcumin dye to be displayed in a green fluorescent color and the region stained with the Acid Red dye to be displayed in a pale red or a near orange fluorescent color, whereby the difference in color is more distinctively expressed.

FIGS. 20A to 20C show cancer tissue and healthy mucosa tissue and indicate that the dyes differ from each other in terms of permeability. The curcumin dye shows higher permeability in the cancer tissue than in the healthy mucosa tissue, as shown in FIG. 20B. Specifically, in the case of the curcumin dye, the depth to which the tissue is stained is about 40 μm in the cancer tissue, whereas the depth is about 20 μm in the healthy mucosa tissue. The Acid Red dye shows lower permeability in the cancer tissue than in the healthy mucosa tissue, as shown in FIG. 20C. Specifically, in the case of the Acid Red dye, the depth to which the tissue is stained is about 40 μm in the cancer tissue, whereas the depth is about 70 μm in the healthy mucosa tissue.

As described above, the permeability of a dye varies depending on whether the cell form is cancer tissue or healthy mucosa tissue. It is believed based on the characteristic described above that measurement of the depth to which a cell group displayed in a cross-sectional image is stained allows identification of the cell group, a healthy cell group or a cancer cell group. The cancer test device performs depth direction control below the cell surface at the time of imaging to evaluate whether the cell group displayed in the cross-sectional image is suspicious of a lesion based on a depth to which the cell group has been stained. For example, when the depth to which the cell group has been stained with the curcumin dye is (at least 1.5 times, for example) greater than the depth to which the healthy mucosa tissue has been stained with the curcumin dye, the control unit 50 determines that cancer cells have developed, whereas when the two depths are similar to each other (difference is smaller than 1.5 times, for example), the control unit 50 determines that no cancer cells have developed. Further, when the depth to which the cell group has been stained with the Acid Red dye is (at least 0.6 times, for example) smaller than the depth to which the healthy mucosa tissue has been stained with the Acid Red dye, the control unit 50 determines that cancer cells have developed, whereas when the two depths are similar to each other (difference is at least 0.6 times, for example), the control unit 50 determines that no cancer cells have developed. It is noted that after whether or not cancer cells are present is evaluated based, for example, on single or double staining, the evaluation described above based on a cross-sectional image increases the reliability of the evaluation. In the present example, curcumin, which stains the STAT3-family cancer-related gene product with a high degree of penetration, and Acid Red, which penetrates into a healthy cell by a high degree, are used. Staining a sample with phloxine, erythrosine, or any other stain that penetrates into a ras-family cancer gene product with a high degree of penetration allows comparison between the degrees of progress of the STAT3 family and the ras family in terms of the degree of stain penetration.

Other Examples

The cancer test devices 1, 201, and 301 according to the embodiments of the present invention have been described, but the present invention is not limited to the embodiments described above and variations thereof. For example, aspects in which the embodiments described above and variations thereof are changed as follows may also fall within the scope of the present invention.

For example, in the first embodiment, to stain a cancer-related gene expression pattern, stains are used one by one for sequentially staining, but not necessarily. A plurality of dyes may be mixed with one another in advance to produce a mixed stain containing the plurality of dyes, and the mixed stain may be used to perform simultaneous staining. Further, an oral cleaning liquid containing a mucosa cleaning agent, a stain, and other substances may be used to stain a digestive tract. In the above description, the staining has been described in two ways: A cancer-related gene expression pattern is stained; and a cancer-related gene product is stained. The cancer-related gene expression pattern is not only a result of the operation of staining a cancer-related gene product but a state in which the cancer-related gene product having grown to some extent is the observation target.

In the first embodiment, a living body is stained with two different color stains before the imaging, but not necessarily. A living body may be stained with three or more different color stains before the imaging.

In the first and second embodiments, multiphoton laser light is used as laser light for the cancer test device 1, but not necessarily, and confocal laser light can instead be used. Still instead, a typical CW laser microscope or a single-color fluorescence microscope may also be used as long as the wavelength to be used is appropriately selected. From the viewpoint of depth-direction imaging and resolution, it is desirable to use multiphoton laser light having a wavelength ranging from 600 nm to 1600 nm. However, achieving the analysis described above to some extent under a confocal laser microscope using a wavelength ranging from 400 to 700 nm or a fluorescence microscope using a typical CW laser that emits light having a wavelength ranging from 400 to 700 nm or single-color light having a wavelength ranging from 400 to 700 nm by skillfully selecting a lens or a wavelength to achieve magnification or resolution that allows the nucleus of a stained cell to be viewed falls within the scope of the present invention. Further, changing the wavelength of the laser light with which a sample is irradiated and changing a filter for image formation in accordance with the wavelength of the fluorescence emitted from a stain have been described above.

The cancer test devices 1, 201, and 301 according to the first and second embodiments are also applicable to luminal organs (such as bronchus, urinary bladder, and urinary duct) other than digestive tracts, and can further visualize the kidney, the liver, the brain, the retina, and other cell structures although there is a restriction on the visualization range of 1 mm or smaller in depth below the surface of the sample.

Further, the images described above are not limited to still images and may instead be motion images or a combination of still images and motion images. For example, motion images can be captured in preparatory diagnosis, a postoperative regular test, and other occasions, whereas stills image can be used in precise diagnosis. The enlargement magnification scale at the time of imaging is also not limited to fall within the ranges described above.

Cell tissue to be stained in living body staining may be an in-vivo cell tissue or fresh ex-vivo cell tissue within 20 minutes immediately after the cell tissue is surgically excised or otherwise separated out of the living body.

Further, the cancer test devices described above each have been described on the assumption that the cancer test device includes the staining unit, the imaging unit including an endoscope, the storage unit, and the evaluation unit, but the cancer test device does not necessarily include both the staining unit and the evaluation unit. A configuration in which another device performs the staining and a configuration in which the content in the storage unit is shared with another device or a computer and the other device or the computer performs the analysis and evaluation fall within the scope of the present invention. Further, the imaging unit does not necessarily include an endoscope depending on a site to be analyzed and may instead include a microscope having a fixed objective lens, as the specification describes both the cases described above. The latter case therefore, of course, falls within the scope of the present invention.

INDUSTRIAL APPLICABILITY

The cancer test devices according to the present invention are used to find cancer in an early stage in the digestive tract, the respiratory system, the renal/urinary system, the utero-ovarian reproductive system, the cerebrospinal nervous system, and other body sites.

EXPLANATION OF SIGNS 1, 1A, 201, 301 Cancer test device
2 Endoscope
10 Imaging unit
11, 11C Imaging head
12 Inner tube
13 Outer tube
16, 16C Objective lens
17 Spacer
18 Focal point changer
19, 19C Mirror
20 Insertion tube
21 First balloon
22 Second balloon
35, 35C Photodetector
40 Application unit
42 Supply port
43 Recovery port
45 Stain
50, 231 Control unit
51 Storage unit
52 Evaluation unit
60, 60C Laser oscillator
65, 65C Optical part
66, 66C Dichroic mirror
67 Two-dimensional scanner
70 Image processing unit
112 Digestive tract
113 Inner wall surface of digestive tract (mucosa surface)

120 Epithelium
121 Epithelial cell
125 Nucleus of epithelial cell
126 Cytoplasm of epithelial cell
130 Gland
131 Glandular cell
132 Capillary
133 Connective tissue
135 Nucleus of glandular cell
136 Cytoplasm of glandular cell
137 Basement membrane
138 Crypt
152 Cancer cell population
160 Muscular layer of mucosa
L, L1 Laser
L2 Reference light
S Closed space

The invention claimed is:

1. A cancer test device comprising:
an application unit that applies a stain that selectively stains a cancer-related gene product of living cells in a chromatic color to a living cell group, wherein, the cancer-related gene product is STAT3-family cancer-related gene product that transmits a signal that promotes growth of the living cells and the stain is a curcumin-based compound;
an imaging unit that images the living cell group to which the stain has been applied; and
an evaluation unit that evaluates a grade of cancerization of the living cell group and diversity of cancer-related gene expression based on a staining state of the living cell group in an image produced by the imaging.

2. The cancer test device according to claim 1, wherein the evaluation unit performs the evaluation based on an area of a stained region of the living cell group.

3. The cancer test device according to claim 1, wherein the evaluation unit performs the evaluation based on number of stained cells in a stained region of the living cell group.

4. The cancer test device according to claim 1, wherein the evaluation unit performs the evaluation based on number and average diameter of stained cell groups in a fixed area containing a stained region of the living cell group.

5. The cancer test device according to claim 1, wherein the imaging unit images the living cell group to which the stain has been applied by irradiating it with multiphoton or confocal laser light.

6. The cancer test device according to claim 1, wherein the imaging unit images the cancer-related gene expression pattern stained with the stain and having a diameter larger than or equal to 0.1 mm but smaller than or equal to 0.4 mm.

7. The cancer test device according to claim 1, wherein the application unit stains a plurality of the cancer-related gene expression patterns in colors different from one another by applying a plurality of the different stains to the living cell group, and the imaging unit images a plurality of the cancer-related gene expression patterns by irradiating the plurality of cancer-related gene expression patterns stained in the different colors with a plurality of excitation light beams according to the stains.

8. The cancer test device according to claim 7, wherein the stains are formed of at least two types of stain, and the excitation light beams with which the plurality of cancer-related gene expression patterns are irradiated are selected in correspondence with the types of the stain.

9. The cancer test device according to claim 1, wherein the imaging unit includes a focal point position control unit and controls the focal point position control unit to image the cancer-related gene expression pattern presenting at a depth deeper than or equal to 10 µm but shallower than or equal to 1000 µm below a surface in the living body stained with the stain.

10. The cancer test device according to claim 9, wherein the focal point position control unit is controlled to change a focal point at fixed intervals from the surface in the same imaging position in the living body stained with the stain to perform imaging at different-depth focal point positions, a plurality of captured images is superimposed on one another in a focal point position information order into a stereoscopic image, and the evaluation is performed based on a degree of penetration of the stain in the stereoscopic image.

11. The cancer test device according to claim 1, wherein the application unit applies the stain containing a curcumin-based compound to the living cell group and then applies a stain that stains a ras-family cancer-related gene product that transmits a signal that promotes growth of the living cells, wherein the stain that stains a ras-family cancer-related gene product is phloxine, erythrosine, merbromin, fast green FCF, or meclocycline sulfosalicylate to the living cell group.

* * * * *